US012642780B2

(12) United States Patent
Karin et al.

(10) Patent No.: US 12,642,780 B2
(45) Date of Patent: Jun. 2, 2026

(54) METHODS AND COMPOSITIONS TO TREAT AND PREVENT VIRAL INFECTIONS AND ACUTE RESPIRATORY DISTRESS SYNDROME

(71) Applicant: The Regents of the University of California, Oakland, CA (US)

(72) Inventors: Michael Karin, La Jolla, CA (US); Elsa Sanchez-Lopez, La Jolla, CA (US); Hongxu Xian, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 531 days.

(21) Appl. No.: 18/027,608

(22) PCT Filed: Sep. 30, 2021

(86) PCT No.: PCT/US2021/053038
§ 371 (c)(1),
(2) Date: Mar. 21, 2023

(87) PCT Pub. No.: WO2022/072745
PCT Pub. Date: Apr. 7, 2022

(65) Prior Publication Data
US 2025/0288542 A1      Sep. 18, 2025

Related U.S. Application Data

(60) Provisional application No. 63/086,445, filed on Oct. 1, 2020.

(51) Int. Cl.
A61K 31/155 (2006.01)
A61K 45/06 (2006.01)
A61P 11/00 (2006.01)

(52) U.S. Cl.
CPC ............ A61K 31/155 (2013.01); A61K 45/06 (2013.01); A61P 11/00 (2018.01)

(58) Field of Classification Search
CPC ................................................. A61K 31/155
See application file for complete search history.

(56) References Cited

U.S. PATENT DOCUMENTS

| | | |
|---|---|---|
| 6,191,162 B1 | 2/2001 | Byrd et al. |
| 2006/0116721 A1 | 6/2006 | Yun et al. |
| 2010/0254944 A1 | 10/2010 | Subramanian et al. |
| 2017/0231929 A1 | 8/2017 | Udono et al. |

OTHER PUBLICATIONS

Koh et al. CAS: 158: 523349, 2013.*
TelyRx.*
Chen et al. Chinese Medical Journal, 2018, 131(3);376-377,.*
Wikipedia for metformin.*
Chen et al., "Metformin Might Inhibit Virus through Increasing Insulin Sensitivity", Chinese Medical Journal, Feb. 5, 2018, vol. 131, Iss. 3, pp. 376-377.
Crouse et al., "Metformin Use is Associated with Reduced Mortality in a Diverse Population with COVID-19 and Diabetes", Frontiers in Endocrinology, Jul. 31, 2020, 21 pages.
International Search Report and Written Opinion dated Feb. 16, 2022, for application No. PCT/US2021/053038.
Menendez et al., "Metformin and SARS-CoV-2: mechanistic lessons on air pollution to weather the cytokine/thrombotic storm in COVID-19", Aging, May 27, 2020, vol. 12, No. 10, pp. 8760-8765.
Xian, et al., "Metformin inhibition of mitochondrial ATP and DNA synthesis abrogates NLRP3 inflammasome activation and pulmonary inflammation", Immunity, 54, pp. 1-15.
Yu et al., "Metformin relieves acute respiratory distress syndrome by reducing miR-138 expression", European Review for Medical and Pharmacological Sciences, 2018, 22, pp. 5355-5363.

* cited by examiner

*Primary Examiner* — Rei Tsang Shiao
(74) *Attorney, Agent, or Firm* — Foley & Lardner LLP

(57)                    ABSTRACT

Provided herein is a method for one or mor of preventing, treating, reducing the severity of acute respiratory distress syndrome (ARDS) in a subject at risk for contracting ARDS and infected with a coronavirus or SARS-CoV-2, comprising administering to the subject metformin, an analog or a derivative thereof, thereby preventing, treating, or reducing the severity of ARDS in the subject.

13 Claims, 42 Drawing Sheets

A

B

A

B

C

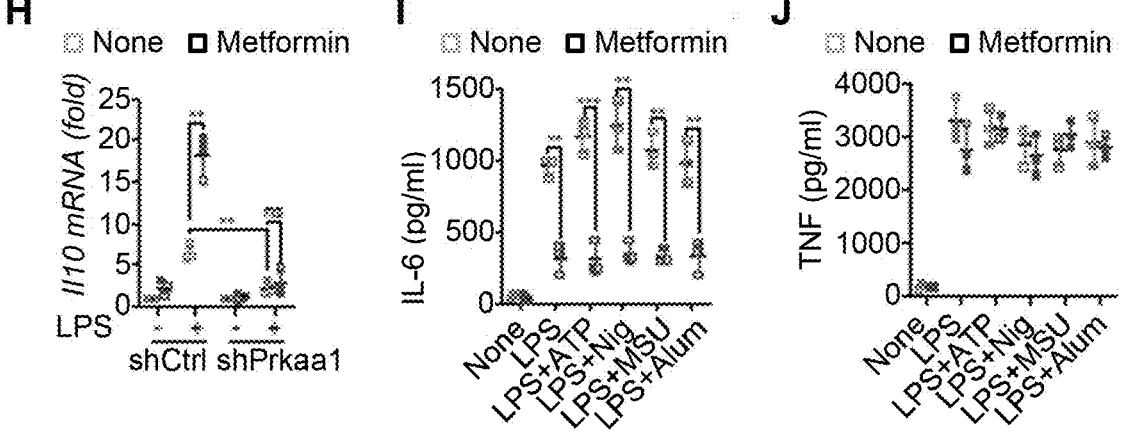
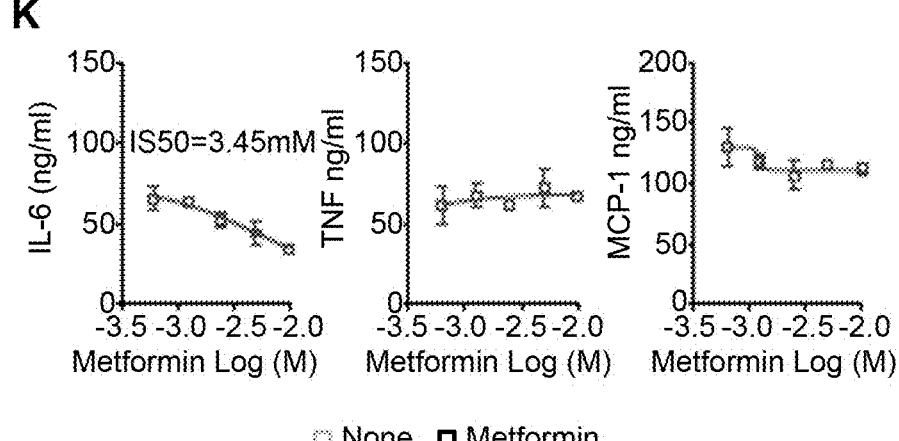
FIGS. 8H – 8K

L

M

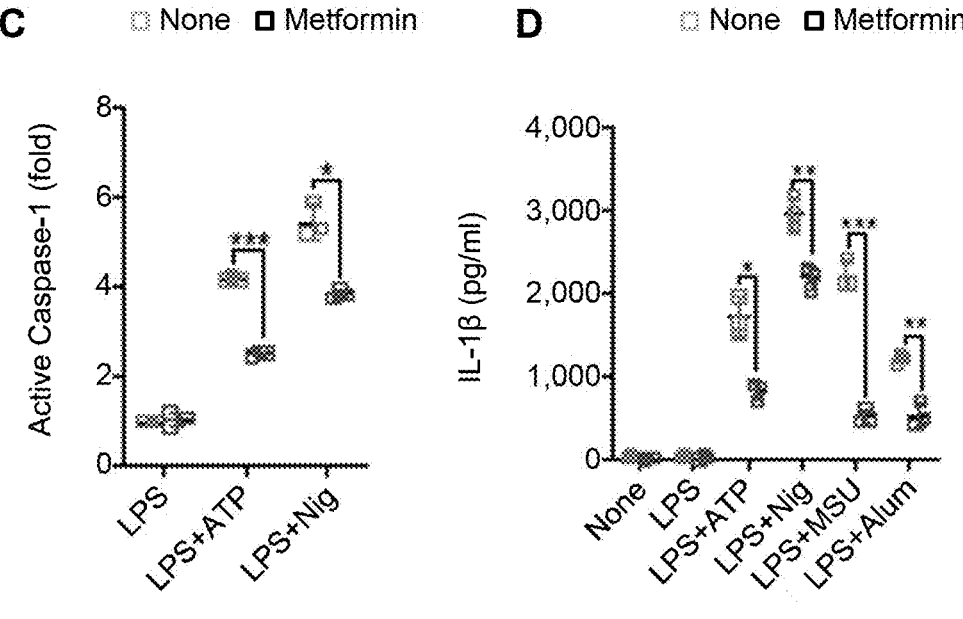
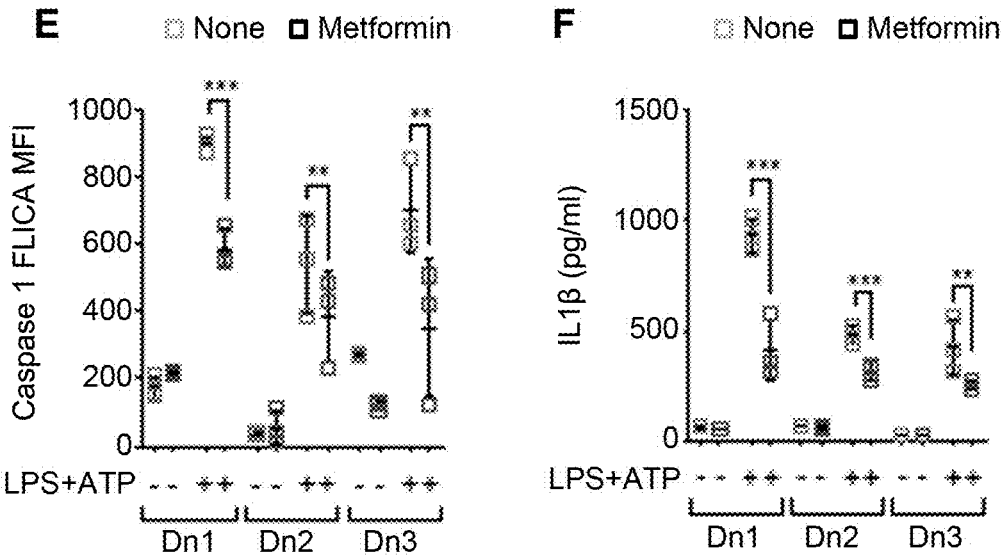
FIGS. 9C – 9F

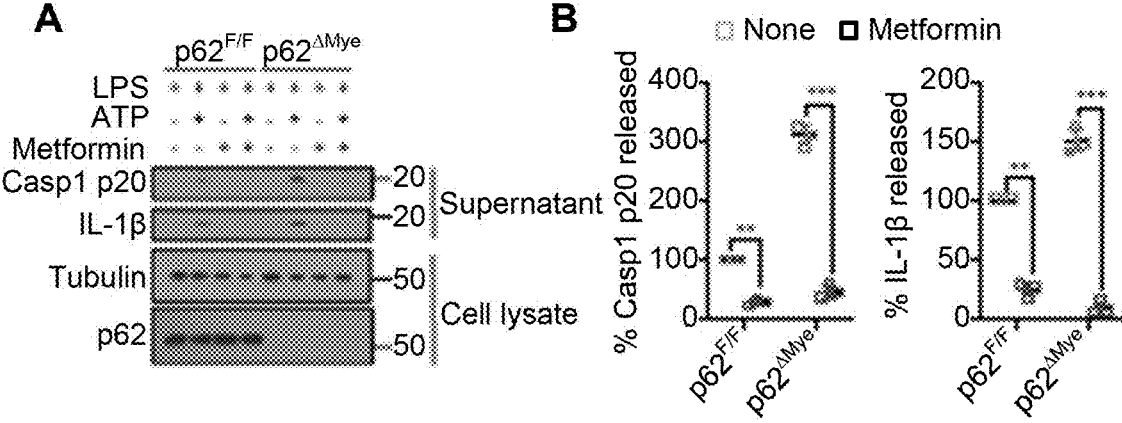
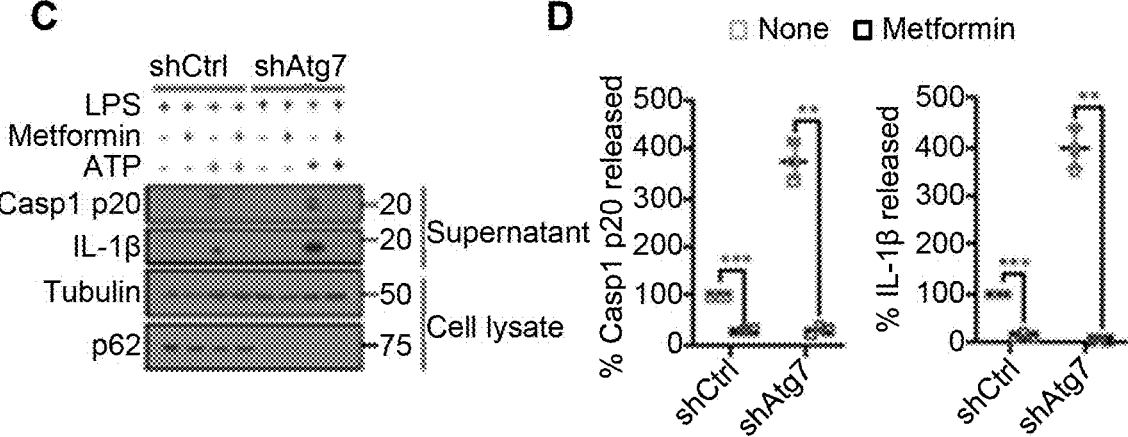
FIGS. 10A – 10D

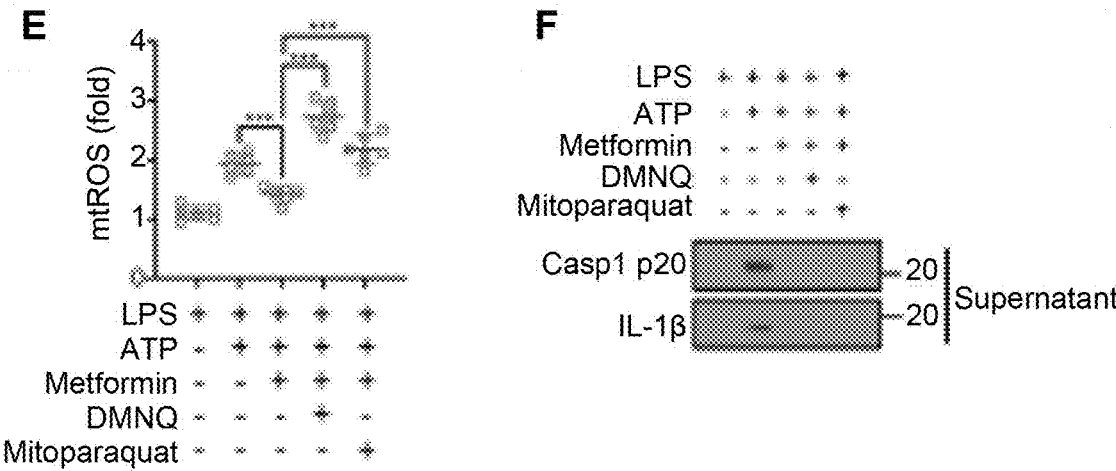
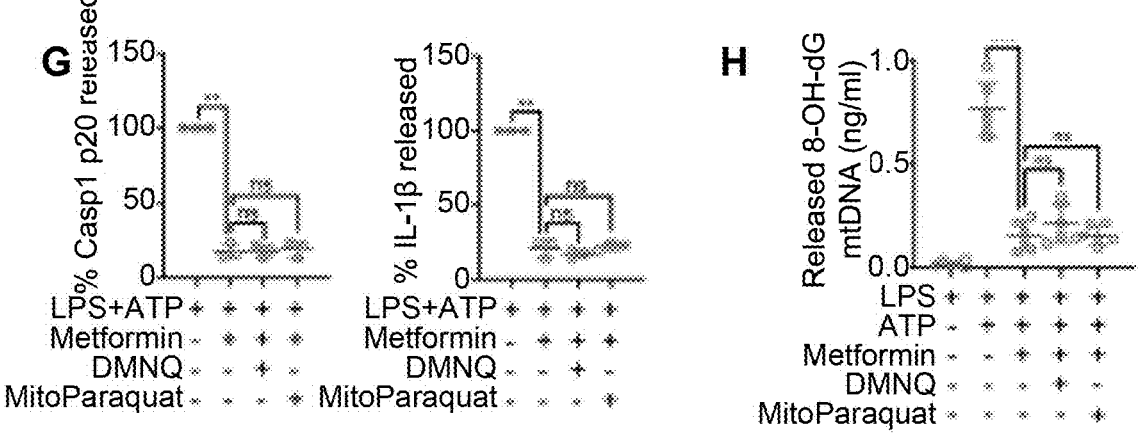
FIGS. 10E – 10H

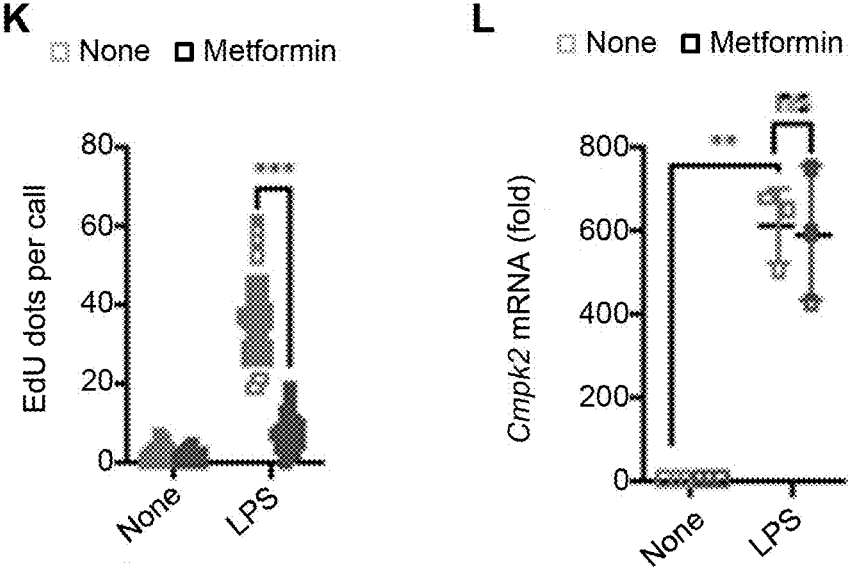
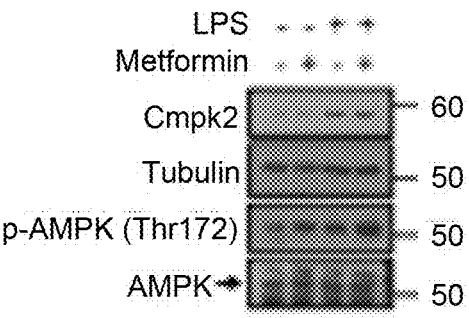
FIGS. 10K – 10M

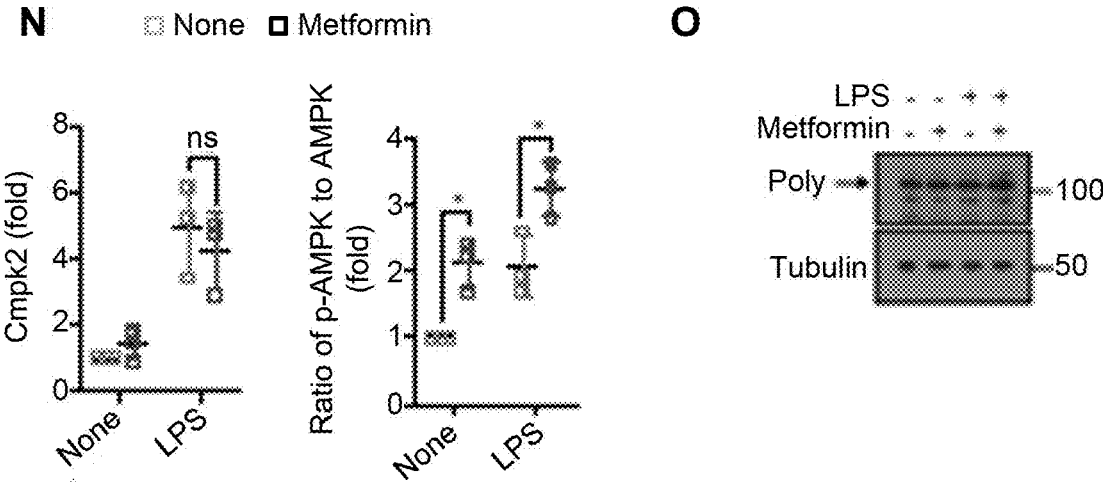
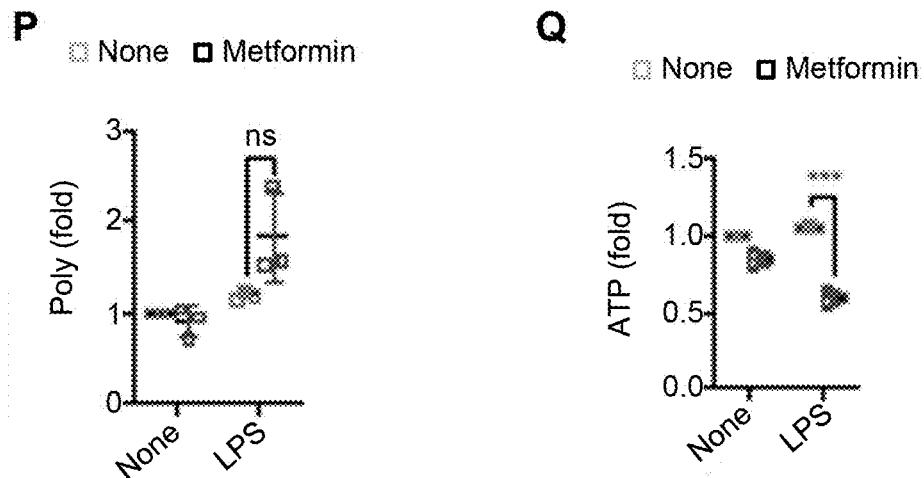
FIGS. 10N – 10Q

A

B

C

D

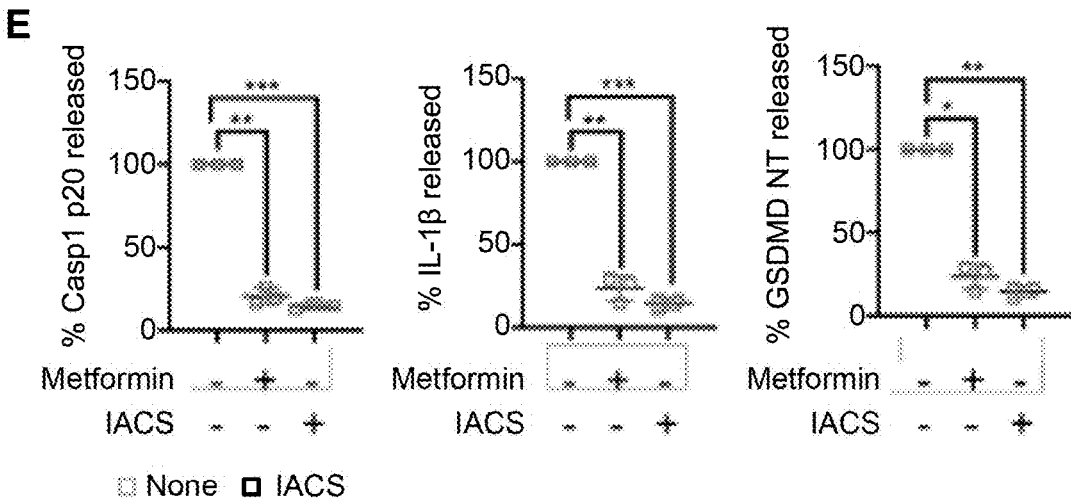
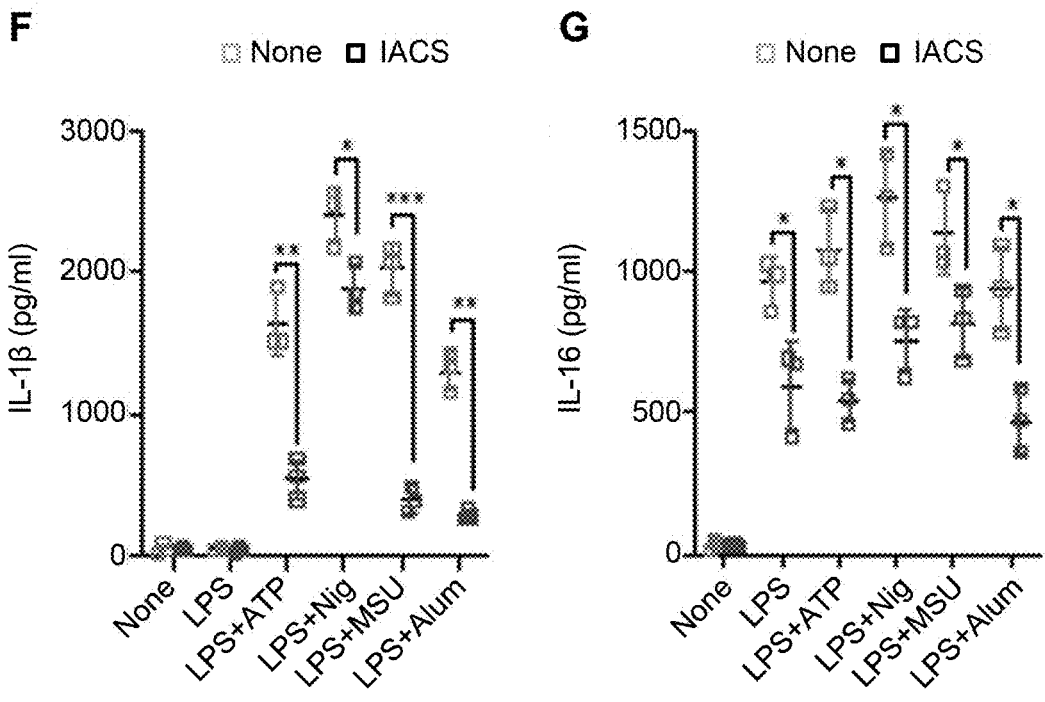
FIGS. 11E – 11G

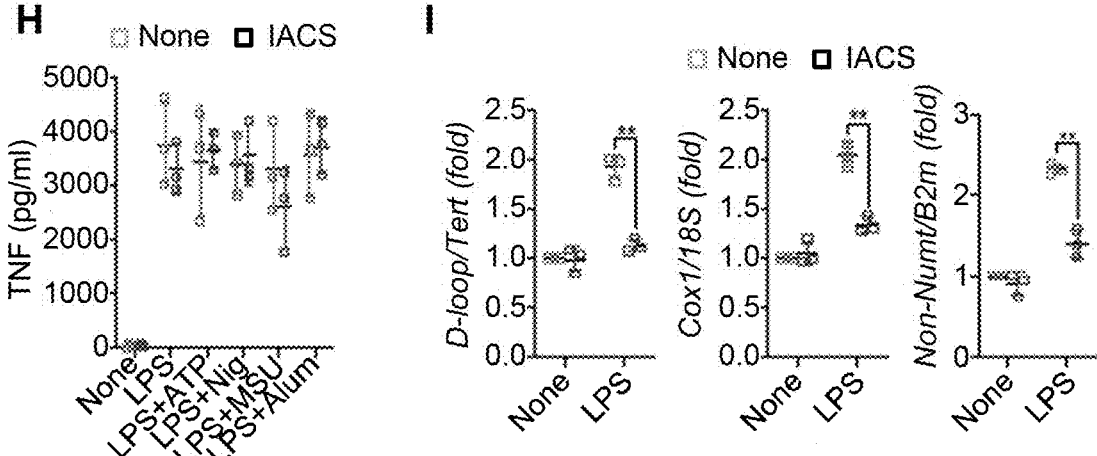
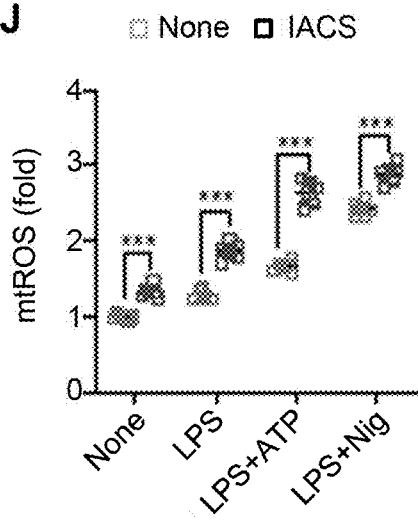
FIGS. 11H – 11J

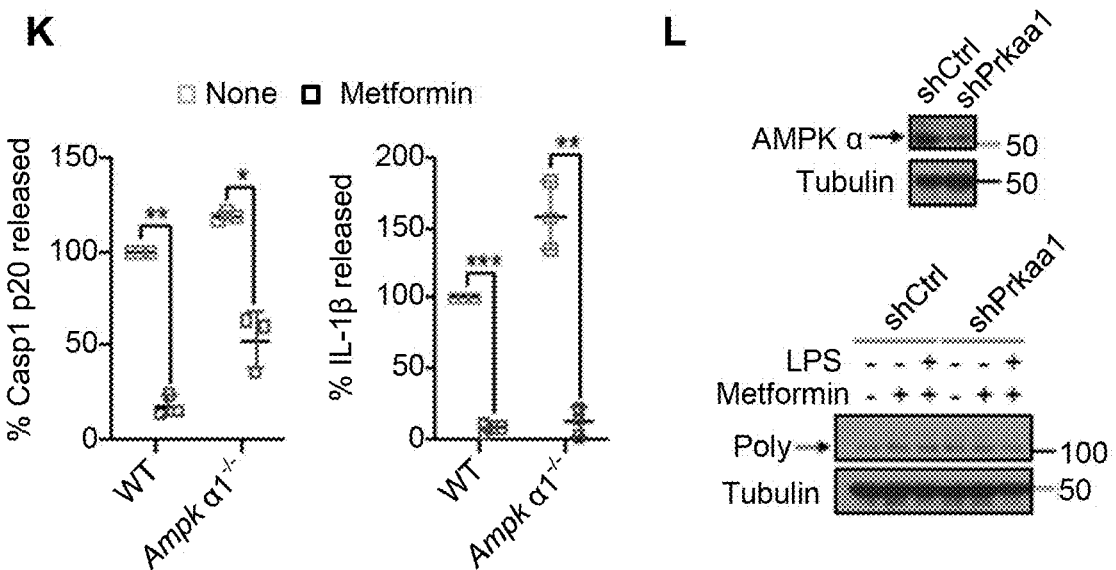
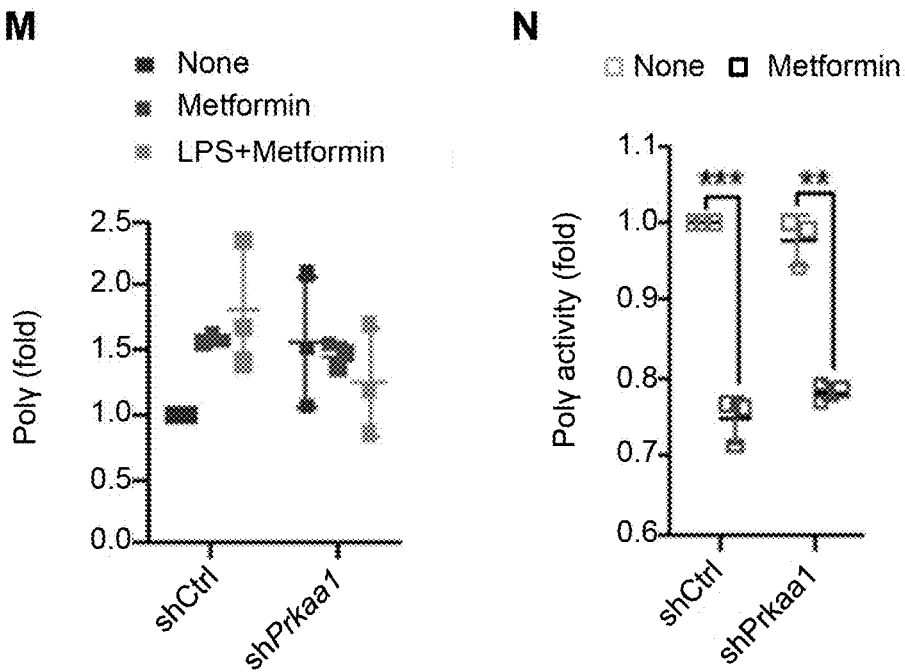
FIGS. 11K – 11N

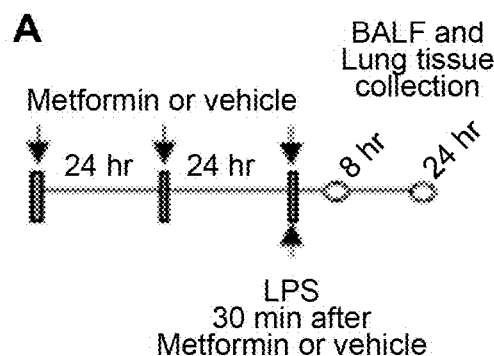
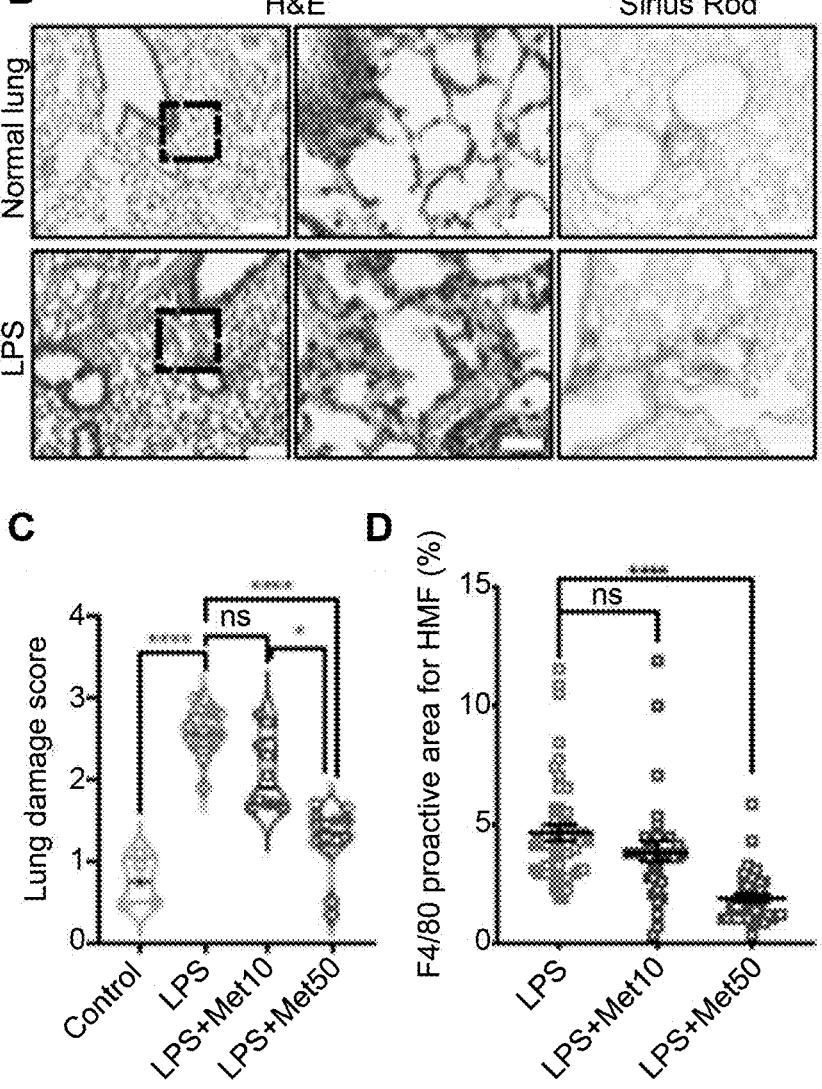
FIGS. 12A – 12D

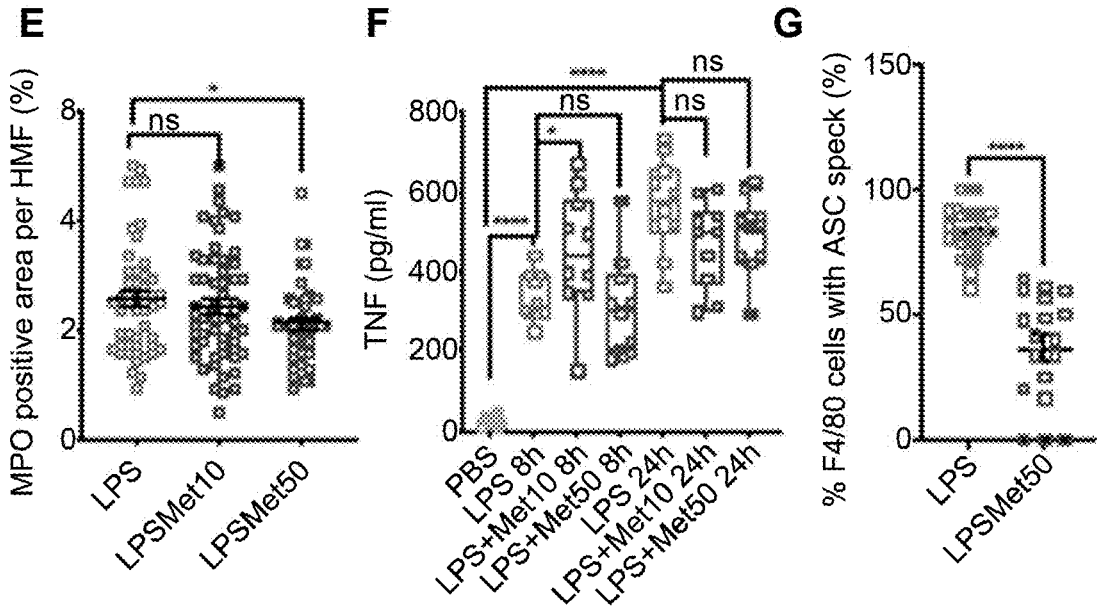
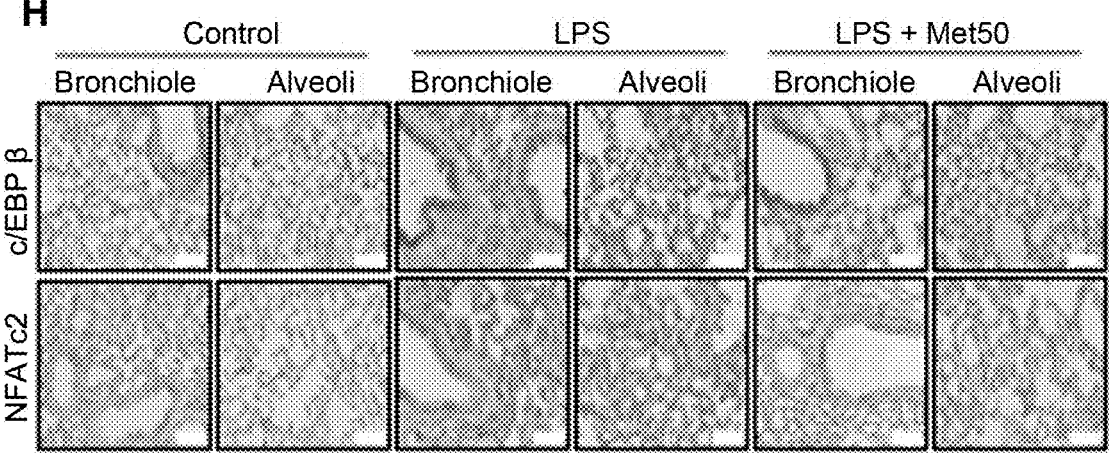
FIGS. 12E – 12H

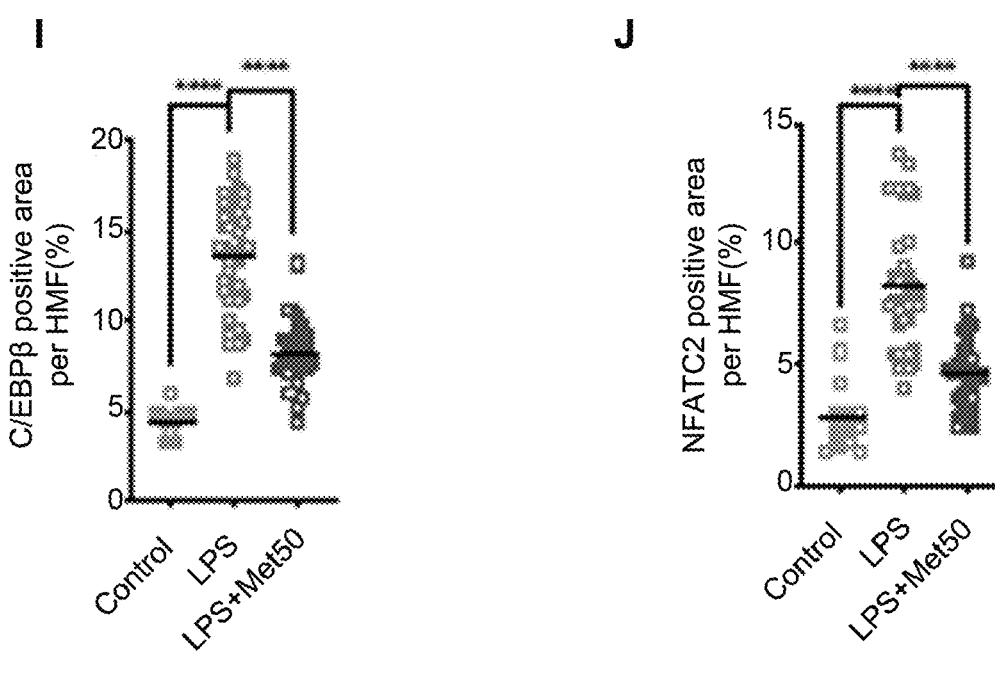
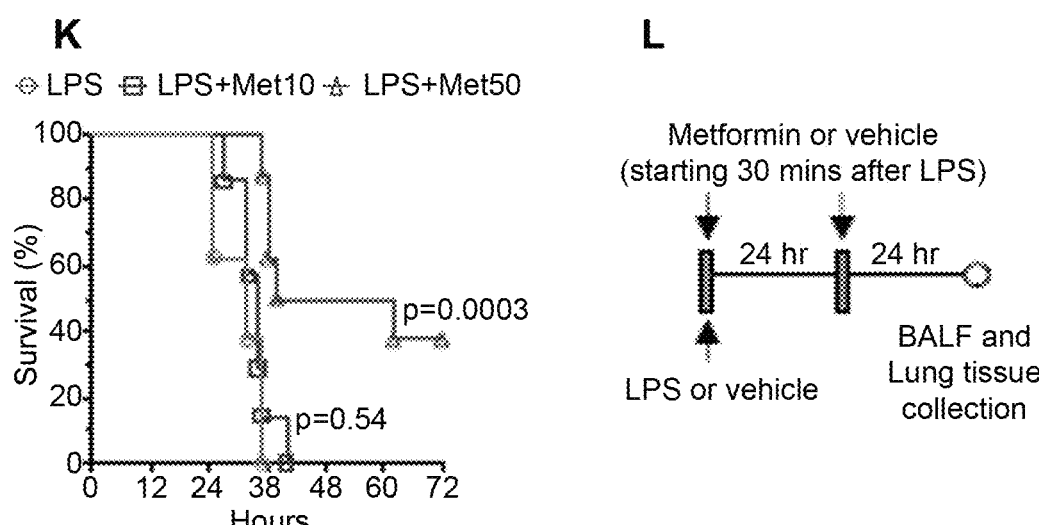
FIGS. 12I – 12L

M
Metformin solution (400 mg/
kg) or regular water
Metformin (50 mg/kg) or vehicle (i.p.)
24 hr    24 hr
Day: -2    -1    0    1
24 hr
LPS 30 min
after Metformin
or vehicle
N
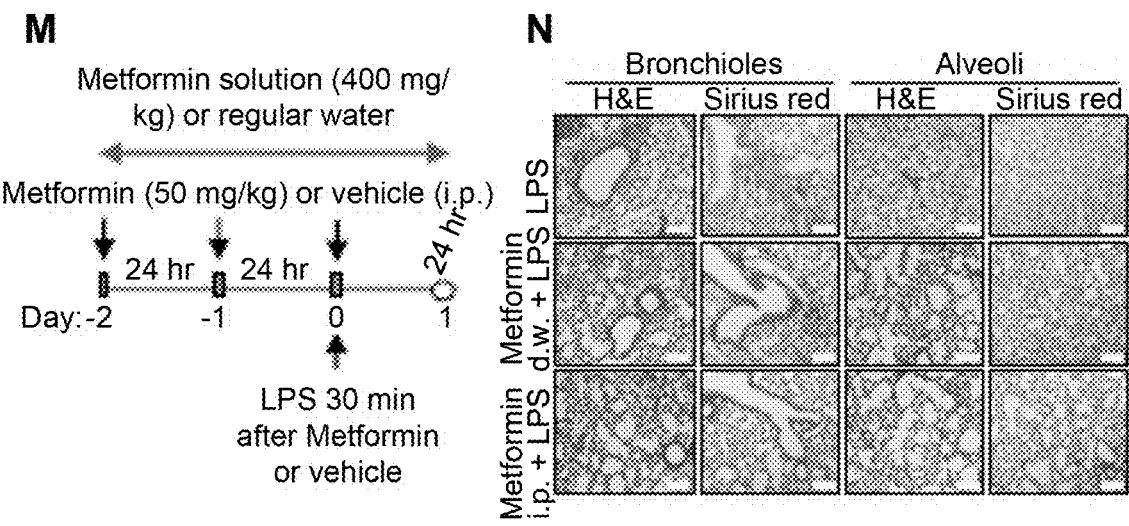
O
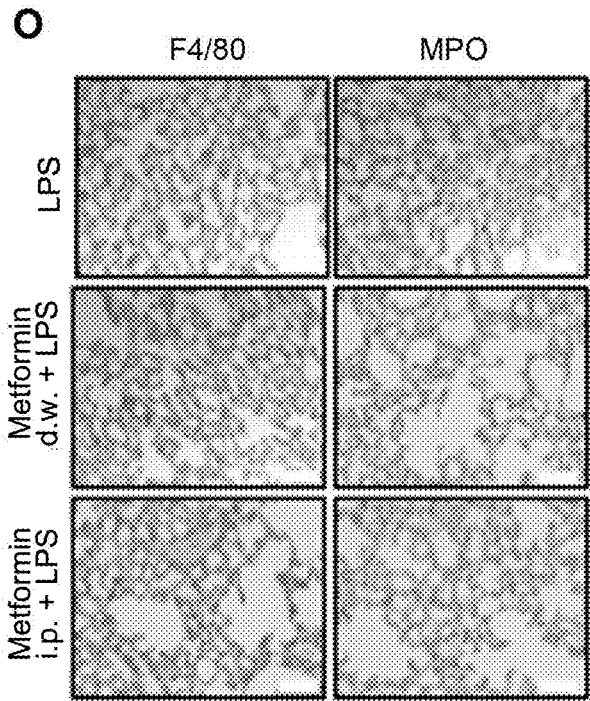
FIGS. 12M – 12O

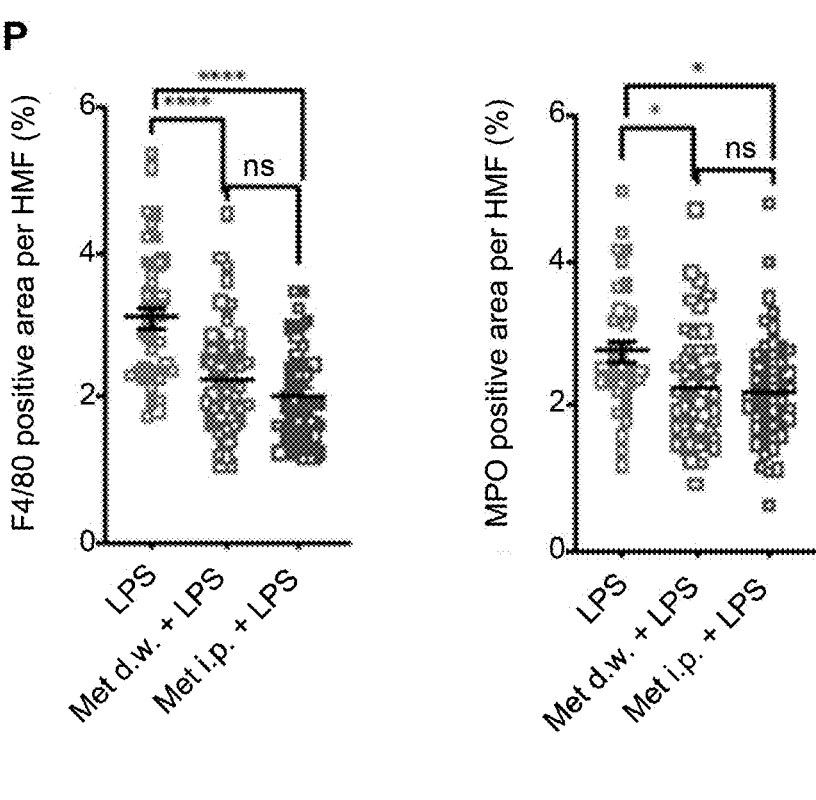
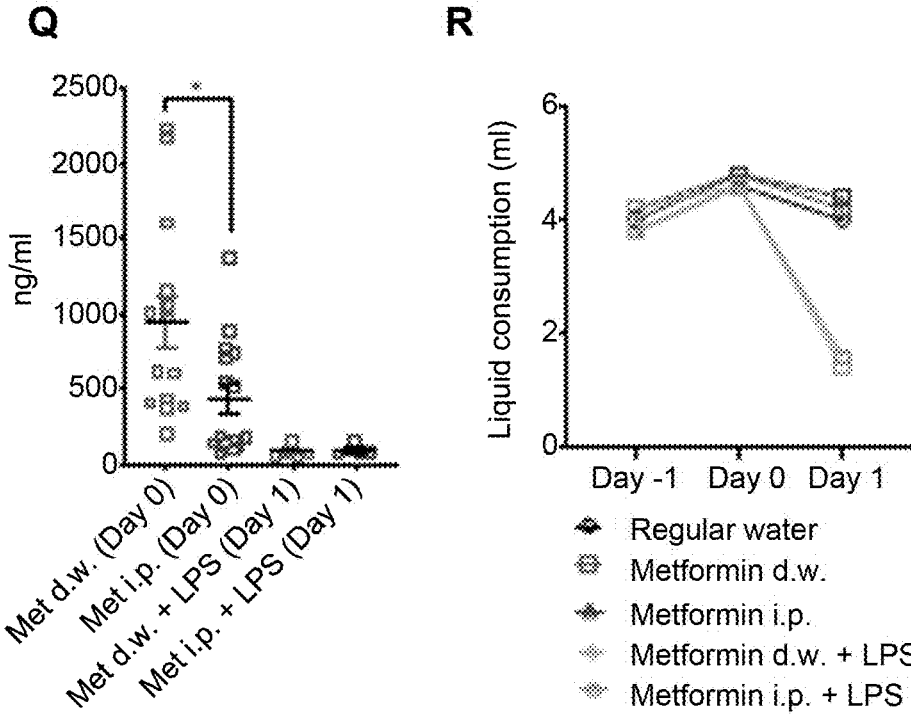
FIGS. 12P – 12R

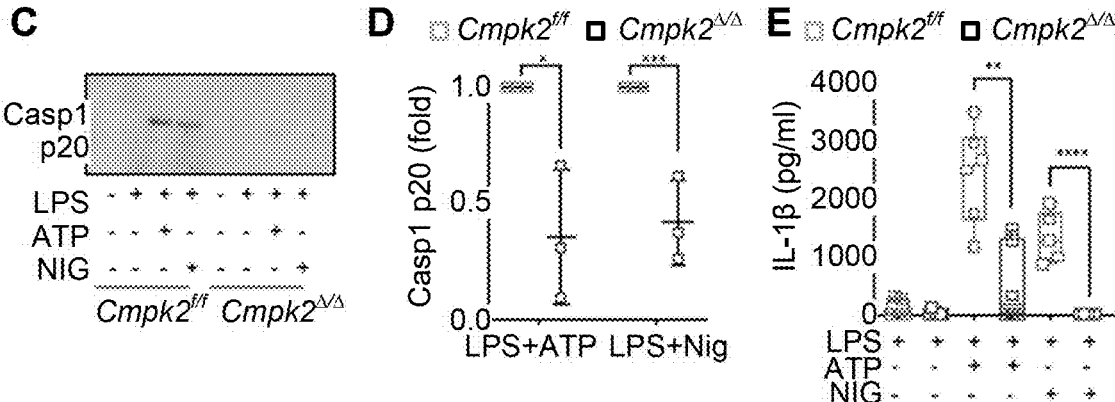
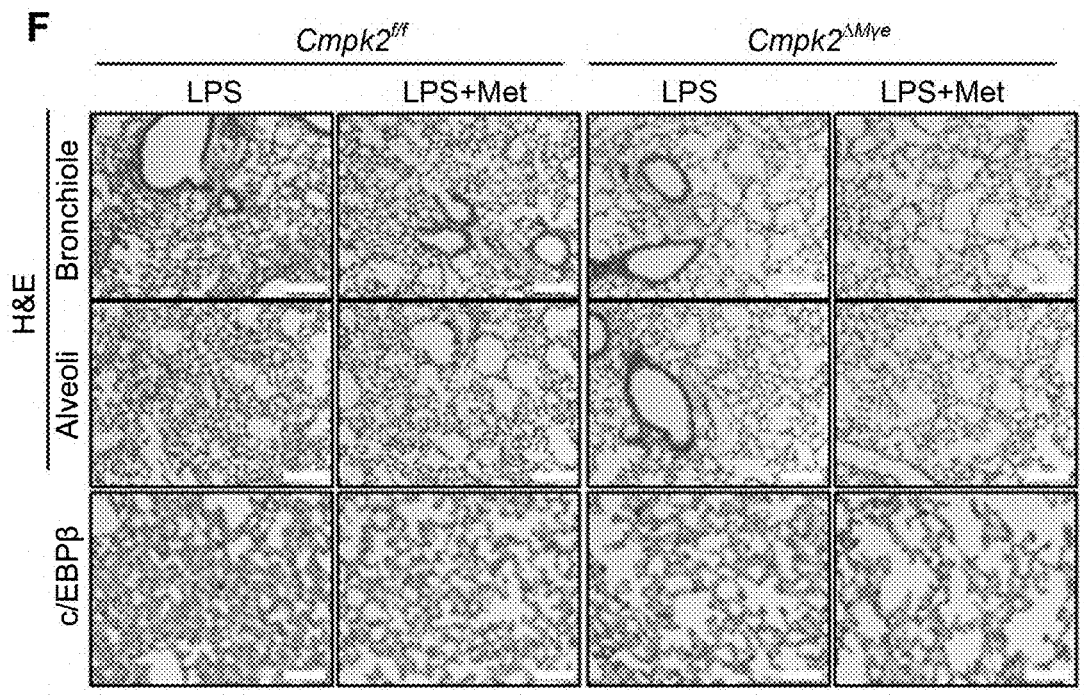
FIGS. 13C – 13F

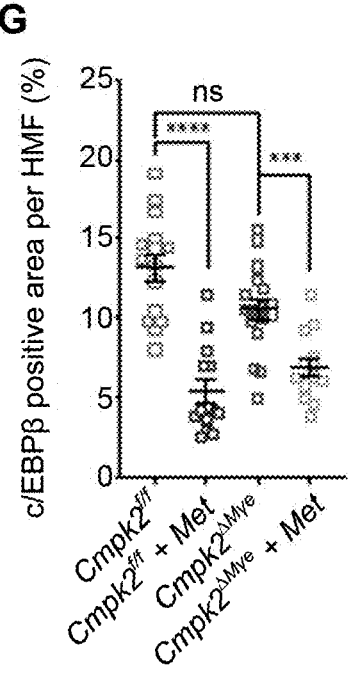
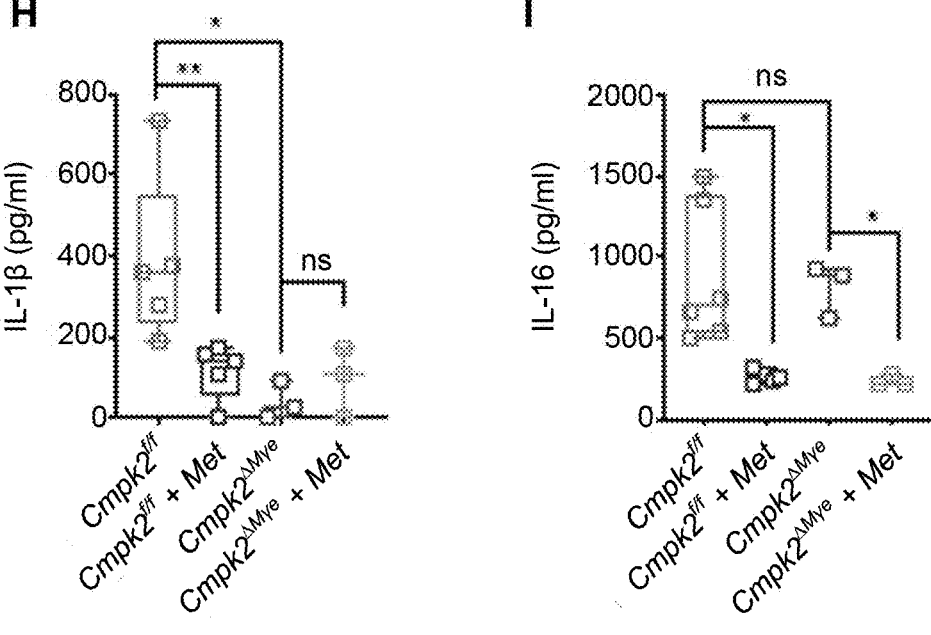
FIGS. 13G – 13I

METHODS AND COMPOSITIONS TO TREAT AND PREVENT VIRAL INFECTIONS AND ACUTE RESPIRATORY DISTRESS SYNDROME

CROSS REFERENCE TO RELATED APPLICATION

This application is a U.S. 371 National Stage Application of PCT International Application No. PCT/US2021/053038, filed Sep. 30, 2021, which claims the benefit under 35 U.S.C. § 119(e) of U.S. Provisional Application Ser. No. 63/086,445, filed Oct. 1, 2020, the contents of each of which are hereby incorporated by reference in its entirety.

STATEMENT OF GOVERNMENT SUPPORT

This invention was made with government support under Grant Nos. Superfund P42 ES010337 and AI R37AI043477 awarded by the National Institutes of Health (NIH). The government has certain rights in the invention.

BACKGROUND

The novel SARS-CoV-2 virus, the cause of COVID-19, can establish lower airway infections that culminate in acute respiratory distress syndrome (ARDS) in 20-30% of ICU patients (Tay et al., 2020). ARDS is a severe pulmonary inflammatory reaction that is also triggered by other respiratory viruses and bacteria and even physical trauma (Han and Mallampalli, 2015). During ARDS pathogenesis, innate immune cells, mainly monocytes, macrophages and neutrophils, propagate uncontrolled inflammation and tissue injury by secreting IL-1β, IL-18, IL-6 and TNF (Han and Mallampalli, 2015). Bacterially triggered ARDS is thought to be initiated on Toll like receptor (TLR) activation, but in sterile or virally-induced ARDS the inflammatory response is thought to be initiated by the NLRP3 inflammasome, which is highly expressed and activated in myeloid cells that have been primed through TLR sensing of viral RNA or the CoV spike (S) protein (Dolinay et al., 2012; Dosch et al., 2009). Following priming, the NLRP3 inflammasome, composed of the enzyme caspase-1 (Casp1), the sensorNLRP3, NEK7 and the scaffold protein ASC (Sharif et al., 2019), is activated by damage associated molecular patterns (DAMPs), e.g. ATP and uric acid (UA) microcrystals, released by injured epithelial cells (Tschopp and Schroder, 2010), and the SARS-CoV pore-forming protein viroporin 3a (Chen et al., 2019). Injured lung epithelial cells also release IL-1α, which primes airway macrophages via the same adaptors used by TLRs, MyD88 and TRIF (Cohen, 2014). Macrophage priming stimulates DNA polymerase-γ(POLγ)-mediated mitochondrial (mt) DNA synthesis, whereas ATP, UA microcrystals and other DAMPs elicit mitochondrial damage (Zhong et al., 2018). Mitochondrial damage produces reactive oxygen species (ROS) that react with newly synthesized mtDNA to generate oxidized (Ox) mtDNA, which binds cyoplasmic NLRP3 and triggers inflammasome assembly and activation (Shimada et al., 2012; Zhong et al., 2018). Of note, circulating mtDNA was suggested to serve as an inflammatory mediator that leads to distant organ damage (Grazioli and Pugin, 2018), and an early indicator of severe illness and mortality in ARDS (Han and Mallampalli, 2015), and COVID-19 (Scozzi et al., 2020). Other factors that amplify ARDS (Day et al., 2009) and COVID-19 (Gao et al., 2020; Richardson et al., 2020; Singh and Khan, 2020;

Verma et al., 2020; Yang et al., 2020a) risk and mortality are old age and co-morbidities such as type 2 diabetes mellitus (T2DM) and obesity.

Thus, a need exists in the art for a safe and effective therapy to treat these unmet medical needs. This disclosure satisfies these needs and provides related advantages as well.

SUMMARY OF THE DISCLOSURE

Two drugs used for treating hyperlipidemia and hyperglycemia, statins and metformin are found to, respectively, greatly reduce COVID-19 severity and mortality (Bramante et al., 2020; Zhang et al., 2020). In China, long-term metformin use decreased hospital mortality by 4-fold relative to other anti-diabetic drugs (Luo et al., 2020) and in a US-based study metformin reduced the odds ratio of COVID-19 death in Blacks/African Americans with T2D by 10-fold (Crouse et al., 2020). Sustained metformin administration ameliorates other age-related pathologies and extends life span and health span in model organisms (Barzilai et al., 2016), effects that are not directly related to glycemic control (Valencia et al., 2017), but may be due to metformin's anti-inflammatory properties (Barzilai et al., 2016; Marcucci et al., 2020; Pollak, 2017). Long-term use of metformin, but not other anti-diabetic drugs, also correlates with decreased age-related dementia and neurodegenerative disease incidence in elderly T2DM patients (Campbell et al., 2018; Markowicz-Piasecka et al., 2017; Shi et al., 2019). Metformin's mode of action (MOA) remains debatable, but most researchers agree that it inhibits oxidative phosphorylation and reduces ATP production through interaction with respiratory complex I (ETCCI) or other mitochondrial electron transfer chain components (Bridges et al., 2014; Pollak, 2017). By increasing ADP:ATP ratio metformin activates AMPK and inhibits mTORC1, thereby reducing hepatic glucose production (Duca et al., 2015), and enhancing autophagy, a homeostatic process that limits cell and tissue damage (Salminen and Kaarniranta, 2012). Autophagy/mitophagy curtails inflammation in part by eliminating damage mitochondria and limiting NLRP3 inflammasome activation (Sanchez-Lopez et al., 2019; Zhong et al., 2016). Metformin was reported to reduce NLRP3 inflammasome expression or activation in diabetic macrophages and several non-myeloid cell types in an AMPK dependent manner, but downstream mediators linking AMPK to the inflammasome, including mitophagy, and their role in the response to metformin was not investigated (Lee et al., 2013; Li et al., 2016; Yang et al., 2019). AMPK inhibits IKK-mediated NF-κB activation in vascular endothelial cells and cardiomyocytes but the underlying mechanism and its relationship to NLRP3 inflammasome priming remain obscure (Hattori et al., 2006; Vaez et al., 2016). Moreover, metformin was also reported to inhibit NF-κB and cytokine induction in glia independently of AMPK (Labuzek et al., 2010), and ameliorate air-pollution induced thrombosis and IL-6 production through ETCCI inhibition in alveolar macrophages (Soberanes et al., 2019). Here Applicants show that short-term metformin treatment of non-diabetic mice exerts potent anti-inflammatory effects in two preclinical models, including LPS-induced ARDS. In vitro studies with macrophages show that metformin's anti-inflammatory activity correlates with ETCCI inhibition and reduced ATP production. The latter abrogates POLγ-dependent mtDNA synthesis and Ox-mtDNA production, thereby inhibiting NLRP3 inflammasome activation. Applicants provide methods comprising administration of metformin, an analog or derivative thereof alone or together with other drugs, to reduce disease severity and ARDS incidence in patients infected with SARS-CoV-2 or other respiratory viruses.

Thus, in one aspect provided herein is a method of preventing, treating or reducing the severity of acute respiratory distress syndrome (ARDS) in a subject at risk for contracting ARDS and infected with a coronavirus. The method comprises, or consists essentially of, or yet further consists of administering to the subject metformin, an analog or derivative of metformin, thereby treating, preventing, or reducing the severity of ARDS in the subject.

In one embodiment, the subject is suffering from a comorbidity, non-limiting examples of such include pre-diabetes, type-II diabetes, obesity, or hypertension. In some embodiments, the coronavirus comprises or is SARS-CoV-2.

In yet another aspect, a composition is provided. The composition comprises, or consists essentially of, or yet further consists of an effective amount of metformin or an analog or derivative of metformin. In one aspect the composition is used for preventing, treating, or reducing disease severity in a subject affected with a coronavirus or ARDS incidence in a subject infected with coronavirus.

In yet another aspect, a kit is provided. The kit comprises, or consists essentially of, or yet further consists of metform, an analog or derivative thereof. In one embodiment the kit further comprises, or consists essentially of, or yet further consists of instruction for the use of preventing, treating, reducing disease severity or ARDS incidence in a subject infected with coronavirus, e.g., SARS-Cov-2. In a further aspect, the subject is a member of a population at risk for contracting ARDS.

BRIEF DESCRIPTION OF THE FIGURES

(FIG. 1B) IB analysis of p62, DRP1, and VDAC in mitochondria from BMDM pretreated –/+ metformin, primed with LPS, and challenged with ATP (4 mM, 1 h). (FIG. 1C) Q-PCR quantitation of Il1b, Il6 and Il10 mRNAs before or after LPS stimulation –/+ metformin pre-treatment (n=3). (FIG. 1D) p65, C/EBPb or NFATc1-4 recruitments to the Il1 and Il6 promoters in BMDM before or after LPS stimulation was analyzed by ChIP-qPCR assay (n=3-7). (FIG. 1E) IB analysis of p38 MAPK and JNK phosphorylation (left) and quantitation of Il6 mRNA(top) and IL-6 secretion (bottom) from BMDM pretreated with metformin, SB202190 (10 mM) or SP600125 (40 mM) for 16 h and stimulated with LPS for 30 min. All IB show one representative out of 3. Results in (FIGS. 1C-1E) are averages ±SD. *p<0.05; p<0.01; *p<0.001. Two-sided unpaired t test. See also FIG. 8.

(FIG. 2B) IB analysis of cleaved caspase-1 (Casp1 p20), mature IL-1b and cleaved GSDMD (GSDMD NT [p30]) in culture supernatants, and tubulin in lysates of BMDM that were pretreated –/+ metformin, primed with LPS, and challenged with inflammasome activators (Nig-nigericin, 10 mM, 1 h; MSU, 600 mg/mL, 6 h). (FIG. 2C) Representative fluorescent microscopy images of BMDM co-stained for Tom20 and ASC before or after LPS (100 ng/mL, 4 h) priming followed by ATP (4 mM, 1 h) ornigericin (10 mM, 1 h), –/+ metformin (0.5 mM, 16 h) pre-treatment. DAPI stains nuclei. Arrows indicate ASC specks. Scale bars, 10 mm (n=3). (FIG. 2D) Percentages of cells shown in (FIG. 2C) with ASC specks. n=150 cells per group from 3 independent experiments, magnification 3 100. (FIG. 2E and FIG. 2F) Peritoneal IL-1b (FIG. 2E) and IL-6 (FIG. 2F) in mice treated with different doses of metformin (0, 10, and 50 mg/kg) 30 min prior to i.p. alum (700 mg) injection (n=9 mice per group). All blots show one representative IB out of 3. Results in (FIG. 2D) are averages ±SD and in (FIG. 2E) averages ±SEM.*p<0.05; p <0.01; *p<0.001; ****p<0.0001; ns, not significant. Two-sided unpaired t test. See also FIG. 9.

(FIG. 3B) Relative mtROS amounts measured by MitoSOX staining of BMDM treated as above. (FIG. 3C) Relative total mtDNA amounts in LPS-primed BMDM–/+ metformin pre-treatment. Shown are the ratio of D-loopmtDNA to Tertnuclear (n)DNA, Cox1 mtDNA to 18SnDNA or mtDNA that is not inserted into nuclear DNA (non-NUMT) to B2m nDNA. (FIG. 3D) 8-OH-dG amounts in cytosolic mtDNA of LPS primed BMDM stimulated with ATP ornigericin (Nig) –/+ metformin pre-treatment were measured by ELISA. (FIG. 3E) Lysates of LPS-primed BMDM –/+ metformin pretreatment were divided into two aliquots. One aliquot was used to measure POLg activity without exogenous ATP and the other was supplemented with 10 mM ATP prior to measuringPOLg activity. Results are averages ±SD (n=3). *p<0.05; **p<0.01; ns, not significant. Two-sided unpaired t test. See also FIG. 10.

(FIG. 4B) Relative total mtDNA amounts in LPS (200 ng/mL, 4 h)-primed wild type (WT) or Ndufs4/BMDM. The ratio of D-loop mtDNA to Tert nDNA, Cox1 mtDNA to 18S nDNA, or mtDNA that is not inserted into nuclear DNA (non-NUMT) to B2m nDNA is shown. (FIG. 4C) IB analysis of AMPKa (left), Casp1 p20 and mature IL-1b (right) in culture supernatants and lysates of LPS-primed wild type (W) or Ampka1/(K) BMDM stimulated –/+ ATP. (FIG. 4D) Relative total mtDNA amounts in LPS-primed shCtrl- and shPrkaa1-transfected BMDM. The ratio of D-loop mtDNA to Tert nDNA, Cox1 mtDNA to 18S nDNA, or mtDNA that is not inserted into nuclear DNA (non-NUMT) to B2m nDNA is shown. All IB show one representative out of 3. Results are averages ±SD (n=3). *p<0.05; **p<0.01. Two-sided unpaired t test. See also FIG. 11.

(FIG. 5B) Lung sections from above mice were stained with F4/80 and MPO antibodies. Scale bar, 50 mm. n=4 mice per group. 10-12 images per mouse were evaluated. (FIG. 5C and FIG. 5D) IL-1b (FIG. 5C) and IL-6 (FIG. 5D) concentrations in BALF from above mice were measured by ELISA. n=10 mice per group. (FIG. 5E) F4/80 and ASC immunostaining of paraffin-embedded lung tissue from above mice. DAPI stains nuclei. Scale bar, 7.5 mm. n=4 mice per group. (FIG. 5F) H & E and Sirius red staining of lung tissue from mice that were left untreated or treated with 50 mg/kg metformin daily starting 30 min after 5 mg/kg LPS challenge. Tissue was collected 48 h after LPS administration. Scale bar, 100 mm; n=5 mice per group. 10-12 images per mouse were evaluated. (FIG. 5G) F4/80 and MPO staining in lung sections from mice in (FIG. 5F). Scale bar, 50 mm. n=5 mice per group. 10-12 images per mouse were evaluated. (FIG. 5H) IL-1b concentration in BALF from mice in (FIG. 5F) were measured by ELISA. n=5 mice per group. p<0.01; **p<0.001; ns, not significant. Unpaired t test; Mann-Whitney test. See also FIG. 11.

(FIG. 6B) F4/80 and MPO staining in lung sections from mice in (FIG. 6A). Scale bar, 50 mm. n=5 mice per group. 10-12 images per mouse were evaluated. (FIG. 6C and FIG. 6D) Area (in %) occupied by F4/80 (FIG. 6C), and MPO (FIG. 6D) staining, in lung sections from (FIG. 6B). Averages ±SEM; n=5 mice per group. 10-12 HMF per group evaluated. F4/80, ASC and DAPI immunostaining of lung tissue from mice above (FIG. 6E). Amount of F4/80 positive cells stained with ASC (FIG. 6F). IL-1b concentration (pg/ml) from mice in (FIG. 6A) were measured by ELISA (FIG. 6G). IL-6 concentration (pg/ml) from mice in (FIG. 6A) measured by ELISA (FIG. 6H).

(FIG. 7A and FIG. 7C) Quantification of macrophages (FIG. 7B) (CD68+) and cells with ASC specks (FIG. 7C) normalized tonucleiin above lung sections. *p<0.05. Unpaired ttest; MannWhitney test. (FIG. 7D) Lung inflammation score in SARS-CoV-2-infected hACE2 Tg mice infected as indicated in STAR Methods. The scores were averaged and are shown as average ±SEM n=4 mice. *p<0.05. All groups were compared to each other using ANOVA Kruskal-Wallis test. (FIG. 7E) H&E staining of lung tissue from hACE2 Tg mice treated as in (FIG. 7D). Scale bar, 200 mm. n=4 mice per group. 10-12 images per mouse were evaluated. (FIG. 7F) Lung sections from mice in (FIG. 7E) were stained with F4/80, MPO and C/EBPb antibodies. (FIG. 7G) Almost no macrophages with ACS specks were found in metformin treated lungs. Scale bar, 100 mm for F4/80, MPO, and C/EBPb, and 50 mm for highlighted areas. n=4 mice per group. 10-12 images per mouse were evaluated.

(FIG. 8A) Relative nuclear p65 to total p65 amounts by BMDM treated as in FIG. 1A (n=2). (FIG. 8H) Q-PCR quantitation of Il10 mRNA in shCtrl and shPrkaa1 BMDM treated as in (FIG. 8E) (n=3). (FIG. 8I-FIG. 8J) IL-6 (FIG. 8I) and TNF (FIG. 8J) secretion by LPS (100 ng/ml, 4 hrs)-primed BMDM challenged with different NLRP3 activators as indicated, –/+ metformin (0.5 mM, 16 hrs) (n=3). (FIG. 8K) IL-6, TNF and MCP1 secretion by GM-CSF differentiated human macrophages pretreated with increasing concentrations of metformin for 2 hrs and stimulated with IFNγ (20 ng/ml) and LPS (100 ng/ml) for 24 hrs. Results are averages ±SD (n=2 donors). (FIG. 8O) Relative amounts of phosphorylated p38 MAPK and JNK expression in BMDM treated as in FIG. 9E (n=3). Results in (FIG. 8A, FIG. 8B, FIG. 8D-FIG. 8J, FIG. 8L, FIG. 8N and FIG. 8O) are averages ±SD. *p<0.05; p<0.01, *p<0.001;ns, not significant. Two-sided unpaired t-test.

FIGS. 9A-9J: Metformin inhibits NLRP3 inflammasome activation, related to FIG. 2 (FIG. 9A) Relative amounts of NLRP3 inflammasome components of BMDM as treated in FIG. 2A (n=3). (FIG. 9B) Relative Casp1 p20, IL-1β and GSDMD NT secretion of BMDM treated as in FIG. 2B (n=3). (FIG. 9C) Casp1 activity in LPS (100 ng/ml, 4 hrs)-primed BMDM stimulated with ATP (4 mM, 1 hr) or nigericin (10 µM, 1 hr) –/+ metformin (0.5 mM, 16 hrs) pre-treatment was measured by FAM-FLICA® Caspase-1 (YVAD) Assay Kit (n=3). (FIG. 9D) IL-1β secretion by LPS (100 ng/ml, 4 hrs)-primed BMDM challenged with different NLRP3 activators as indicated, –/+ metformin (0.5 mM, 16 hrs) pre-treatment (n=3). (FIGS. 9E-9F) Active Casp1 measured by Caspase I FLICA dye (660-YVAD-FMK) staining and analyzed by flow cytometry (FIG. 9E) and IL-1β secretion measured by ELISA (FIG. 9F) in GM-CSF differentiated human macrophages LPS (20 ng/ml, 3 hrs)-primed BMDM stimulated with ATP (2 mM, 30 min) –/+ metformin (0.5 mM, 16 hrs) pre-treatment. Results are averages ±SD (n=3 different donors, Dn1-3). p<0.01; *p<0.005. Two-way ANOVA, Sidak's multiple comparison test. FIGS. 9G-9H) Casp1 p20 (FIG. 9G) and IL-1β (FIG. 9H) release by mouse microglia primed with LPS (100 ng/ml, 4 h) and challenged with different NLRP3 activators as indicated, –/+ metformin (0.5 mM, 16 hrs) pre-treatment, were determined by IB (FIG. 9G) or ELISA (FIG. 9H). (FIG. 9G) shows representative IB (top) and relative Casp1 p20 secretion (bottom) as averages ±SD (n=3). p<0.01; *p<0.005. Two-sided unpaired t-test. (FIG. 9H) shows averages ±SEM (n=12). **p<0.0001. Two way ANOVA and Sidak's multiple comparison post-hoc test. (FIG. 9I) LDH release by LPS (100 ng/ml, 4 hrs)-primed BMDM stimulated with the indicated NLRP3 agonists, –/+ metformin (0.5 mM, 16 hrs) pre-treatment (n=3). (FIG. 9J) Peritoneal TNF in mice treated with 10 or 50 mg/kg metformin 30 min prior to i.p. alum (700 mg) injection (n=9 mice per group). Peritoneal fluid was collected 4 hrs after alum injection. Results are averages ±SEM **p<0.0001; ns, not significant. Two-sided unpaired t-test. Results in (A-D, G and I) are averages ±SD. *p<0.05; p<0.01; *p<0.001; ns, not significant. Two-sided unpaired t-test.

Figure 10I:
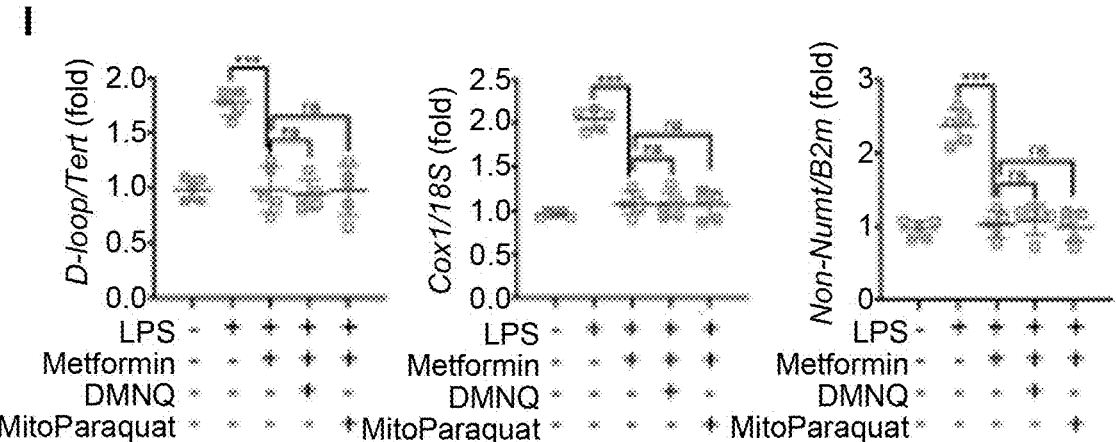

FIGS. 10A-10Q: Metformin inhibits NLRP3 inflammasome activation independently of mitophagy, related to FIG. 3 (FIG. 10A) IB analysis of Casp1 p20 and IL-1β in culture supernatants, and p62 and tubulin in cell lysates of LPS (100 ng/ml, 4 hrs)-primed p62$^{F/F}$ or p62$^{ΔMye}$ BMDM stimulated with ATP (4 mM, 1 hr), –/+ metformin (0.5 mM, 16 hrs) pre-treatment. One representative IB out of 3 is shown. (FIG. 10B) Quantitation of above results, averages ±SD (n=3). (FIG. 10C) IB analysis of Casp-1 p20 and IL-1β in culture supernatants and ATG7 and tubulin in cell lysates of LPS-primed control (shCtrl) or ATG7-deficient (shAtg7) iBMDM stimulated with ATP (4 mM, 1 hr) –/+ metformin (0.5 mM, 16 hrs) pre-treatment. One representative IB out of 3 is shown. (FIG. 10D) Quantitation of IB in (FIG. 10C), averages ±SD (n=3). (FIG. 10E) Relative mtROS amounts measured by MitoSOX staining of LPS (100 ng/ml, 4 hrs)-primed BMDM challenged with ATP (4 mM, 1 hr) –/+ metformin (0.5 mM, 16 hrs), DMNQ (20 μM, 16 hrs), or MitoParaquat (5 μM, 1 hr) pretreatment (n=6). (FIG. 10F) IB analysis of Casp1 p20 and mature IL-1β in culture supernatants, of BMDM treated as above. One representative IB out of 3 is shown. (FIG. 10G) Quantitation of IB in (FIG. 10F), averages ±SD (n=3). (FIG. 10H) 8-OH-dG amounts in cytosolic mtDNA of BMDM treated as above (n=6). (FIG. 10I) Relative total mtDNA amounts in LPS (200 ng/ml, 4 hrs)-primed BMDM treated –/+ metformin (0.5 mM, 16 hrs), DMNQ (20 μM, 16 hrs), or MitoParaquat (5 μM, 1 hr) pretreatment. Shown are the ratios of D-loop mtDNA to Tert nuclear (n) DNA, Cox1 mtDNA to 18S nDNA, or mtDNA that is not inserted into nuclear DNA (non-NUMT) to B2m nDNA. Results are averages ±SD (n=5). (FIG. 10J-FIG. 10K) Representative fluorescent microscopy images (FIG. 10J) and quantification (FIG. 10K) of EdU labelled BMDM that were co-stained for Atp5b and DAPI before and after stimulation with LPS (1 ug/ml, 4 hrs), –/+ metformin (0.5 mM, 16 hrs) pre-treatment. Scale bars, 10 μm and 2 μm. (FIG. 10K) shows results as average ±SD (n=30 HMF per treatment in 3 independent experiments). (FIG. 10L) Q-PCR quantitation of Cmpk2 mRNA in BMDM treated with LPS (100 ng/ml, 4 hrs) –/+ metformin (0.5 mM, 16 hrs) (n=3). (FIG. 10M-FIG. 10N) IB analysis of CMPK2 expression and AMPK phosphorylation in LPS (100 ng/ml, 4 hrs)-primed BMDMs –/+ metformin (0.5 mM, 16 hrs) pre-treatment. (FIG. 10M) shows representative blot. (FIG. 10N) shows quantitation of above results, averages ±SD (n=3). (FIG. 10O-FIG. 10P) IB analysis of Polγ expression in BMDM treated as indicated. (FIG. 10O) shows one representative blot and (FIG. 10P) shows quantitation, averages ±SD (n=3). (FIG. 10Q) Relative cellular ATP amounts in LPS (100 ng/ml, 4 hrs)-primed BMDMs –/+ metformin (0.5 mM, 16 hrs) pre-treatment (n=3). Results in (FIG. 10B, FIG. 10D, FIG. 10E, FIG. 10G-FIG. 10I, FIG. 10K, FIG. 10L, FIG. 10N, FIG. 10P and FIG. 10Q) are averages +SD. *p<0.05; p<0.01; *p<0.001; ns, not significant. Two-sided unpaired t-test.

8

Figure 11A:
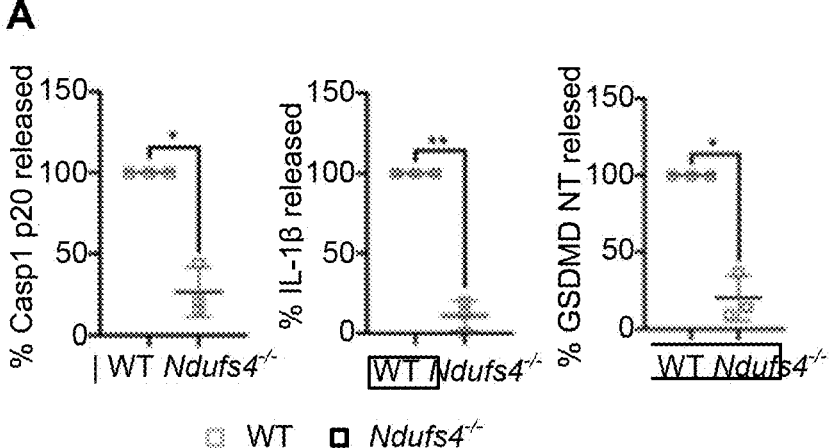

FIGS. 11A-11N: Metformin inhibits NLRP3 inflammasome activation independently of AMPK, related to FIG. 4. (FIG. 11A) Relative Casp1 p20, IL-1β and GSDMD NT release by LPS (100 ng/ml, 4 hrs)-primed wild type (WT) or Ndufs4–/–BMDM stimulated with ATP (4 mM, 1 hr), shown as in FIG. 4A (n=3). (FIG. 11B, (FIG. 11C) IB analysis of Casp1 p20 and mature IL-1β in culture supernatants of LPS (100 ng/ml, 4 hrs)-primed wild type (W) or Ndufs4–/–(K) BMDM stimulated with ATP (4 mM, 1 hr), –/+ metformin (0.5 mM, 16 hrs) pretreatment. Representative IB of 3 independent experiments. (FIG. 11C) Quantitation of above results, averages ±SD (n=3). (FIG. 11D, FIG. 11E) IB analysis of Casp1 p20, mature IL-1β and cleaved gasdermin D (GSDMD NT (p30)) in culture supernatants, and tubulin in lysates of BMDM that were LPS (100 ng/ml, 4 hrs)-primed and ATP (4 mM, 1 hr) challenged as indicated, –/+ metformin (0.5 mM, 16 hrs) or IACS-010759 (20 μM, 16 hrs) pretreatment. (FIG. 11E) Quantitation of above results, averages ±SD (n=3). (FIG. 11F-FIG. 11H) IL-1β (FIG. 11F), IL-6 (FIG. 11G) and TNF (FIG. 11H) secretion by BMDM pretreated –/+ IACS-010759 (20 μM, 16 hrs) that were left unstimulated or LPS (100 ng/ml, 4 hrs)-primed and challenged with the indicated NLRP3 activators (n=3). (FIG. 11I) Relative total mtDNA amounts in LPS (200 ng/ml, 4 hrs)-primed BMDM –/+ IACS-010759 (20 sM, 16 hrs) pretreatment. Shown are the ratios of D-loop mtDNA to Tert nuclear (n) DNA, Cox1 mtDNA to 18S nDNA, or mtDNA that is not inserted into nuclear DNA (non-NUMT) to B2m nDNA (n=3). (FIG. 11J) Relative mtROS amounts measured by MitoSOX staining of BMDM –/+ IACS-010759 (20 μM, 16 hrs) pretreatment that were left unstimulated or LPS (100 ng/ml, 4 hrs)-primed and challenged with the indicated NLRP3 activators (n=6). (FIG. 11K) Relative Casp1 p20 and IL-1β release by LPS (100 ng/ml, 4 hrs)-primed wild type (WT) or Ampkα1$^{-/-}$ BMDM stimulated –/+ ATP (4 mM, 1 hr), shown as in FIG. 4C (n=3). (FIG. 11L, FIG. 11M) IB analysis of AMPKα1/2 (top), POLγ (bottom) and tubulin in lysates of shCtrl and shPrkaa1 treated BMDM that were stimulated with LPS (100 ng/ml, 4 hrs) –/+ metformin (0.5 mM, 16 hrs) pretreatment. The top panel demonstrates knockdown efficiency. (FIG. 11M) Quantitation of POLγ expression, averages ±SD (n=3). (FIG. 11N) Polγ activity in lysates of LPS (100 ng/ml, 4 hrs)-primed shCtrl and shPrkaa1 BMDM with or without metformin (0.5 mM, 16 hrs) pretreatment (n=3). Results in (FIG. 11A, FIG. 11C, FIG. 11E-FIG. 11K, and FIG. 11M-FIG. 11N) are averages ±SD. *p<0.05; p<0.01; *p<0.001, ns, not significant. Two-sided unpaired t-test.

Figures 5A, 5B:
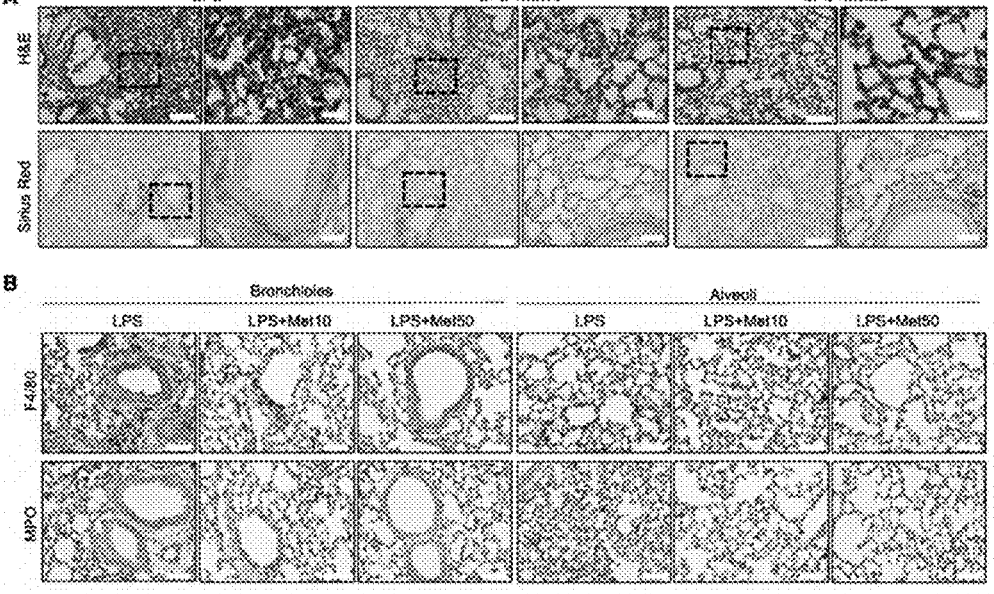
FIGS. 5A-5H: Metformin inhibits LPS-induced ARDS (FIG. 5A) H&E and Sirius red staining of lung tissue from mice that were left untreated or pretreated with 10 or 50 mg/kg metformin and challenged with 5 mg/kg LPS 24 h prior tissue collection. Scale bar, 100 mm and 20 mm. n=10 mice per group. 10-12 images per mouse were analyzed.

FIGS. 12A-12R: Metformin inhibits LPS-induced ARDS, related to FIG. 5. (FIG. 12A) Treatment and analysis scheme. Mice were i.p. injected with metformin (10 or 50 mg/kg), or vehicle daily for three days. LPS was i.p. injected 30 minutes after the last metformin injection. Lung tissue and BALF were collected 8 and 24 hrs after LPS administration. (FIG. 12B) H&E and Sirius red staining of lung tissue isolated at the 24 hrs time point from control mice or mice i.p. injected with LPS (5 mg/kg). Scale bar 100 μm. Scale bar in highlighted area 20 μm. n=10 mice per group. Ten to twelve images per mouse were evaluated. The figure shows a representative image for each group. (FIG. 12C) The degree of lung damage and inflammation was blindly scored by two mouse lung pathology experts. The degree of lung damage and inflammation was assigned an arbitrary score of 0 (baseline, no inflammation, no airway thickening, no edema), 1(minimal cellular infiltration, and minimal edema), 2 (mild-moderate cellular infiltration, plus mild airway thickening and mild edema), 3 (severe cellular infiltration, plus diffuse airway thickening and severe edema). The scores were averaged and are shown as average ±SEM. n=10-16 mice. *p<0.05; ****p<0.001; ns, not significant. All groups were compared to each other using ANOVA Kruskal-Wallis test. (FIG. 12D-FIG. 12E) Area (in %) occupied by F4/80 stained macrophages (FIG. 12D), and MPO stained neutrophils (FIG. 12E), in lung sections from FIG. 5B are shown as averages ±SEM. n=4 mice per group. Ten to twelve HMF per group were quantified using ImageJ. *p<0.05; ****p<0.001; ns, not significant. All groups were compared to each other using unpaired T-test and Mann-Whitney test. (FIG. 12F) TNF amounts in BALF from mice in FIG. 5A measured by ELISA. n=10 mice per group. *p<0.05; **p<0.001; ns, not significant. Unpaired T-test and Mann-Whitney test. (FIG. 12G) Percentage of F4/80+ cells with ASC specks in lung sections from mice treated as in FIG. 5E. Cells were quantified in 18-26 high magnification fields from 4-5 mice per group. Data are shown as average ±SEM. p<0.001. Unpaired T-test and Mann-Whitney test. (FIG. 12H) C/EBPβ and NFATc2 staining of lung tissue isolated at the 24 hrs time point from control mice or mice i.p. injected with LPS (5 mg/kg). Scale bar 50 μm. n=5 mice per group. Ten to twelve images per mouse were evaluated. The figure shows a representative image for each group. (FIG. 12I-FIG. 12J) Area (in %) occupied by C/EBPβ (FIG. 12I), and NFATc2 staining (FIG. 12J), in lung sections from (FIG. 12H) are shown as averages ±SEM. n=3 mice per group. Ten to twelve HMF per group were quantified using ImageJ. **p<0.001. All groups were compared to each other using unpaired T-test and Mann-Whitney test. (FIG. 12K) Kaplan Meyer survival analysis of mice pretreated with vehicle or metformin (10 and 50 mg/kg) and i.p. injected with LPS (30 mg/kg). n=8 mice per group. Log-rank (Mantel-Cox) test, p=0.0003 LPS+Met50 vs LPS; p=0.54 LPS+Met10 vs LPS. (FIG. 12L) Treatment and analysis scheme of therapeutic administration of metformin. Mice were i.p. injected with 50 mg/kg metformin or vehicle daily for two days starting 30 minutes after i.p. injection of 5 mg/kg LPS. Lung tissue and BALF were collected 48 hrs after LPS administration. (FIG. 12M) Treatment and analysis scheme for comparison the prophylactic i.p. versus oral administration of metformin. Metformin was provided to the mice in the drinking water (ad libitum at 400 mg/kg) or i.p. (daily at 50 mg/kg), starting two days before LPS challenge with 5 mg/kg. Lung tissue and plasma were collected 24 hrs after LPS administration. (FIG. 12N) H&E and Sirius red staining of lung tissue collected from mice in (FIG. 12B). Scale bar 100 μm. n=8 mice per group. Ten to twelve images per mouse were evaluated. The figure shows a representative image for each group. (FIG. 12O) Lung sections from mice in (FIG. 12N) were stained with F4/80 and MPO antibodies. Scale bar 50 μm. n=4 mice per group. Ten to twelve images per mouse were evaluated. The figure shows a representative image for each group. (FIG. 12P) Area (in %) occupied by F4/80 stained macrophages (left), and MPO stained neutrophils (right), in lung sections from (FIG. 12O) are shown as averages ±SEM. n=4 mice per group. Ten to twelve HMF per group were quantified using ImageJ. *p<0.05; ****p<0.001; ns, not significant. All groups were compared to each other using unpaired T-test and Mann-Whitney test. (FIG. 12Q) Metformin concentration in plasma from mice in (FIG. 12B) collected 1 hr after i.p. metformin on day 0 and 24 hrs after LPS challenge (day 1). n=5-14 mice per group. * p<0.05. Unpaired T-test and Mann-Whitney test. (FIG. 12R) Liquid consumption by mice in (FIG. 12N). Data are averages of 5 mice per group.

Figure 13A:
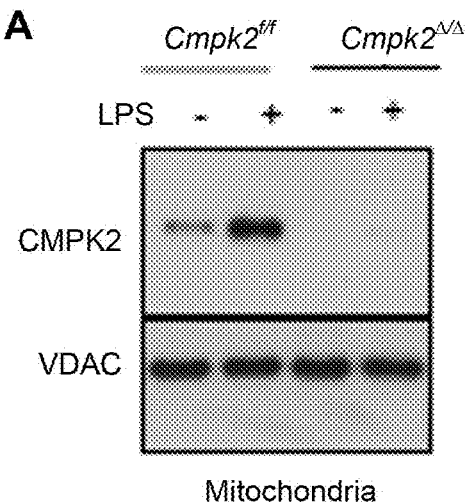
Figure 13B:
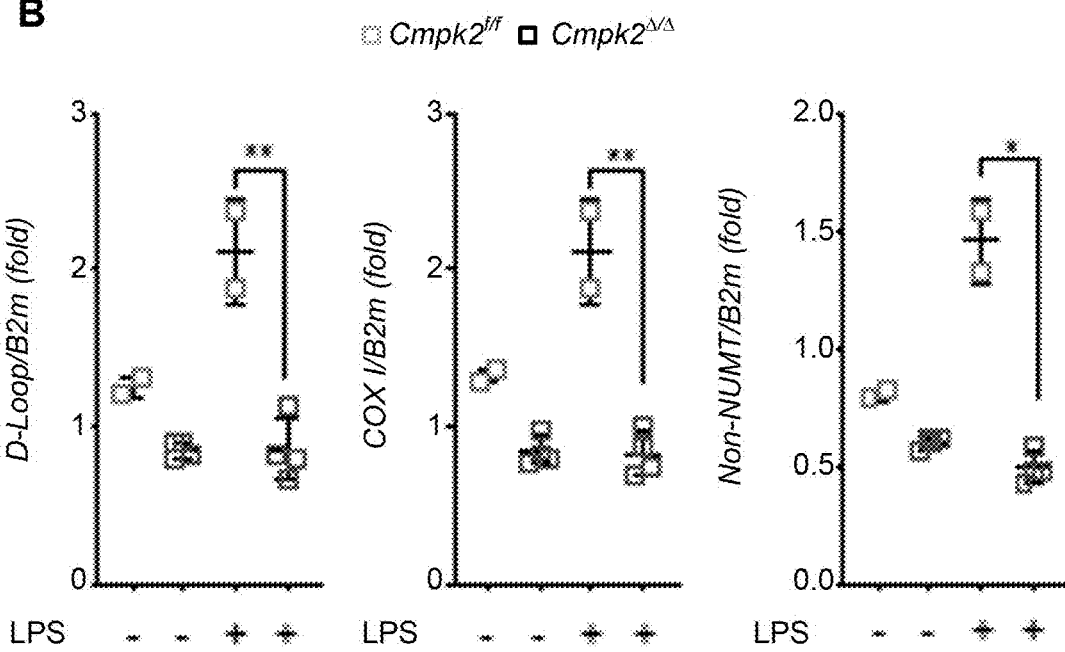

FIGS. 13A-13I: Myeloid specific CMPK2 ablation decreases IL-1β but not IL-6 amounts in BALF, related to FIG. 6. (FIG. 13A) IB analysis of CMPK2 in mitochondria from BMDM isolated from Cmpk2ff and Cmpk2$^{\Delta\Delta Mye}$ mice (Cmpk2$^{ff}$ and Cmpk2$^{\Delta/\Delta}$, respectively), that were stimulated with LPS (200 ng/ml) for 4 hrs. (FIG. 13B) Relative total mtDNA amounts Cmpk2$^{ff}$ and Cmpk2$^{\Delta/\Delta}$ BMDM stimulated with LPS as above. Shown are the ratios of D-loop mtDNA, Cox1 mtDNA, or mtDNA that is not inserted into nuclear DNA (non-NUMT) to B2m nDNA (n=4). Results are averages ±SD. *p<0.05; p<0.01; Two-sided unpaired t-test. (FIG. 13C-FIG. 13D) IB analysis of Casp1 p20 (FIG. 13C) and quantification (FIG. 13D) in culture supernatants of Cmpk2$^{ff}$ and Cmpk2$^{\Delta/\Delta}$ BMDM that were LPS-primed and stimulated with ATP (4 mM) or nigericin (10 μM) (n=3). Results are average ±SD. (FIG. 13E) IL-1β concentrations in culture supernatants of Cmpk2ff and Cmpk2$^{\Delta/\Delta}$ BMDM treated as indicated in (FIG. 13C). Results are averages ±SEM. p<0.01; **p<0.001. Two-sided unpaired t-test. (FIG. 13F) H&E and c/EBPβ staining of lung tissue collected from Cmpk2ff and Cmpk2$^{\Delta\Delta Mye}$ mice pretreated with 50 mg/kg metformin daily starting 2 days before LPS challenge. Scale bar 100 μm for H&E and 50 μm for C/EBPβ. n=4-8 mice per group. Ten to twelve images per group were evaluated. The figure shows a representative image for each group. (FIG. 13G) Area (in %) occupied by C/EBPβ positive cells is shown as averages ±SEM. n=4 mice per group. Fifteen to twenty HMF images per group were quantified using ImageJ. *p<0.005; ****p<0.001; ns, not significant. Unpaired T-test Mann-Whitney test. (FIG. 13H-FIG. 13I) IL-Iβ (FIG. 13H) and IL-6 (FIG. 13I) concentrations in bronchioalveolar lavage fluid from Cmpk2$^{ff}$ and Cmpk2$^{\Delta\Delta Mye}$ mice pretreated with 50 mg/kg metformin or vehicle starting 2 days before i.p. LPS administration. n=3-5 mice per group. *p<0.05; **p<0.01; ns, not significant. Unpaired T-test Mann-Whitney test.

FIGS. 14A-14E: Metformin ameliorates ARDS induced by SARS-CoV-2 infection of hACE2 mice, related to FIG. 7. (FIG. 14A-FIG. 14C) Area (in %) occupied by F4/80 stained macrophages (FIG. 14A), MPO stained neutrophils (FIG. 14B), and c/EBPβ positive cells (FIG. 14C), in lung sections from hACE2 Tg mice infected with SARS-CoV-2 (FIG. 15F). Data are averages ±SEM. n=4 mice per group. Ten HMF per group were quantified using ImageJ. *p<0.05; ****p<0.001. Unpaired T-test and Mann-Whitney test. (FIG. 14D) Percentages of F4/80+ cells with ASC specks in lung sections from mice in FIG. 7G. Cells were quantified in 8 high magnification fields from 4 mice per group. Data are shown as average ±SEM. *p<0.05. Unpaired T-test and Mann-Whitney test. (FIG. 14E) Percentage of weight loss during the course of SARS-CoV-2 infection (day 0 to day 5). n=8-9 mice per group. ***p<0.005. Two-way ANOVA Sydak's multiple comparison test.

DETAILED DESCRIPTION OF THE DISCLOSURE

Unless defined otherwise, all technical and scientific terms used herein have the same meanings as commonly understood by one of ordinary skill in the art to which this disclosure belongs. All nucleotide sequences provided herein are presented in the 5' to 3' direction. All polypeptide and protein sequences are presented in the direction of the amine terminus to carboxy terminus. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds, (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Throughout this disclosure several technical references are indicated by the first author's name and year of publication. The full bibliographic citations for these publications are found immediately preceding the claims.

As used in the specification and claims, the singular form "a", "an" and "the" include plural references unless the context clearly dictates otherwise. For example, the term "a polypeptide" includes a plurality of polypeptides, including mixtures thereof.

As used herein, "and/or" refers to and encompasses any and all possible combinations of one or more of the associated listed items, as well as the lack of combinations when interpreted in the alternative ("or").

"Optional" or "optionally" means that the subsequently described circumstance may or may not occur, so that the description includes instances where the circumstance occurs and instances where it does not.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

As used herein, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 15%, 10%, 5%, 3%, 2%, or 1%.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments, a mammal is a human. A mammal can be any age or at any stage of development (e.g., an adult, teen, child, infant, or a mammal in utero). A mammal can be male or female. In some embodiments, a subject is a human. In some embodiments, a subject has or is diagnosed of having or is suspected of having a disease.

As used herein, the term "animal" refers to living multicellular vertebrate organisms, a category that includes, for example, mammals and birds. The term "mammal" includes both human and non-human mammals.

As used herein, the terms "treating," "treatment" and the like are used herein to mean obtaining a desired pharmacologic and/or physiologic effect. In some embodiments, the effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder. In one aspect, treatment is the arrestment of the development of symptoms of the disease or disorder, e.g., a cancer. In some embodiments, they refer to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis or prevention.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

As used herein, the term "probe" intends a polynucleotide, an antibody or other agent that is used to detect and identify COVID-19 in a sample. A "probe" when used in the context of polynucleotide manipulation refers to an oligonucleotide that is provided as a reagent to detect a target potentially present in a sample of interest by hybridizing with the target. Usually, a probe will comprise a detectable label or marker or a means by which a label or marker can be attached, either before or subsequent to the hybridization reaction. Alternatively, a "probe" can be a biological compound such as a polypeptide, antibody, or fragments thereof that is capable of binding to the target potentially present in a sample of interest. In one aspect, the probe is suitable for use in polymerase chain reaction (PCT), Real-time PCR (RT-PCR), Loop Mediated Isothermal Amplification (LAMP) (see, Thi et al. Science Translational Medicine, Vol. 12, Issue 556, eabc7075), and reverse transcription LAMP (RT-LAMP). Additional assays for COVID detection are provided in Table 1.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers.

Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

As used herein, the term "label" or a detectable label intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, a purification label or maker refers to a label that may be used in purifying the molecule or component that the label is conjugated to, such as an epitope tag (including but not limited to a Myc tag, a human influenza hemagglutinin (HA) tag, a FLAG tag), an affinity tag (including but not limited to a glutathione-S transferase (GST), a poly-Histidine (His) tag, Calmodulin Binding Protein (CBP), or Maltose-binding protein (MBP)), or a fluorescent tag.

As used herein, the term "contacting" means direct or indirect binding or interaction between two or more molecules. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

As used herein, the term "sample" and "biological sample" and "agricultural sample" are used interchangeably, referring to sample material derived from a subject. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples may include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, blood, serum, mucus, bone marrow, lymph, and tears. In some aspects, agricultural samples include soil, foliage or any plant tissue or surface or other sample suspected of harboring virus. In addition, the sample can include industrial samples, such as those isolated from surfaces and the environment.

In some embodiments, the sample may be an upper respiratory specimen, such as a nasopharyngeal (NP) specimen, an oropharyngeal (OP) specimen, a nasal mid-turbinate swab, an anterior nares (nasal swab) specimen, or nasopharyngeal wash/aspirate or nasal wash/aspirate (NW) specimen.

In some embodiments, the samples include fluid from a subject, including, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a liquid biological sample is a blood plasma or serum sample. The term "blood" as used herein refers to a blood sample or preparation from a subject. The term encompasses whole blood, blood product or any fraction of blood, such as serum, plasma, buffy coat, or the like as conventionally defined. In some embodiments, the term "blood" refers to peripheral blood. Blood plasma refers to the fraction of whole blood resulting from centrifugation of blood treated with anticoagulants. Blood serum refers to the watery portion of fluid remaining after a blood sample has coagulated. Fluid samples often are collected in accordance with standard protocols hospitals or clinics generally follow. For blood, an appropriate amount of peripheral blood (e.g., between 3-40 milliliters) often is collected and can be stored according to standard procedures prior to or after preparation.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The host cell can be a prokaryotic or a eukaryotic cell.

In some embodiments, the cell or host cell as disclosed herein is a eukaryotic cell or a prokaryotic cell.

"Eukaryotic cells" comprise all of the life kingdoms except Monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission.

Examples include but are not limited to *Bacillus* bacteria, *E. coli* bacterium, and *Salmonella* bacterium.

In one embodiment, the term "disease" or "disorder" as used herein refers to a coronavirus infection, a status of being diagnosed with such infection, a status of being suspect of having such infection, a status of having being exposed to a coronavirus, or a status of at high risk of being exposed to a coronavirus. In one embodiment, the coronavirus is a respiratory virus. In a further embodiment, the disease is Coronavirus disease 2019 (COVID-19) caused by SARS-CoV-2. In yet a further embodiment, the disease is Severe acute respiratory syndrome (SARS) caused by SARS-CoV-1 or acute respiratory disease syndrome (ARDS).

"Acute respiratory disease syndrome" or "ARDS" refers to a type of respiratory failure or lung condition that results in or causes low blood oxygen levels and inflammation in the lungs. In the lungs of a patient with ARDS, fluid may build up within the alveoli of the lungs. Thus, ARDS impairs the lungs' ability to exchange oxygen and carbon dioxide. ARDS is especially prevelant in people suffering from Coronavirus disease 2019 (COVID-19) caused by SARS-CoV-2 and/or another comorbidity that increases the person's risk of developing a serious respiratory condition. Thus, "ARDS incidence" may be defined as the collection of fluid within the air sacs (alveoli) or the lungs, resulting in a decrease in blood oxygen supply. Therefore, the onset of ARDS can be detected via fluid buildup in the longs or decreased blood oxygen supply. A person or population at risk for developing ARDS includes any individual suffering from a chronic or acute respiratory condition or pulmonary condition, including but not limited to coronavirus, pneumonia, pulmonary fibrosis and/or any condition that results in respiratory or pulmonary dysfunction. Additionally, a person or population at risk for developing ARDS includes any individual suffering from a comorbidity that increases the likelihood of a poorer prognosis for coronavirus or any related respiratory condition. A reduction in the severity of ARDS is considered any reduction in the amount of fluid present in the lungs of a subject or the improvement of blood oxygen levels following treatment.

"Comorbidity" refers to the simultaneous presence of two or more diseases or medical conditions in a patient, or a disease or medical condition that is simultaneously present with another or others in a patient. Comorbities are generally associated with worse health outcomes and more complex clinical management. In the context of this disclosure, the term "comorbidity" relates to a disease or medical condition that increases the risk of coronavirus-related physical dysfunction or acute respiratory distress syndrome (ARDS). Comorbidities include, but are not limited to, pre-diabetes, type-II diabetes, obesity, or hypertension. However, the term "comorbidity" includes a condition or disease that increases the risk of a poorer coronavirus prognosis or the likelihood of developing coronavirus-related ARDS.

Type-II diabetes refers to a chronic condition or disease marked by an impairment in which a subject regulates and uses glucose and other sugars. Type-II diabetes is a chronic condition in which too much sugar is circulating in the blood stream, potentially leading to circulatory system, nervous system and immune system disorders. Type-II diabetes may be caused by the pancreas not producing enough insulin or the cells responding poorly to insulin causing the cells to intake less sugar.

Prediabetes, or borderline diabetes, is a condition characterized by slightly elevated blood glucose levels and is a condition indicative that a person is at risk of progressing to type-II diabetes. Prediabetes is generally tested via blood sugar level testing. Blood sugar in the range of 100 to 125 mg/dl may be indicative of prediabetes.

Obesity refers to a condition in which a person's weight is considered higher than what may be considered healthy for their given height. The presence of obesity may be tested by calculating an individual's body mass index (BMI). If the BMI of an individual is 30.0 or higher the individual may be considered obese.

Hypertension refers to a condition in which the force of blood or blood flow is too high against arterial walls. The force of blood flow against arterial wall is measured according to ones blood pressure. Generally, hypertension is defined as a blood pressure above 140/90 systolic/diastolic reading.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Application Publication No. WO 95/27071. Ads do not require integration into the host cell genome. Recombinant Ad derived vectors, particularly those that reduce the potential for recombination and generation of wild-type virus, have also been constructed. See, PCT International Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

The term "a regulatory sequence" "an expression control element" or "promoter" as used herein, intends a polynucleotide that is operatively linked to a target polynucleotide to be transcribed and/or replicated, and facilitates the expression and/or replication of the target polynucleotide. A promoter is an example of an expression control element or a regulatory sequence. Promoters can be located 5' or upstream of a gene or other polynucleotide, that provides a control point for regulated gene transcription. Polymerase II and III are examples of promoters.

A polymerase II or "pol II" promoter catalyzes the transcription of DNA to synthesize precursors of mRNA, and most shRNA and microRNA. Examples of pol II promoters are known in the art and include without limitation, the phosphoglycerate kinase ("PGK") promoter; EF1-alpha; CMV (minimal cytomegalovirus promoter); and LTRs from retroviral and lentiviral vectors.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives.

Coronaviridae express canonical polymerase genes, as well as structural genes, including S, E, M, and N, but also express a highly divergent set of accessory genes whose open reading frames are interspersed among the structural genes within the 3' one-third of the viral genome. The accessory genes are thought to contain "luxury" functions that are often not required for in-vitro virus replication. The severe acute respiratory syndrome coronavirus (SARS-CoV) expresses eight such accessory genes (ORF3a, -3b, -6, -7a, -7b, -8a, -8b, and -9b), the most of any known coronavirus. Of these, 7a, 3a and 8 represent the $3^{rd}$, $4^{th}$ and $5^{th}$ most abundant transcripts behind N and S transcripts.

In some embodiments, the coronavirus as used herein refers to a severe acute respiratory syndrome (SARS) associated coronavirus (SARS-CoV). In some embodiments, the coronavirus is either or both of SARS-CoV-1 and SARS-CoV-2. In some embodiments, the coronavirus comprises a virus selected from the group consisting of an Alphacoronavirus; a Colacovirus such as Bat coronavirus CDPHE15; a Decacovirus such as Bat coronavirus HKU10 or Rhinolophus ferrumequinum alphacoronavirus HuB-2013; a Duvinacovirus such as Human coronavirus 229E; a Luchacovirus such as Lucheng Rn rat coronavirus; a Minacovirus such as a Ferret coronavirus or Mink coronavirus 1; a Minunacovirus such as Miniopterus bat coronavirus 1 or Miniopterus bat coronavirus HKU8; a Myotacovirus such as *Myotis* ricketti alphacoronavirus Sax-2011; a nyctacovirus such as Nyctalus *velutinus* alphacoronavirus SC-2013; a Pedacovirus such as Porcine epidemic diarrhea virus or Scotophilus bat coronavirus 512; a Rhinacovirus such as Rhinolophus bat coronavirus HKU2; a Setracovirus such as Human coronavirus NL63 or NL63-related bat coronavirus strain BtKYNL63-9b; a Tegacovirus such as Alphacoronavirus 1; a Betacoronavirus; a Embecovirus such as Betacoronavirus 1, Human coronavirus OC43, China *Rattus* coronavirus HKU24, Human coronavirus HKU1 or Murine coronavirus; a Hibecovirus such as Bat Hp-betacoronavirus Zhejiang2013; a Merbecovirus such as Hedgehog coronavirus 1, Middle East respiratory syndrome-related coronavirus (MERS-CoV), *Pipistrellus* bat coronavirus HKU5 or *Tylonycteris* bat coronavirus HKU4; a Nobecovirus such as Rousettus bat coronavirus GCCDC1 or Rousettus bat coronavirus HKU9, a Sarbecovirus such as a Severe acute respiratory syndrome-related coronavirus, Severe acute respiratory syndrome coronavirus (SARS-CoV) or Severe acute respiratory syndrome coronavirus 2 (SARS-CoV-2, COVID-19); a Deltacoronavirus; an Andecovirus such as Wigeon coronavirus HKU20; a Buldecovirus such as Bulbul coronavirus HKU11, Porcine coronavirus HKU15, Munia coronavirus HKU13 or White-eye coronavirus HKU16; a Herdecovirus such as Night heron coronavirus HKU19; a Moordecovirus such as Common moorhen coronavirus HKU21; a Gammacoronavirus; a Cegacovirus such as Beluga whale coronavirus SW1; and an Igacovirus such as Avian coronavirus.

Symptoms of a coronavirus infection include, but are not limited to, mild symptoms, such as fatigues, tingling, tingling or numbness in the hands and feet, dizziness, confusion, brain fog, body ache, chills, loss of appetite, nausea, vomiting, abdominal pain or discomfort, loss of smell, inability to taste, muscle weakness, photophobia, adenopathy, headaches, cough, dry cough, shortness of breath, sore throat, lower extremity weakness/numbness, diarrhea, low blood $O_2$, sneezing, runny nose or post-nasal drip; severe symptoms, such as ventilatory use, high fever, severe cough, delirium, seizures, stroke, systematic inflammation, cytokine storm; and other symptoms, such as fever, swollen adenoids, pneumonia, bronchitis, and Dyspnea.

Viral infection of a coronavirus, such as SARS-COV-2, can be detected via a commercially available test known in the art, for example via polymerase chain reaction (PCR) or immunoassay may be used. In some embodiments, a method as disclosed herein further comprises detecting a coronavirus via a test known in the art. In one embodiment, active viral infection refers to an ongoing infection wherein the virus is making copies of itself and producing new virus. Such active viral infection may be detected via polymerase chain reaction (PCR). Non-limiting examples of primers and probes suitable for use in the PCR include 2019-nCoV CDC Probe and Primer Kit for SARS-CoV-2 (BioSearch Technologies, Catalog No. KIT-nCoV-PP1-1000), 2019-nCoV Kit, 500 rxn (Integrated DNA Technologies (IDT), Catalog No. 10006606) and 2019-nCoV Kit, 1000 rxn (Integrated DNA Technologies (IDT), Catalog No. 10006770). Also see, www.cdc.gov/coronavirus/2019-ncov/lab/rt-pcr-panel-primer-probes.html and www.cdc.gov/coronavirus/2019-ncov/downloads/List-of-Acceptable-Commercial-Primers-Probes.pdf. Suitable protocols for performing such tests can be found at www.cdc.gov/coronavirus/2019-ncovAab/virus-requests.html, www.fda.gov/media/134922/download, www.cdc.gov/coronavirus/2019-ncov/downloads/processing-sputum-specimens.pdf, www.fda.gov/media/134922/download, www.fda.gov/media/134919/download, www.fda.gov/media/134922/download. In some embodiments, diagnostic assays for COVID-19 based on detecting antibodies may be combined with the disclosure herein, such as those discussed by Lisboa Bastos M et al. (Diagnostic accuracy of serological tests for covid-19: systematic review and meta-analysis. BMJ. 2020 Jul. 1; 370:m2516. doi: 10.1136/bmj.m2516).

Other commercially available tests include, but not limited to those listed in the Table below.

TABLE 1

| Commercially available tests for SARS-CoV-2 and COVID-19 | |
| --- | --- |
| Company Name | Test Name |
| 3D Medicines | SARS-CoV-2 and Influenza A & B RT-qPCR Detection Kit |
| Abbott | SARS-CoV-2 IgG test |
| Abbott | ID Now COVID-19 |
| Abbott | Abbott RealTime SARS-CoV-2 EUA test |

TABLE 1-continued

Commercially available tests for SARS-CoV-2 and COVID-19

| Company Name | Test Name |
|---|---|
| Anatolia Geneworks | Bosphore Novel Coronavirus (2019-nCoV) Detection Kit |
| ARUP Laboratories | COVID-19 |
| A*STAR,Tan Tock Seng Hospital of Singapore | A*STAR Fortitude 2.0 |
| Assure Tech | COVID-19 IgG/IgM Rapid Test Device |
| Atila BioSystems | iAMP COVID-19 Detection Kit |
| AusDiagnostics | AusDiagnostics SARS-CoV-2, influenza, RSV panel |
| Autobio Diagnostics | Anti-SARS-CoV-2 Rapid Test |
| Avellino Lab | Avellino SARS-CoV-2/COVID-19 (AvellinoCoV2) |
| Bako Diagnostics | BakoDx SARS-CoV-2 RNA test |
| Baptist Hospital Miami Pathology/Laboratory Medicine Lab | COVID-19 RT-PCR Test |
| Becton Dickinson | BD SARS-CoV-2 Reagents for BD MAX System |
| Becton Dickinson, BioGx | BioGX SARS-CoV-2 Reagents for the BD MAX System |
| Beijing Decombio Biotechnology | Novel Coronavirus IgM/IgG Combo Rapid Test-Cassette |
| Beijing Diagreat Biotechnologies | 2019-nCoV IgG, IgM Antibody Determination Kits 2019-nCoV IgG/IgM Antibody Rapid Test Kit |
| Beijing Kewei Clinical Diagnostic Reagent | Genonto RapidTest10 COVID-19 IgG/IgM Antibody Rapid Test Kit |
| Beijing O&D Biotech | Coronavirus disease (COVID-19) Total Antibody Rapid Test (Colloidal Gold) |
| Beroni Group | SARS-CoV-2 IgG/IgM Antibody Detection Kit |
| BGI | Real-Time Fluorescent RT-PCR kit for detecting SARS-2019-nCoV |
| Biodesix | SARS-CoV-2 Droplet Digital PCR (ddPCR) test |
| Biolidics | 2019-nCoV IgG/IgM Detection Kit (Colloidal Gold) |
| BioMedomics | COVID-19 IgM-IgG Rapid Test |
| BioMérieux | SARS-CoV-2 R-GENE test |
| BioMérieux/BioFire Defense | BioFire COVID-19 test |
| Bioneer | AccuPower COVID-19 Real-Time RT-PCR Kit, AccuPower SARS-CoV-2 Real-Time RT-PCR Kit |
| Bio-Rad Laboratories | SARS-CoV-2 Total Ab test |
| BioReference Laboratories | Novel Coronavirus COVID-19 |
| Boston Children's Hospital Infectious Diseases Diagnostic Laboratory (IDDL) | Childrens-Altona-SARS-CoV-2 assay |
| BTNX | Rapid Response COVID-19 IgG/IgM Test Cassette |
| Cellex | qSARS-CoV-2 IgG/IgM Rapid Test |
| Centers for Disease Control and Prevention (performed at qualified high-complexity CLIA laboratories designated by CDC) | CDC 2019-Novel Coronavirus (2019-nCoV) Real-Time RT-PCR Diagnostic Panel (CDC) |
| Cepheid | Xpert Xpress SARS-CoV-2 test |
| CerTest Bio Tec | ViaSure SARS-CoV-2 Real Time PCR Detection Kit |
| Chembio Diagnostics | DDP COVID-19 IgM/IgG System |
| Children's Hospital of Philadelphia Infectious Disease Diagnostics Laboratory | SARS-CoV-2 RT-PCR test |
| ChromaCode | HDPCR SARS-CoV-2 real-time PCR assay |
| CirrusDx Laboratories | CirrusDx SARS-CoV-2 Assay |
| Co-Diagnostics | Logix Smart Coronavirus Disease 2019 (COVID-19) Kit |
| Core Technology | CoreTest COVID-19 IgM/IgG Ab Test |
| Credo Diagnostics Biomedical | VitaPCR SARS-CoV2 Assay |
| DiaCarta | Quanti Virus SARS-CoV-2 test kit |
| Diagnostic Solutions Laboratory | COVID-19 Assay |
| DiaSorin Molecular | Simplexa COVID-19 Direct |
| Diatherix Eurofins | COVID-19 Panel |
| Diazyme Laboratories | Diazyme DZ-LITE SARS-CoV-2 IgG, IgM CLIA Kits |
| Eachy Biopharmaceuticals | AccuRapid SARS-CoV-2 IgM/IgG Test Kit (Lateral Flow Immunoassay) |
| Euroimmun/PerkinElmer | EuroRealTime SARS-CoV-2 |
| Euroimmun/PerkinElmer | Anti-SARS-CoV-2 ELISAs (IgA and IgG) |
| Exact Sciences | SARS-CoV-2 Test |
| Fosun Pharma USA | Fosun COVID-19 RT-PCR Detection Kit |
| Fulgent Genetics/MedScan Laboratory | COVID-19 |
| Genetic Signatures | Easy Screen SARS-CoV-2 detection kit |
| Genetron | Detection Kit for Novel Coronavirus (SARS-CoV-2) RNA (PCR-Fluorescence Probing) |

TABLE 1-continued

Commercially available tests for SARS-CoV-2 and COVID-19

| Company Name | Test Name |
| --- | --- |
| GenMark Diagnostics | ePlex SARS-CoV-2 Test |
| Genomica/PharmMar Group | 2 kits: qCOVID-19, CLART COVID-19 |
| GenoSensor | GS COVID-19 RT-PCR Kit |
| Gnomegen | Gnomegen COVID-19 RT-Digital PCR Detection Kit |
| Gold Standard Diagnostics | SARS-CoV-2 IgG, IgM, IgA assays |
| Guangzhou Wondfo Biotech | SARS-CoV-2 Antibody Test |
| Hackensack University Medical Center (HUMC) Molecular Pathology Laboratory | CDI Enhanced COVID-19 Test |
| Hangzhou AllTest Biotech | AllTest 2019-nCoV IgG/IgM Rapid Test Cassette, AllTest COVID IgG/IgM Rapid Test Dipstick |
| Hangzhou Biotest Biotech | COVID-19 IgG/IgM Rapid Test Cassette |
| Hangzhou Clongene Biotech | Clungene COVID-19 IgM/IgG Rapid Test Cassette |
| Hangzhou Testsealabs Biotechnology | One Step SARS-CoV2 (COVID-19) IgG/IgM Test |
| Healgen Scientific | COVID-19 IgG/IgM Rapid Test Cassette(Whole Blood/Serum/Plasma) |
| Hologic | Panther Fusion SARS-CoV-2 assay |
| InBios International | Smart Detect SARS-CoV-2 rRT-PCR Kit |
| Innovita (Tangshan) Biological Technology | 2019-nCoV Ab Test (Colloidal Gold) |
| Integrated DNA Technologies/Danaher | IDT 2019-novel coronavirus kit |
| Integrity Laboratories | SARS-CoV-2 Assay |
| Ipsum Diagnostics | CoV-19 IDx assay |
| Jiangsu Macro & Micro-Test Med-Tech | SARS-CoV-2 IgM/IgG Rapid Assay Kit (Colloidal Gold) |
| JN Medsys | ProTect Covid-19 kit |
| Kogene Biotech | 2019 Novel Coronavirus Real-time PCR Kit |
| KorvaLabs | Curative-Korva SARS-Cov-2 Assay |
| Laboratory Corporation of America | LabCorp 2019 Novel Coronavirus test |
| LGC, Biosearch Technologies | 2019-nCoV CDC-qualified Probe and Primer Kits for SARS-CoV-2 |
| Lifeassay Diagnostics | Test-it COVID-19 IgM/IgG Lateral Flow Assay |
| Luminex | ARIES SARS-CoV-2 Assay |
| Luminex | NxTAGCoV Extended Panel Assay |
| Maccura Biotechnology | SARS-CoV-2 Fluorescent PCR Kit |
| Massachusetts General Hospital | MGH COVID-19 qPCR assay |
| Medical Systems Biotechnology | Coronavirus Disease 2019 Antibody (IgM/IgG) Combined Test Kit |
| Mesa Biotech | Accula SARS-CoV-2 test |
| Mount Sinai Labs | COVID-19 ELISA IgG Antibody Test |
| Nanjing Liming Bio-products | SARS-CoV-2 IgM/IgG Antibody Rapid Test Kit |
| NanoResearch | NanoMedicina SARS-CoV-2 IgM/IgG Antibody Rapid Test |
| Nantong Diagnos Biotechnology | (2019-nCoV) New coronavirus Antibody Test (Colloidal Gold) |
| NeuMoDx Molecular | NeuMoDx SARS-CoV-2 Assay |
| Nirmidas Biotech | COVID-19 (SARS-CoV-2) IgM/IgG Antibody Detection Kit |
| Northwestern Medicine Diagnostic Molecular Laboratory | SARS-Cov-2 Assay |
| Novacyt/Primerdesign | COVID-19 Genesig Real-Time PCR assay |
| NY State Department of Health (performed at Wadsworth Center and New York City Department of Health and Mental Hygiene, Public Health Laboratories) | New York SARS-CoV-2 Real-time Reverse Transcriptase (RT)-PCR Diagnostic Panel |
| Orig3n | Orig3n 2019 Novel Coronavirus (COVID-19) Test |
| Ortho Clinical Diagnostics | Vitros Immunodiagnostic Products Anti-SARS-CoV-2 Total Reagent Pack and Calibrators |
| Osang Healthcare | GeneFinder COVID-19 Plus RealAmp Kit |
| PathoFinder | RealAccurate Quadruplex Corona-plus PCR Kit |
| PCL | COVID19 IgG/IgM Rapid Gold |
| PerkinElmer | PerkinElmer New Coronavirus Nucleic Acid Detection Kit |
| Phamatech | COVID19 IgG/IgM Rapid Test |
| Promedical | COVID-19 Rapid Test, Wondfo SARS-CoV-2 Antibody Test (Lateral Flow Method) |
| Qiagen | QiaStat-Dx Respiratory SARS-CoV-2 Panel |
| Quest Diagnostics | Coronavirus Disease 2019 (COVID-19) Test |
| Quidel | Lyra SARS-CoV-2 Assay |
| Rendu Biotechnology | 2019-nCoV detection kit |
| Roche | Cobas SARS-CoV-2 Test |
| Rutgers University Clinical Genomics Laboratory | ThermoFisher - Applied Biosystems TaqPath COVID-19 Combo Kit |
| ScienCell Research Laboratories | ScienCell SARS-CoV-2 Coronavirus Real-time RT-PCR (RT-qPCR) Detection Kit |
| SD Biosensor | Standard Q COVID-19 IgM/IgG Duo |
| Seegene | Allplex 2019-nCoV Assay |

TABLE 1-continued

Commercially available tests for SARS-CoV-2 and COVID-19

| Company Name | Test Name |
|---|---|
| Sentinel Diagnostics | STAT-NAT COVID-19 HK kit, B kit |
| Shanghai Fosun Long March Medical Science/Shanghai Fosun Pharmaceutical | novel coronavirus nucleic acid detection kit |
| Shenzhen Landwind Medical | COVID-19 IgG/IgM Rapid Test Device |
| Snibe Diagnostics | Maglumi 2019-nCoV (SARS-CoV-2) IgM/IgG kits |
| SolGent | DiaPlexQ Novel Coronavirus (2019-nCoV) Detection kit |
| Specialty Diagnostic (SDI) Laboratories | SDI SARS-CoV-2 Assay |
| Stanford Health Care Clinical Virology Laboratory | SARS-CoV-2 PCR Assay |
| SureScreen Diagnostics | SureScreen COVID19 IgM/IgG Rapid Test Cassette |
| Suzhou Kangheshun Medical Technology | SARS-CoV-2 IgG/IgM Rapid Test Cassette |
| Systaaq Diagnostic Products | 2019-Novel Coronavirus (COVID-19) Real Time PCR Kit |
| Telepoint Medical Services | SARS-CoV-2 IgG/IgM Rapid Qualitative Test |
| Thermo Fisher Scientific | TaqPath COVID-19 Combo Kit, RT-PCR CE-IVD Kit |
| Tianjin Beroni Biotechnology | SARS-CoV-2 IgG/IgM Antibody Detection Kit |
| TIB Molbiol Syntheselabor | Sarbecovirus E-gene |
| Trax Management Services | Phoenix Dx 2019-CoV |
| United Biomedical | UBI SARS-CoV-2 ELISA |
| University of North Carolina Medical Center | UNC Health SARS-CoV-2 real-time RT-PCR test |
| Vela Diagnostics | ViroKey SARS-CoV-2 RT-PCR Test |
| Viracor Eurofins | Viracor SARS-CoV-2 assay |
| Vision Medicals | SARS-CoV-2 Clinical Sequencing assay |
| VivaChek Biotech (Hangzhou) | VivaDiag COVID-19 IgM/IgG Rapid Test |
| Yale New Haven Hospital Clinical Virology Laboratory | SARS-CoV-2 PCR test |
| YD Diagnostics | MolecuTech Real-Time COVID-19 |
| Zhejiang Orient Gene Biotech | COVID-19 IgG/IgM Rapid Test Cassette |
| Zhengzhou Fortune Bioscience | IgG/IgM Antibody Rapid Test Kits (Colloidal Gold Immunochromatography method) |
| Zhongshan Bio-Tech | SARS-CoV-2 IgM/IgG (GICA) |
| Zhuhai Encode Medical Engineering | Novel Coronavirus (COVID-19) IgG/IgM Rapid Test Device |
| Zhuhai Livzon Diagnostics | Diagnostic Kit for IgM/IgG Antibody to Coronavirus (SARS-CoV-2) (Colloidal Gold) |

"Administration" can be effected in one dose, continuously or intermittently throughout the course of treatment. Methods of determining the most effective means and dosage of administration are known to those of skill in the art and will vary with the composition used for therapy, the purpose of the therapy, the disease being treated, the target cell being treated, and the subject being treated. Single or multiple administrations can be carried out with the dose level and pattern being selected by the treating physician or treating veterinarian. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, inhalation administration, nasal administration, intravenous administration, injection, and topical application.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"An effective amount" or a "therapeutically effective amount" of a drug or an agent refers to an amount of the drug or the agent that is an amount sufficient to obtain a pharmacological response such as passive immunity; or alternatively, is an amount of the drug or agent that, when administered to a patient with a specified disorder or disease, is sufficient to have the intended effect, e.g., treatment, alleviation, amelioration, palliation or elimination of one or more manifestations of the specified disorder or disease in the patient. A therapeutic effect does not necessarily occur by administration of one dose, and may occur only after administration of a series of doses. Thus, a therapeutically effective amount may be administered in one or more administrations.

"Pediatric" refers to the medical treatment of children and their diseases. The age range of a pediatric patient may include a patient between the ages of 0 and 18 years of age.

"Systemic" or "systemic administration" refers to a route of administration of medication or other substance into the circulatory system such that the entire body may effected. Systemic administration may occur via intravenous, subcutaneously, topical, oral, or pulmonary administration "Local" or "local administration" refers to the administration of a medication or other substance at the site of where the desired treatment is required. For example, a medication may be delivered directly to the site of infection (i.e.: the lungs, respiratory system, or pulmonary system). Local administration may be accomplished by inhalation, through the pulmonary system, via injection to the target area, or any other route capable of direct administration to an area where the treatment is desired.

NLRP3 or NLR Family Pyrin Domain Containing 3 refers to the gene encoding for a pyrin-like protein containing a pyrin domain, a nucleotide-binding site (NBS) domain, and a leucine-rich repeat (LRR) motif. NLRP3 activation stimuli include extracellular ATP, reactive oxygen species, K(+) efflux, crystals of monosodium urate or cholesterol, amyloid-beta fibers, environmental or industrial particles and nanoparticles, or cytosolic dsRNA. The NLRP3 protein interacts with the apoptosis-associated speck-like protein PYCARD/ASC, which contains a caspase recruitment domain, and is a member of the NLRP3 inflammasome complex. The NLRP3 inflammasome complex functions as an upstream activator of NF-kappaB signaling, and it plays a role in the regulation of inflammation, the immune response, and apoptosis. As the sensor component of the NLRP3 inflammasome, plays a crucial role in innate immunity and inflammation. In response to pathogens and other damage-associated signals, initiates the formation of the inflammasome polymeric complex, made of NLRP3, PYCARD and CASP1 (and possibly CASP4 and CASP5). Recruitment of proCASPI to the inflammasome promotes its activation and CASP1-catalyzed IL1B and IL18 maturation and secretion in the extracellular milieu. The SARS-CoV 3a protein, a transmembrane pore-forming viroporin, has been shown to activate the NLRP3 inflammasome via the formation of ion channels in macrophages.

POLγ or DNA Polymerase Gamma refers to a nuclear-encoded Mitochondrial active DNA replication and repair enzyme. DNA polymerase gamma is heterotrimeric, consisting of a homodimer of accessory subunits plus a catalytic subunit. The protein encoded by this gene is the catalytic subunit of mitochondrial DNA polymerase. The encoded protein contains a polyglutamine tract near its N-terminus that may be polymorphic.

Ox-mtDNA refers to Oxidized Mitochondrial DNA. OX-mtDNA is released upon cytolysis, acts as a danger signal, and triggers inflammasome oligomerization via DNA sensors. During inflammasome assembly, the mitochondrial membrane depolarizes releasing mtDNA into the cytosol, and upon pyroptotic cell death, the oxidized mtDNA (ox-mtDNA) is released with other intracellular DAMPs into the extracellular matrix. DAMP release potentiates innate immune activation in proximate cells either through the engagement of DNA sensors or by direct interaction with NLRP3. Elevated levels of cell-free DNA have been reported in several chronic systemic inflammatory disorders.

An additional therapy for use in the methods comprise, or consist essentially of, or consist of, a treatment that suppresses an immune response of the subject, suppresses viral replication, ameliorating coronavirus-associated symptoms, or treating the coronavirus are available using drugs and therapies in the art. An immunotherapy in treating a coronavirus and/or NK cell based immunotherapy therapies in treating a coronavirus may be included, such as those shown in clinical trials with an identifier of NCT04324996, NCT04344548, NCT04375176, NCT04280224, NCT04365101 or NCT04470999.

"Second therapy" includes any therapy in addition to the primary therapy that suppresses an immune response of the subject, suppresses viral replication, ameliorating coronavirus-associated symptoms, or treating coronavirus. The second therapy can be in addition to the use of metformin, an analog or derivative of metformin.

Non-limiting examples of additional therapies are provided in Table 2, below. In one aspect, a therapeutically effective amount is administered.

TABLE 2

| Intervention | Type | Comparator | Phase | Clinical Trial Registration # |
|---|---|---|---|---|
| Hydroxychloroquine | Antimalarial | Placebo | Ph IV | ChiCTR2000029559 |
| Hydroxychloroquine | Antimalarial | Supportive care | Ph IV | ChiCTR2000029740 |
| Sildenafil citrate | Vasodilator | Single arm | Ph III | NCT04304313 |
| α lipoic acid | Antioxidant | Placebo | Ph IV | ChiCTR2000029851 |
| Ebastine + Lopinavir + Interferon α | Mucolytic; antiviral | Lopinavir + Interferon α | Ph IV | ChiCTR2000030535 |
| Mesenchymal stem cells | Cell therapy | Placebo | Ph I/II | ChiCTR2000029990 |
| Danoprevir + Ritonavir + | Antiviral; Immunomodulator | Lopinavir/ritonavir; Pegasys; Novaferon; Chinese medicines + interferon (4 arms) | Ph IV | NCT04291729 |
| Bevacizumab biosimilar | Antibody | Single arm | Ph II/III | NCT04275414 |
| Tocilizumab | Antibody | Single arm | Ph II | NCT04315480 |
| Remdesivir | Antiviral | Placebo | Ph III | NCT04257656 |
| Remdesivir | Antiviral | Placebo | Ph III | NCT04252664 |
| Dipyridamole | Vasodilator | Supportive care | Ph IV | ChiCTR2000030055 |
| Low molecular weight heparin | Anticoagulant | Supportive care | Ph IV | ChiCTR2000030946 |

TABLE 2-continued

| Intervention | Type | Comparator | Phase | Clinical Trial Registration # |
|---|---|---|---|---|
| Bromhexine + Arbidol umifenovir + Favipiravir + Interferon α2b | Mucolytic; Antiviral; Immunomodulator | Arbidol umifenovir + Interferon α2b | N/A | NCT04273763 |
| Favipiravir high dose; middle dose; low dose (3 arms) | Antiviral | N/A | Ph II | ChiCTR2000029996 |
| Levamisole + Budesonide + Formoterol + Lopinavir + Ritonavir + Hydoxychloroquine | Antiparasitic; Corticosteroid; Bronchodilator; Antiviral; Antimalarial | Lopinavir + Ritonavir + Hydoxychloroquine | Ph II/III | NCT04331470 |
| Interferon β1a + Hydroxychloroquine + Lopinavir/Ritonavir; Interferon β1b + Hydroxychloroquine + Lopinavir/Ritonavir (2 arms) | Immunomodulator; Antimalarial; Antiviral | Hydroxychloroquine + Lopinavir/Ritonavir | Ph IV | NCT04343768 |
| Interferon β1a + Lopinavir/Ritonavir + Hydroxychloroquine | Immunomodulator; Antimalarial; Antiviral | Lopinavir/Ritonavir + Hydroxychloroquine | Ph IV | NCT04350671 |
| Umifenovir + Interferon β1a + Lopinavir/Ritonavir + Hydroxychloroquine | Antiviral; Immunomodulator; Antimalarial | Lopinavir/Ritonavir + Hydroxychloroquine | Ph IV | NCT04350684 |
| Methylprednisolone | Corticosteroid | Supportive care | Ph II/III | NCT04244591 |
| DAS181 | Antiviral | Single arm | N/A | NCT04324489 |
| Hydroxychloroquine; Chloroquine (3 arms) | Antimalarial | Placebo | Ph IV | NCT04346667 |
| Chloroquine phosphate | Antimalarial | Placebo | Ph II | ChiCTR2000031204 |
| Thalidomide | Immunomodulator | Placebo | Ph II | NCT04273581 |
| Hydroxychloroquine; Chloroquine (3 arms) | Antimalarial | Placebo | Ph IV | NCT04351191 |
| Baricitinib; Ritonavir | Anti-inflammatory; Antiviral | Antiviral and/or hydroxychloroquine | Ph III | NCT04320277 |
| Danoprevir + Ritonavir | Antiviral | Single arm | Ph IV | NCT04345276 |
| α lipoic acid | Antioxidant | Placebo | Ph IV | ChiCTR2000030471 |
| Intravenous immunoglobulin (IVIG) | Antibody | Supportive care | Ph II/III | NCT04261426 |
| Hydroxychloroquine | Antimalarial | Chloroquine phosphate | Ph IV | ChiCTR2000029898 |
| Hydroxychloroquine | Antimalarial | Chloroquine phosphate | Ph IV | ChiCTR2000029899 |
| Bevacizumab biosimilar | Antibody | Supportive care | N/A | NCT04305106 |
| Danoprevir + Ritonavir | Antiviral | Supportive care | N/A | ChiCTR2000030259 |
| Tocilizumab + Adalimumab | Antibody | Supportive care | Ph IV | ChiCTR2000030580 |
| PD-1 blocking antibody; Thymosin (2 arms) | Antibody; hormone | Supportive care | Ph II | NCT04268537 |
| Mesenchymal stem cells | Cell therapy | Single arm | Ph II | NCT04269525 |
| Corticosteroid | Corticosteroid | Supportive care | Ph IV | ChiCTR2000030481 |
| Anakinra | Immunomodulator | Supportive care | Ph II | NCT04341584 |
| Eculizumab | Antibody | Supportive care | Ph II | NCT04346797 |
| Sarilumab + Azithromycin + Hydroxychloroquine | Antibody; Antibiotic; Antimalarial | Sarilumab | Ph II/III | NCT04341870 |
| Methylprednisolone | Corticosteroid | Supportive care | N/A | NCT04273321 |
| Remdesivir 5 days; 10 days (2 arms) | Antiviral | N/A | Ph III | NCT04292899 |
| Remdesivir 5 days; 10 days (2 arms) | Antiviral | Supportive care | Ph III | NCT04292730 |
| Povidone-Iodine; Chlorhexidine (2 arms) | Antiseptic | Placebo | Ph II | NCT04344236 |

TABLE 2-continued

| Intervention | Type | Comparator | Phase | Clinical Trial Registration # |
|---|---|---|---|---|
| Favipiravir + Tocilizumab | Antiviral; Antibody | Favipiravir; Tocilizumab (2 arms) | N/A | NCT04310228 |
| ASC09 + oseltamivir; ritonavir + oseltamivir (2 arms) | Antiviral | Oseltamivir | Ph III | NCT04261270 |
| Nintedanib | Antifibrotic | Placebo | Ph II | NCT04338802 |
| Tocilizumab | Antibody | Supportive care | Ph IV | ChiCTR2000029765 |
| Ruxolitinib + Simvastatin | Anti-inflammatory; Vasodilator | Supportive care | Ph II | NCT04348695 |
| Hydroxychloroquine + Azithromycin | Antimalarial; Antibiotic | Hydroxychloroquine + Placebo; Placebo (2 arms) | N/A | NCT04349592 |
| Xiyanping + Lopinavir/ritonavir + interferon α | Antiviral; Immunomodulator | Lopinavir/ritonavir + interferon α | N/A | NCT04275388 |
| Tocilizumab + Pembrolizumab | Anti-inflammatory; Immune booster | Supportive care | Ph II | NCT04335305 |
| Mesenchymal stem cells | Cell therapy | Single arm | Ph I | NCT04315987 |
| Siltuximab; Methylprednisolone (2 arms) | Anti-inflammatory | N/A | Ph II | NCT04329650 |
| Hydroxychloroquine | Antimalarial | Placebo | Ph I | NCT04333654 |
| Interferon α1b + Thymosin α1; Interferon α1b (2 arms) | Immunomodulator; hormone | N/A | Ph III | NCT04320238 |
| Methylprednisolone | Corticosteroid | Supportive care | Ph II/III | NCT04323592 |
| Chloroquine phosphate; Hydroxychloroquine (2 arms) | Antimalarial | Supportive care | Ph IV | ChiCTR2000029992 |
| Hydroxychloroquine; Hydroxychloroquine + Azithromycin (2 arms) | Antimalarial; Antibiotic | Placebo | Ph III | NCT04328272 |
| Triazavirin | Antiviral | Placebo | Ph III | ChiCTR2000030001 |
| Danoprevir + Ritonavir | Antiviral | Single arm | N/A | ChiCTR2000031734 |
| Tocilizumab | Antibody | Supportive care | Ph II | NCT04346355 |
| Angiotensin 1-7 | Vasodilator | Placebo | Ph II/III | NCT04332666 |
| Colchicine | Anti-inflammatory | Standard of care | Ph III | NCT04328480 |
| Thalidomide | Immunomodulator | Placebo | Ph II | NCT04273529 |
| Lopinavir/ritonavir; Arbidol umifenovir (2 arms) | Antiviral | Supportive care | Ph IV | NCT04252885 |
| Colchicine | Anti-inflammatory | Standard of care | Ph II | NCT04322565 |
| Leflunomide | Immunomodulator | Placebo | Ph III | ChiCTR2000030058 |
| Interferon α1β | Immunomodulator | Supportive care | Ph I | NCT04293887 |
| Chloroquine phosphate | Antimalarial | Supportive care | Ph IV | ChiCTR2000030718 |
| Nitazoxanide | Antiviral | Placebo | N/A | NCT04348409 |
| Hydroxychloroquine + Azithromycin | Antimalarial; Antibiotic | Single arm | Ph I | NCT04329572 |
| Tocilizumab | Antibody | Single arm | Ph II | ChiCTR2000030196 |
| Interferon α1β | Immunomodulator | Placebo | Ph IV | ChiCTR2000029989 |
| Mesenchymal stem cells | Cell therapy | Placebo | Ph II | ChiCTR2000030138 |
| ASC09/ritonavir; Lopinavir/ritonavir (2 arms) | Antiviral | N/A | N/A | NCT04261907 |
| Favipiravir + Tocilizumab | Antiviral; Antibody | Favipiravir; Tocilizumab (2 arms) | Ph IV | ChiCTR2000030894 |
| Mesenchymal stem cell-derived exosomes | Anti-inflammatory | Single arm | Ph I | NCT04276987 |
| Ulinastatin | Anti-inflammatory | Supportive care | Ph IV | ChiCTR2000030779 |
| Chloroquine phosphate | Antimalarial | Single arm | Ph IV | ChiCTR2000029975 |
| Chloroquine phosphate | Antimalarial | Supportive care | Ph IV | ChiCTR2000029988 |
| Dexamethasone + Hydroxychloroquine | Corticosteroid; Antimalarial | Hydroxychloroquine | Ph III | NCT04347980 |
| Intravenous immunoglobulin (IVIG) | Antibody | Placebo | Ph III | NCT04350580 |

| Intervention | Type | Comparator | Phase | Clinical Trial Registration # |
|---|---|---|---|---|
| Ruxolitinib | Anti-inflammatory | Single arm | Ph I/II | NCT04334044 |
| Tacrolimus + Methylprednisolone | Immunomodulator; Anti-inflammatory | Supportive care | Ph III | NCT04341038 |
| Favipiravir | Antiviral | Supportive care | N/A | NCT04333589 |
| TD-0903 (2 arms) | Anti-inflammatory | Placebo | Ph I | NCT04350736 |
| Arbidol umifenovir; Oseltamivir; Lopinavir/ritonavir (3 arms) | Antiviral | N/A | Ph IV | NCT04255017 |
| Arbidol umifenovir; peginterferon alfa-2b | Antiviral; Immunomodulator | Arbidol umifenovir | Ph IV | NCT04254874 |
| Methylprednisolone low dose; high dose (2 arms) | Corticosteroid | N/A | Ph IV | NCT04263402 |
| Hydroxychloroquine (3 arms) | Antimalarial | Placebo | Ph II | NCT04343677 |
| Hydroxychloroquine | Antimalarial | Placebo | Ph III | NCT04346329 |
| Hydroxychloroquine | Antimalarial | Single arm | Ph I | NCT04351620 |
| Luvox fluvoxamine | Immunomodulator | Placebo | Ph II | NCT04342663 |
| Piclidenoson | Anti-inflammatory | Supportive care | Ph II | NCT04333472 |
| Hydroxychloroquine + Bromhexine | Antimalarial; Mucolytic | Bromhexine | Ph I | NCT04340349 |
| Allogeneic natural killer cells | Cell therapy | Single arm | Ph I/II | NCT04344548 |
| Chloroquine analog; Nivolumab; Tocilizumab (3 arms) | Antimalarial; Immune booster; Anti-inflammatory | Standard of care | Ph II | NCT04333914 |
| Hydroxychloroquine + Indomethacin + Zithromax | Antimalarial; Anti-inflammatory; Antibiotic | Single arm | Ph I/II | NCT04344457 |
| Tofacitinib | Anti-inflammatory | Single arm | Ph II | NCT04332042 |
| Favipiravir + Chloroquine phosphate | Antiviral; Antimalarial | Favipiravir; Placebo (2 arms) | Ph II/III | ChiCTR2000030987 |
| Hydroxychloroquine + Azithromycin | Antimalarial; Antibiotic | Single arm | Ph I | NCT04348474 |
| Inactivated Mycobacterium w | Cell therapy | Placebo | N/A | NCT04347174 |
| Interferon α1β | Immunomodulator | Supportive care | Ph IV | ChiCTR2000030013 |
| Hydroxychloroquine daily; weekly (2 arms) | Antimalarial | Placebo | Ph III | NCT04341441 |
| Lopinavir/ritonavir + emtricitabine/tenofovir alafenamide fumarate | Antiviral | Lopinavir/ritonavir | N/A | ChiCTR2000029468 |
| Alvesco ciclesonide; Alvesco ciclesonide + Hydroxychloroquine (2 arms) | Antimalarial; Corticosteroid | Standard of care | Ph II | NCT04330586 |
| Emtricitabine + Tenofovir disoproxil + Hydroxychloroquine; Emtricitabine + Tenofovir disoproxil; Hydroxychloroquine (3 arms) | Antiviral; Antimalarial | Placebo | Ph III | NCT04334928 |
| Mesenchymal stem cells | Cell therapy | Placebo | Ph I/II | NCT04339660 |
| Danoprevir + Ritonavir | Antiviral | Supportive care | N/A | ChiCTR2000030472 |
| Mesenchymal stem cells | Cell therapy | Single arm | Ph I | NCT04313322 |
| Novaferon + Arbidol umifenovir; Novaferon + Lopinavir/ritonavir (3 arms) | Antiviral; Immunomodulator | Arbidol umifenovir; Lopinavir/ritonavir (3 arms) | Ph IV | ChiCTR2000029573 |
| Escin oral; parenteral (2 arms) | Anti-inflammatory | Supportive care | Ph II/III | NCT04322344 |
| Tradjenta linagliptin | Antiviral | Insulin | Ph IV | NCT04341935 |
| Mesenchymal stem cells | Cell therapy | Placebo | N/A | NCT04273646 |
| Azvudine | Antiviral | Single arm | N/A | ChiCTR2000030041 |

Modes for Carrying Out the Disclosure

Provided herein are methods for preventing, reducing disease severity or acute respiratory distress syndrome (ARDS) incidence in a subject infected with a respiratory virus comprising, or consisting essentially of, or yet consisting of, administering to the subject metformin or an analog or derivative thereof, thereby reducing disease severity or ARDS incidence in the subject. As used herein, the term "metformin" includes, for example, N,N-dimethyl-biguanide, and is sold under the tradename Glucophare among others, and is has been used for the treatment of type 2 diabetes. It is formulated for oral administration for the treatment of diabetes. It also is prescribed for the treatment of polycystic ovary disease. Metformin analogs are known in the art and include N-benzylbiguanide, and those described in U.S. Pat. No. 9,862,693 and US 2017/0106006 A1. Non-limiting examples of metformin derivatives include sulfenamide and sulfonamide derivatives (see Markowicz-Piasecka (2019)). https://www.nature.com/articles/s41598-019-43083-z), HL010183 (see Koh et al. (2013) Bioorg. Med. Chem. April 15; 21*8):2305-2313; and those disclosed in U.S. Pat. No. 8,853,259). In one aspect, the metformin, analog, or derivative thereof is detectable labeled. In another aspect, the metformin, analog, or derivative thereof is administered in a composition, e.g., a pharmaceutical composition that additional comprises, or consists essentially thereof, or consists of, a carrier, preservative or flavoring agent, consistent with its intended mode of administration.

In a further aspect, the subject is suffering from a comorbidity. The comorbidity comprises, or consists essentially of, or yet consists of, pre-diabetes, type-II diabetes, obesity, or hypertensions. In another aspect, the comorbidity is any disease or medical condition which increases the risk of a poorer coronavirus prognosis, coronavirus-related death, and/or the onset of ARDS in the subject.

In a further aspect, the method further comprises, or alternatively consists essentially of, or yet further consists of, administration of an effective amount of a second therapy to treat the subject infected with the respiratory virus. Non-limiting examples of such second therapies are provided in Table 2. In another aspect, the second therapy is detectably labeled.

In one aspect of the methods disclosed herein, the subject is infected with a virus that causes ARDS, e.g., coronavirus. In a further aspect, the subject is infected with SARS-CoV-2. Methods to detect viral infection are known in the art and include application of PCR and LAMP. Methods to diagnose coronaviral infections are known in the art and include those described in Table 1. In one aspect of the disclosed methods, the subject is a mammal. In another aspect, the subject is a canine, feline, equine, bovine, murine, rat or a human. The subject can be of any age or gender, e.g., a juvenile, pediatric or adult subject. The methods can be practiced on animals and mammals to treat, diminish or treat disease or they can be used in animal studies to test for combination therapies or new analogs or derivatives of metformin. In a further aspect, the subject has been selected for the therapy by assaying a sample suspected of containing the virus from the subject for presence of the virus. Thus, in further aspect, the method further comprising assaying a sample isolated from the subject for the virus and then administering an effective amount of the metformin, analog or derivative thereof, alone or in combination with a second therapy to the subject.

In a further aspect, a therapeutically effective amount of the metformin, analog, or derivative thereof is administered to the subject. The effective amount will vary with the metformin, analog or derivative thereof with the viral infection, the subject, the course of the disease, as determined by the prescribing physician, veterinarian or researcher. In a yet further aspect, a therapeutically effective amount of the second drug or therapy is administered to the subject. The effective amount will vary with the metformin, analog or derivative thereof with the viral infection, the subject, the course of the disease, as determined by the prescribing physician, veterinarian or researcher. These effective amounts can be administered in one or more doses as necessary to achieve the desired result. Administration can be local at the site of infection or systemic. Non-limiting routes of administration include systemic, intraperitoneal, inhalation, oral, intravenously or a combination thereof.

The methods of this disclosure have been should to not only treat ARDS and viral infection but also abrogate POLγ-dependent mtDNA synthesis or Ox-mtDNA production, thereby inhibiting NLRP3 inflammasome activation. In this aspect, metformin, or an analog, or derivative thereof is administered to a subject to inhibit ETCCI and reduce ATP production, thus abrogating POLγ-dependent mtDNA synthesis and Ox-mtDNA production, thereby inhibiting NLRP3 inflammasome activation.

One can determine if the administration has been successful or if additional doses or administrations are necessary by assaying for alleviation of clinical symptoms and/or viral load. In one aspect, a method as disclosed in Table 1 can be used to assay for viral infection.

Further provided herein is a composition comprising, or consisting essentially of, or yet consisting of an effective amount of metformin or an analog or derivative for the use of reducing disease severity or ARDS incidence in a subject infected with a respiratory virus. As used herein, the term "metformin" includes, for example, N,N-dimethylbiguanide, and is sold under the tradename Glucophare among others, and is has been used for the treatment of type 2 diabetes. It is formulated for oral administration for the treatment of diabetes. It also is prescribed for the treatment of polycystic ovary system. Metformin analogs are known in the art and include N-benzylbiguanide, and those described in U.S. Pat. No. 9,862,693 and US 2017/0106006 A1. Non-limiting examples of metformin derivatives include sulfenamide and sulfonamide derivatives, see Markowicz-Piasecka (2019). https://www.nature.com/articles/s41598-019-43083-z), HL010183 (see Koh et al. (2013) Bioorg. Med. Chem. April 15; 21*8):2305-2313, and those disclosed in U.S. Pat. No. 8,853,259. In one aspect, the metformin, analog, or derivative thereof is detectable labeled. In another aspect, the metformin, analog, or derivative thereof is also comprises, or consists essentially thereof, or consists of, a carrier, preservative or flavoring agent, consistent with its intended mode of administration.

In a further aspect, the composition further comprises, or alternatively consists essentially of, or yet further consists of, an effective amount of a second therapy to treat the subject infected with the respiratory virus. Non-limiting examples of such second therapies are provided in Table 2. In another aspect, the second therapy is detectably labeled. In one aspect, the subject is infected with a virus that causes ARDS, e.g., coronavirus. In a further aspect, the subject is infected with SARS-CoV-2. In one aspect, the subject is a mammal. In another aspect, the subject is a canine, feline, equine, bovine, murine, rat or a human. The subject can be of any age or gender, e.g., a juvenile, pediatric or adult subject. The compositions can be practiced on animals and mammals to treat, diminish or treat disease or they can be used in animal studies to test for combination therapies or new analogs or derivatives of metformin. In another aspect, the composition further comprises, or consists essentially of, or yet further consists of an effective amount of a therapy to treat the subject infected with the respiratory virus. In one aspect, the respiratory virus is a coronavirus, e.g., SARS-CoV-2.

Also provided are kits comprising an effective amount of metformin or an analog or derivative for the use of reducing disease severity or ARDS incidence in a subject infected with a respiratory virus. In a further aspect, the further comprising an effective amount a second therapy to treat the subject infected with the respiratory virus. In one aspect the respiratory virus is coronavirus, e.g., SARS-CoV-2.

Experimental

Acute respiratory distress syndrome (ARDS), an inflammatory condition with high mortality rates, is common in severe COVID-19, whose risk is reduced by metformin rather than other anti-diabetic medications. Given evidence of inflammasome assembly in post-mortem COVID-19 lungs, Applicant asked whether and how metformin inhibits inflammasome activation and exerts its anti-inflammatory effect. Applicant shows that metformin inhibits NLRP3 inflammasome activation and IL-1β production in cultured and alveolar macrophages along with inflammasome-independent IL-6 secretion, attenuating LPS- and SARS-CoV-2 induced ARDS. By targeting electron transfer chain complex 1, independently of AMPK or NF-κB, metformin blocks LPS-induced and ATP-dependent mitochondrial (mt) DNA synthesis and generation of the NLRP3 ligand oxidized mtDNA. Myeloid-specific ablation of LPS-induced cytidine monophosphate kinase 2 (CMPK2), a rate limiting enzyme in the salvage pathway of mtDNA synthesis, reduced ARDS severity without a direct effect on IL-6. Thus, inhibition of ATP and CMPK2-dependent mtDNA synthesis is sufficient for ARDS amelioration. When using animal models there is always a concern regarding human relevance. Applicant sought a mechanistic explanation to observational studies in which metformin for glycemic control was found to reduce ARDS and COVID-19 risk. It is unclear whether short term metformin treatment fully mimics long term drug treatment. It is also unclear whether LPS-induced ARDS in mice mimics bacterial-induced human ARDS, as LPS is only one component of gram negative bacterial and absent in gram positive bacteria. To model COVID-19, Applicant used hACE2 transgenic mice. Although these mice succumb to SARS-CoV-2 infection, their lungs were not as heavily infiltrated with inflammatory cells as COVID-19 patients' lungs. Moreover, hACE2 transgenic mice can only be followed for 1 week after SARS-CoV-2 infection and are unsuitable for studying prolonged COVID-19. It also remains to be seen whether COVID-19 patients who benefited from metformin use, show reduced ASC spec formation in alveolar macrophages.

Acute respiratory distress syndrome (ARDS) is a severe pulmonary inflammatory reaction triggered by respiratory viruses and bacteria and even physical trauma (Han and Mallampalli, 2015). Recently, ARDS has emerged as a leading cause of death in ICU hospitalized COVID-19 patients (Tay et al., 2020), although its features were described as somewhat different and milder than "typical" ARDS (Li and Ma, 2020). ARDS onset depends on innate immune cells, monocytes, macrophages and neutrophils, that propagate uncontrolled inflammation and tissue injury by secreting IL-1β, IL-18, IL-6 and TNF (Han and Mallampalli, 2015). Bacterially triggered ARDS is initiated on Toll like receptor (TLR) engagement, but in sterile or virally induced ARDS, the inflammatory response is thought to be initiated by the NLRP3 inflammasome, which is highly expressed and activated in myeloid cells that have been primed on TLR engagement by viral RNA or proteins, such as the SARS-CoV spike protein (Dolinay et al., 2012; Dosch et al., 2009). Following priming, the NLRP3 inflammasome, composed of the enzyme caspase-1 (Casp1), the sensor NLRP3, NEK7 and the scaffold protein ASC (Sharif et al., 2019), is activated by damage associated molecular patterns (DAMPs), e.g. ATP and uric acid (UA) crystals, released by injured epithelial cells (Tschopp and Schroder, 2010), or the SARS-CoV pore-forming protein viroporin 3a (Chen et al., 2019). Injured epithelial cells also release IL-1α, which primes airway macrophages via the same adaptors used by TLRs, MyD88 and TRIF (Cohen, 2014). Macrophage priming stimulates DNA polymerase-g (POLg)-mediated mitochondrial (mt) DNA synthesis, whereas ATP, UA crystals and other DAMPs elicit mitochondrial damage and reactive oxygen species (ROS) production (Zhong et al., 2018; Zhou et al., 2011). Mitochondrial ROS react with newly synthesized mtDNA to generate oxidized (Ox) mtDNA, which binds to cytoplasmic NLRP3 and triggers inflammasome assembly and activation (Shimada et al., 2012; Zhong et al., 2018). Circulating mtDNA was suggested to be an inflammatory mediator that leads to distant organ damage (Grazioli and Pugin, 2018), and an early indicator of severe illness and mortality in ARDS (Han and Mallampalli, 2015) and COVID-19 (Scozzi et al., 2020). Other factors that amplify ARDS (Day et al., 2009) and COVID-19 (Gao et al., 2020; Richardson et al., 2020; Singh and Khan, 2020; Verma et al., 2020; Yang et al., 2020a) severity and mortality are old age and co-morbidities such as type 2 diabetes mellitus (T2DM) and obesity.

Several commonly used drugs, including dexamethasone, statins and metformin were found to reduce COVID-19 severity and mortality (Bramante et al., 2020; Group et al., 2021; Zhang et al., 2020). While dexamethasone is currently used in COVID-19 treatment, statins and metformin were only described to have a prophylactic effect. In particular, early studies from China have noted that long-term metformin usage decreased hospital mortality by 4-fold relative to other anti-diabetic drugs (Li et al., 2020; Luo et al., 2020), and reduced COVID-19-associated heart failure and inflammation (Cheng et al., 2020). In a US-based study metformin reduced the odds ratio of COVID-19 death in Blacks/African Americans with T2D by 10-fold (Crouse et al., 2020). Extended metformin usage ameliorates other age-related pathologies and extends life span and health span in model organisms (Barzilai et al., 2016), effects that are unrelated to glycemic control (Valencia et al., 2017), but may be due to its anti-inflammatory properties (Barzilai et al., 2016; Marcucci et al., 2020; Pollak, 2017). Prolonged use of metformin, but not other anti-diabetic drugs, also correlates with decreased age-related dementia and neurodegenerative disease incidence in elderly T2DM patients (Campbell et al., 2018; Markowicz-Piasecka et al., 2017; Shi et al., 2019). Metformin's mode of action remains debatable, but most researchers agree that it inhibits oxidative phosphorylation and reduces ATP production through interaction with respiratory complex I (ETCCI) or other mitochondrial (mt) electron transfer chain components (Bridges et al., 2014; Pollak, 2017). By increasing ADP:ATP ratio metformin activates AMPK and inhibits mTORC1, reducing hepatic glucose production (Duca et al., 2015) and enhancing autophagy, a homeostatic process that limits cell and tissue damage (Salminen and Kaarniranta, 2012). Autophagy/mitophagy curtails inflammation, in part, by limiting NLRP3 inflammasome activation (Sanchez-Lopez et al., 2019; Zhong et al., 2016). Sustained metformin administration reduced macrophage NLRP3 inflammasome activation in diabetic individuals, and in non-myeloid cells via an AMPK-dependent and poorly defined mechanism (Lee et al., 2013; Li et al., 2016; Yang et al., 2019). Downstream mediators connecting AMPK to the inflammasome and their role in the response to metformin were not investigated. AMPK was also suggested to inhibit IKK-mediated NF-kB activation in vascular endothelial cells and cardiomyocytes but the underlying mechanism and its relevance to NLRP3 inflammasome priming remain obscure (Hattori et al., 2006; Vaez et al., 2016). Metformin was also shown to inhibit NF-kB and cytokine induction in glia independently of AMPK (Labuzek et al., 2010), and ameliorate air-pollution induced thrombosis and IL-6 production by alveolar macrophages through ETCCI inhibition (Soberanes et al., 2019). Here Applicant shows that metformin treatment of non-diabetic mice blunts the severity of LPS-induced ARDS when given either before or after LPS challenge. Although metformin does not affect expression of TNF and many other cytokines and chemokines, it inhibits IL-6 and IL-1β secretion. Attenuation of IL-6 secretion is likely to be due to abrogated JNK and p38 MAPK activation and diminished recruitment of c/EBPβ and NFATc1-4 recruitment to the IL-6 promoter. Diminished IL-1β production, however, is caused by inhibition of NLRP3 inflammasome activation, correlating with reduced ox-mtDNA generation as a result of metformin-induced inhibition of mtATP production and LPS-induced ATP-dependent mtDNA synthesis. Myeloid-specific ablation of cytidine monophosphate kinase 2 (CMPK2), the LPS-inducible rate-limiting enzyme required for activation of the salvage pathway of mtDNA synthesis (Zhong et al., 2018), also reduces LPS-induced ARDS severity with little effect on IL-6 production. Neither NF-kB nor AMPK are involved in the ARDS protective activity of metformin. Of note, metformin also attenuated pulmonary inflammation in SARS-CoV2 infected human (h) ACE2 transgenic (Tg) mice. A myeloid cell targeted version of metformin, a safe and inexpensive drug, can be used in the treatment of ARDS and other severe inflammatory conditions.

Materials and Methods
Cell Lines and Primary Culture
Macrophage Culture and Stimulation Femurs and tibia bones from C57BL/6, p62$^{f/f}$, and p62$^{ΔΔMye}$(Zhong et al., 2016), Cmpk2$^{f/f}$ and Cmpk2$^{ΔΔMye}$ (generated in house), Ndsuf4$^{-/-}$ (kindly provided by Dr. Joshua D. Rabinowitz and Dr. Lifeng Yang), Ampkα1$^{-/-}$ (kindly provided by Dr. Ru Liu-Bryan), and Il10$^{-/-}$ mice collected at 8-10 weeks of age were used to generate bone-marrow-derived macrophage (BMDM) as described (Hornung et al., 2008). Macrophages were cultured in high glucose DMEM supplemented with 10% FBS, 20% L929-cell conditioned medium, and 100 U/ml penicillin-streptomycin for 7-10 days. Immortalized mouse BMDM (iBMDM) were obtained from Dr. Kate Fitzgerald and grown in DMEM supplemented with 10% FBS and 100 U/ml penicillin-streptomycin.

Primary microglia was isolated from BL6 mice as described (Saura et al., 2003). Briefly, confluent mixed glial cultures were subjected to mild trypsinization (0.05-0.12%) in the presence of 0.2-0.5 mM EDTA and 0.5-0.8 mM Ca$^{2+}$ to detach an intact layer of astrocytes, leaving attached microglia.

PBMC were isolated from fresh peripheral blood of healthy donors (StemExpress, Inc) by density gradient centrifugation using Ficoll-Paque PLUS (GE healthcare).

PBMC layer was collected and CD14$^+$ monocytes were purified by magnetic selection (StemCell Technology) according to the manufacturer's protocol. CD14$^+$ monocytes, with a final cell density of 10$^6$ cells/ml, were cultured in RPMI-1640 medium with L-glutamine and 25 mM Hepes (Hyclone), supplementation includes 100 μg/ml streptomycin, 100 U/ml penicillin (Thermo Fisher Scientific), 1× MEM non-essential amino acids (Hyclone), 1× (55 uM) 2-Mercaptoethanol (Thermo fisher Scientific) and 10% heat-inactivated fetal bovine serum (Hyclone) and 50 ng/mL human recombinant GM-CSF (R&D systems 215-GM-010). Medium containing GM-CSF was refreshed every 2-3 days by adding half of the initial volume. After 6 days, macrophages were harvested with Versene solution (Irvine Scientific cat. 9314) for 30 minutes (37 C, 5% CO2) and collected by cell scrapping. Cells were resuspended in RPMI-1640 media with 2 mM L-glutamine (Thermo Fisher) and supplemented with Hepes (25 mM, Hyclone), 1× penicillin/streptomycin (Thermo Fisher Scientific) and 1% heat-inactivated fetal bovine serum (Hyclone). 2.5×10$^4$ macrophages were seeded as triplicate wells in 96-well plate in a volume of 150 uL per well. After 4 hrs period of adaptation (37 C, 5% CO2), the indicated dose of Metformin (Tocris Bioscience) was added overnight for 16 hrs. Macrophages were then stimulated with 20 ng/ml of LPS for 3 hrs followed by addition of 2 mM ATP (Invivogen) for 30 min. Supernatants were collected and stored at −80 C. Cells were rinsed with PBS and processed for Caspase I activity by Flow cytometry.

All macrophages were cultured at 37° C. with 5% CO2. NLRP3 inflammasome activation was induced after 4 hrs priming with ultrapure LPS (100 ng/ml) by challenge with the NLRP3 activators ATP (4 mM) and nigericin (10 μM) for 1 hr, unless otherwise indicated, and monosodium urate (MSU) crystals (400 μg/ml) and alum (250 μg/ml) for 6 hrs.
Vero Cells Culture African green monkey kidney epithelial cells (Vero-E6, CRL-1586) were obtained from the American Type Culture Collection (ATCC, Bethesda, MD) and maintained in Dulbecco's modified Eagle medium (DMEM) supplemented with 5% (v/v) fetal bovine serum (VWR) and 100 units/ml penicillin-streptomycin (Corning).
Animal Studies Nine weeks-old C57BL/6 male mice purchased from Charles River Laboratories were maintained at a UCSD animal facility until alum-induced peritonitis and LPS-induced ARDS models were performed. All mouse studies were conducted in accordance with UCSD and NIH guidelines and regulations for the housing and treatment of laboratory animals using protocols approved by the UCSD Institutional Animal Care and Use Committee.

Myeloid specific Cmpk2 knockout (Cmpk2$^{ΔΔMye}$) mice were generated from C57BL/6N-Cmpk2tm1c(KOMP) Wtsi/H mice (MRC Harwell Institute), that harbor a targeted Cmpk2$^{Floxed}$ allele that can be inactivated by Cre-mediated recombination. Cmpk2$^{Floxed}$ homozygous mice were crossed with transgenic mice that expressed Cre recombinase under control of the lysozyme M (LysM) promoter to generate Cmpk$^{ΔΔMye}$.
Lps-Induced ARDS Ten- to twelve-weeks-old male C57BL/6 mice, Cmpk2$^{f/f}$ and Cmpk2$^{ΔΔMye}$ were subjected to LPS-induced ARDS as described (Yu et al., 2018). Briefly, 5 mg/kg LPS or vehicle was i.p. injected and the mice were euthanized 8, 24 or 48 hrs later. Metformin's prophylactic effect was evaluated by i.p. injections at 10 or 50 mg/kg for three consecutive days with the last dose administered 30 min prior LPS challenge.

Oral metformin prophylactic effect was evaluated by providing 400 mg/kg metformin in the drinking water ad libitum starting 2 days prior to LPS challenge and until the endpoint. Metformin's therapeutic effect was studied by i.p. injection at 50 mg/kg starting 30 min after LPS injection with a second dose given after 24 hrs. In all cases, at the experimental endpoint the lungs were inflated with cold PBS, excised and fixed in 10% formalin for histological evaluation.

Mice were also subjected to metformin pretreatment as above and injected with a lethal LPS dose (30 mg/kg). Survival was monitored up to 72 hrs and survival rate was determined by Kaplan Meyer analysis.

Alum-Induced Peritonitis

Ten- to twelve-weeks old male C57BL/6 mice were i.p. injected with alum (700 mg) or PBS. The mice were pretreated with metformin at 10 or 50 mg/kg 30 minutes prior to alum challenge. Peritoneal lavage was collected to measure cytokine amounts by ELISA.

Sars-CoV-2 Infection in hACE2 Mice

All the in vitro and in vivo experiments with infectious SARS-CoV-2 have been conducted under appropriated biosafety level (BSL) 3 and animal BSL3 (ABSL3) laboratories, respectively, at The Scripps Research Institute (TSRI). Experiments have been approved by the TSRI Institutional Biosafety (IBC) and Animal Care and Use (IACUC) committees.

K18 human-ACE2 B6 background male mice were subjected to intranasal infection with 100 ml volume containing 10,000 PFU of SARS-CoV-2 USA-WA1/2020 strain (Gen Bank: MN985325.1) following gaseous sedation in an isoflurane chamber. Mice were pretreated with vehicle or 50 mg/kg metformin daily starting 2 days before infection. Some mice were mock infected, treated with vehicle and used as healthy controls for scoring purposes. Body weight and general health status was monitored daily during the course of the experiment. At day 5 post-infection mice were euthanized by overdose of isoflurane and lung were inflated with 10% formalin for histopathological assessment.

Method Details shRNA Lentiviral Knockdown

ATG7, AMPKα1 and AMPKα2 knockdowns were done by lentiviral transduction of iBMDM or primary BMDM as described (Sanchez-Lopez et al., 2019). Sequences of specific shRNAs used in this study were obtained from the MISSION shRNA Library (Sigma). Viral particles were generated in HEK293T cells using VSV-G and pLV-CMVΔΔ8.9 plasmids and specific shRNAs. Supernatants were collected 48 hrs after transfection, filtrated through a 0.45 micron pore filter and added to iBMDM or primary BMDM. To increase infection efficiency, 8 mg/ml of polybrene were added. Virus containing medium was washed after 6 hrs and the cells were cultured with fresh medium. Infected cells were expanded and selected with puromycin at 72 hrs post-transduction.

Generation of SARS-CoV-2 USA-WA1/2020 Viral Stock

SARS-CoV-2 USA-WA1/2020 natural isolate was obtained from BEI Resources (NR-52281) and amplified on Vero E6 cells. Briefly, Vero-E6 cells were plated in T75 flasks with complete DMEM containing 10% FBS, 1× PenStrep, 2 mM L-Glutamine ON at 37° C. 5% CO2. The media in the flask was removed and SARS-CoV-2 strain USA-WA1/2020 (BEI Resources NR-52281) diluted (final volume 2 ml) in complete DMEM containing 2% FBS and added to the flask (MOI of 0.5) and was allowed to adsorb for 60 min at 37° C./5% CO2. After adsorption, the inoculum was removed and 15 mL of complete DMEM containing 2% FBS was added to the flask. Infection was allowed to proceed at 37° C./5% CO2 for 72 hrs. Supernatant was harvested and clarified at 1,000×g for 5 minutes. Clarified supernatant was filtered through a 0.22 µM filter and stored at −80° C. To determine virus titers Vero E6 cells ($10^6$ cells/well, 6-well plate format, triplicates) were infected with ten-fold serial dilutions of viral samples for 1 hr at 37° C. After viral adsorption, cells were overlaid with post-infection media containing 1% low melting agarose and incubated at 37° C. At 72 hrs pi, cells were fixed ON with 10% formaldehyde solution. The agarose plug was removed, and the fixed monolayer stained with 0.4% crystal violet in 20% methanol.

Protein Immunoblotting

Mitochondria were isolated using Mitochondria Isolation kit. Nuclear and cytosolic fractions were obtained using NE-PER™ Nuclear and Cytoplasmic Extraction Reagents. Whole cell lysates were prepared in RIPA buffer (25 mM Tris-HCl pH 7.6, 150 mM NaCl, 1% NP-40, 1% sodium deoxycholate, 0.1% SDS) containing a protease inhibitor cocktail (Roche, 11836153001) and a phosphatase inhibitor cocktail (Sigma-Aldrich, P5726). Protein concentrations were determined using BCA Protein Assay Kit (Pierce, 23225). Equal amounts of protein were separated by SDS-PAGE and transferred onto PVDF membranes, blocked in 5% BSA in 1× TBST for 1 hr and incubated with indicated antibodies overnight. Secondary antibodies were added for 1 hr and detection was done using Clarity™ Western ECL Substrate (Biorad).

Elisa (Engyme-Linked Inunosorbent Assay)

Paired antibodies (capture and detection) and standard recombinant mouse IL-1β (R&D Systems), and TNF and IL-6 (eBioscience) were used to determine mouse cytokine concentrations according to manufacturer's instructions.

Human 41-plex Luminex kit (EMD Millipore) was used to determine human cytokine and chemokine release by human macrophages according to the manufacturer's protocol. Samples were captured in the MAGPIX (Luminex XMAP Technology) using the XPONENT software. Raw data were analyzed with MasterPlex software using best fit curve method for each analyte and concentrations were calculated (pg/ml).

Caspase-1 ZYAD FLICA Staining

Stimulated macrophages were rinsed with PBS, and Caspase I activity detected with 1:60 dilution Caspase I FLICA dye (660-YVAD-FMK, Immunochemistry technologies, LLC) per manufacturer's instructions alongside GhostRED Live dead marker (Tonbo) for 30 min at 37° C. After staining, the cells were PBS rinsed, detached with Versene for 30 minutes on ice, resuspended in PBS and fluorescence intensity measured by flow cytometry on FACS CANTO II (BD biosciences). Data was analyzed in FloJo software after live singlet gating and Median florescent intensity (MFI) of each channel exported to excel and graphed in Prism.

Rna Isoladon and Quantitative Real-timePCR (QFCR)

RNA was extracted using AllPrep DNA/RNA Mini kit, and cDNA was synthesized using SuperScript™ VILO™ cDNA Synthesis Kit. mRNA expression was determined by QPCR in a CFX96 thermal cycler (Biorad) as described (Zhong et al., 2016). Data are presented in arbitrary units and calculated by the $2^{(-\Delta\Delta CT)}$ method. Primer sequences were obtained from the NIH qPrimerDepot (http://mousep-rimerdepot.nci.nih.gov) and provided by Integrated DNA technologies.

Chromatin Immunoprecipitation Assays

Cells were fixed using 0.75% formaldehyde for 10 min followed by 0.125 M glycine to stop the crosslinking reaction. After 5 min at room temperature, ice-cold PBS was added to the flasks and cells were scraped on ice, washed three times with PBS and then lysed for 10 min in A buffer (50 mM Tris, pH 8.0, 2 mM EDTA, 0.1% Nonidet P-40 and 10% glycerol) supplemented with containing a protease inhibitor cocktail (Roche, 11836153001) and a phosphatase inhibitor cocktail (Sigma-Aldrich, P5726). Nuclei were pelleted at 1,000 g in a cold microfuge and resuspended in B buffer (50 mM Tris, pH 8.0, 5 mM EDTA and 1% SDS plus inhibitors). Chromatin was then sheared by sonication (six rounds of 15 s pulses each, at 50% of the maximum potency of ultrasonic homogenizer), centrifuged to pellet debris and finally 10× diluted in dilution buffer (50 mM Tris, pH 8.0, 0.5% Nonidet P-40, 0.2 M NaCl and 5 mM EDTA). Nuclear extracts were immunoprecipitated with respective antibodies. The co-immunoprecipitated material was then subjected to qPCR analysis using specific primers.

Immunofluorescence and Confocal Microscopy

BMDM were fixed in 4% paraformaldehyde (PFA), permeabilized in 0.02% Triton X-100, and blocked in 1× PBS supplemented with 2% BSA and 5% normal horse serum. Primary antibodies were incubated in blocking buffer at 4° C. overnight. Secondary Alexa antibodies from Life Technologies or Jackson Immuno Research Laboratories were added for 1 hr. Nuclei were counterstained with DAPI. Samples were imaged through a Leica SP5 confocal microscope.

To image mtDNA synthesis, BMDM were stimulated with LPS (1 mg/ml) for 4 hrs in the presence of 10 μM EdU. Cells were then washed twice with sterile PBS and fixed in 4% PFA for 15 min followed by permeabilization with 0.02% Triton X-100 for 10 min. EdU staining was performed using a Click-iT EdU Microplate Assay Kit (Thermo Fisher Scientific). In brief, BMDMs were postfixed in EdU fixative for 5 min, and equal volumes of the EdU reaction cocktail, which was prepared immediately before use, were added to each chamber and left overnight. Primary antibody against the mitochondrial marker Atp5b was included in the EdU reaction cocktail. The next day, the BMDM were washed three times with PBS followed by incubation with secondary Alexa antibodies from Life Technologies or Jackson Immuno Research Laboratories. DAPI was used for nuclear counterstaining.

Histological Evaluation and Immunohistochemistry

Lungs were fixed in 10% formalin for 24 hrs and embedded in paraffin, sectioned and stained with hematoxylin and eosin (H&E) to evaluate gross morphology and lung damage and inflammation; and with Sirius red to determine collagen buildup. Ten to twelve H&E stained sections from each animal were scored for the degree of lung inflammation and damage by two blinded mouse lung pathology experts as described (Jupelli et al., 2013), and the scores were averaged. Briefly, the degree of lung inflammation was assigned an arbitrary score of 0 (normal=no inflammation, no airway thickening, no edema), 1 (minimal cellular infiltration, and minimal edema), 2 (mild-moderate cellular infiltration, plus mild airway thickening and mild edema), 3 (severe cellular infiltration, plus diffuse airway thickening and severe edema) in 10-12 fields per mouse.

Lung sections were subjected to incubation with antibodies specific for F4/80 (macrophage marker), myeloperoxidase (MPO, neutrophil marker), c/EBPb, NFATc2 and NFATc3. Stained areas were quantified using ImageJ software.

NLRP3 inflammasome activation in the lung was detected by immunofluorescence co-staining with F4/80 and ASC antibodies. Briefly, lung sections were hydrated and boiled at 96° C. in citrate buffer 1× for 20 min. Sections were blocked with 2% BSA/PBS1X containing 1% normal horse serum for 1 hr at room temperature. F4/80 and ASC antibodies were incubated in blocking solution overnight at 4° C. After washing, Alexa secondary antibodies were added and the sections were incubated in 2% BSA/PBS1X for 1 hr at room temperature. Sections were washed, incubated with DAPI, and mounted using FluoSave. Sections were imaged through a Leica SP5 confocal microscope. The percentage of F4/80$^+$ cells with ASC specks were quantified in 18-26 high magnification fields from 4-5 mice per group.

LC-MS/MS for Measuring Metformin Concentration in Plasma

Metformin has high apparent volume of distribution and the protein binding is negligible. Therefore, simple protein precipitation was utilized for plasma metformin extraction. Pooled mice plasma (CD-1 (ICR) MSE00PLK2, BioIVT) was selected as blank matrix for standards and quality control samples. Sample preparation procedure was adopted from literatures with minor modifications. In brief, to 20 μL of blank pooled plasma or mouse plasma samples, 20 μL of 50% methanol-water or standard solutions were added followed by addition of 360 μL of ice-cold acetonitrile solution containing IS (111 nM metformin-D6). The samples mix were vortexed for 2 minutes then sonicated for 1 min and centrifuged at 6100 g for 10 min. Supernatants were transferred into a new set 96-well plate, and 10 μL were injected for LC-MS/MS analysis. A 2 μg/ml metformin stock solution was prepared in 50% methanol-water. The solution was then serially diluted with 50% methanol-water to obtain standard working solutions over a concentration range of 10-2000 ng/ml. The quality control (QC) samples were prepared in three concentrations: 10, 100, and 500 ng/ml.

LC-MS/MS system was performed using an Agilent 1290 Infinity HPLC and HiPALS (Autosampler) coupled with AB Sciex 6500 Q-Trap mass spectrometer. All data were acquired using Analyst (AB SCIEX v1.7.1). Metformin from mice plasma samples were separated on a Waters XBridge Amide column (2.1×150 mm, 3.5 μm) at 40° C. The mobile phase A was 20 mM ammonium acetate buffer in water and 100% acetonitrile as mobile phase B. A total 7 min gradient run with a flow rate of 0.8 ml/min was implemented. The chromatographic runs started with 95% mobile phase B for 2 min, then gradually increased mobile phase A from 5% to 95% in 1.5 min, kept the phase A at 95% for 1 min and reduced to 5% in 1.5 min, finally equilibrate the column at 95% phase B for 2 min. The mass spectrometer was operated in a positive mode using scheduled multiple reaction morning (sMRM). The ion source parameters were as follow: curtain gas (CUR) at 37, collision gas (CAD) at high, ionspray voltage (IS) at 5 kV, temperature (TEM) at 500, ion source gas 1 (GS1) at 60, ion source gas 2 (GS2) at 50, MRM detection window at 120 sec, target scan time (per sMRM expt) at 0.15 s, the retention time (RT) for both metformin and metformin-D6 were at 3.26 min, Q1 were 130.2 and 136.2 for metformin and metformin-D6 respectively, Q3 was 60.2, declustering potential (DP) at 100, collision energy (CE) at 13, entrance potential (EP) at 10, and collision cell exit potential (CXP) at 17.

Immunofluorescence and Analysis of Lung Samples from Human Autopsies

Tissues were obtained from autopsy of 11 patients with PCR confirmed SARS-CoV-2 and death due to COVID-related pneumonia and diffuse alveolar damage. Lung tissue from 3 patients with death due to non-pulmonary-related causes and no evidence of pneumonia or other pulmonary histopathological abnormalities were used as control. Tissues were fixed in 10% buffered formalin and paraffin embedded (FFPE). Immunofluorescence staining was performed on the Ventana Discovery Ultra instrument (Roche). Tissue sections were deparaffinized and antigen retrieval was performed using citrate buffer (pH=8.0) at 72° C. (CC1; Roche). Tissue sections were first probed with rabbit anti-ASC (AG-25B-0006, AdipoGen) followed by anti-Rabbit HRP (760-4311, Roche) and fluorescent visualization using tyramide signal amplification (Red610, Roche). Residual peroxidase was blocked (760-4840, Roche), followed by application of mouse anti-CD68 (KP-1, Roche), OmniMap anti-mouse HRP (Roche) and visualization using Discovery Rhod6G (Roche).

Representative immunofluorescence images were acquired using a Leica DMi8 microscope and for analysis the slides were scanned using a Zeiss AxiosScan Z1. Staining and imaging were performed by the Cedars-Sinai Biobank and Translational Research Core. ASC speck quantification was performed using open source QuPath software (version 0.2.3)(Bankhead et al., 2017).

Mitochondrial Function

Mitochondrial membrane potential was measured using TMRM according to manufacturer's instructions. Briefly, BMDM were primed or not with LPS for 4 hrs, and further stimulated with ATP or nigericin for 30 min. Cells were incubated with 200 nM TMRM for 30 min at 37° C. After washing twice, fluorescence intensity was determined per manufacturer's instructions using a FilterMax F5 multimode plate reader (Molecular Devices). Mitochondrial reactive oxygen species (mtROS) were measured using MitoSOX (Invitrogen) as described (Sanchez-Lopez et al., 2019). Metformin-pretreated BMDM were primed with LPS for 4 hrs and stimulated with NLRP3 inflammasome activators for 30 min. Cells were loaded with 4 µM MitoSOX for 20 min. After washing with PBS twice, cells were resuspended in PBS and counted. Equal numbers of cells from different treatment groups were then plated onto 96-well plates for fluorescence reading to minimize variation among treatment groups.

Fluorescence intensity was determined at 510/580 nm using a FilterMax F5 plate reader (Molecular Devices). Cellular ATP was measured after 4 hrs LPS stimulation using CellTiter-Glo Luminescent Assay (Promega) as described (Ip et al., 2017).

Measurement of Total mtDNA

Macrophages were primed with LPS (200 ng/ml) for 4 hrs, with or without 0.5 mM metformin pre-treatment for overnight. Total DNA was isolated using Allprep DNA/RNA Mini Kit (catalogue 80204, Qiagen) according to manufacturer's instructions. mtDNA was quantified by qPCR using primers specific for the mitochondrial D-loop region, cytochrome c oxidase (COX) or a specific region of mtDNA that is not inserted into nuclear DNA (non-NUMT) (Zhong et al., 2018). Nuclear DNA encoding Teri, 18S ribosomal RNA and B2m was used for normalization.

Cellular Fractionation and Measurement of Cytosolic mtDNA

Metformin-treated BMDM were primed with LPS and stimulated with NLRP3 inflammasome activators. Cellular fractionation was performed using Mitochondrial Isolation kit (89874, ThermoScientific) according to manufacturer's instructions. Cytosolic mtDNA was analyzed as described (Nakahira et al., 2011). For the measurement of Ox-mtDNA, mtDNA was first purified using Allprep DNA/RNA mini kit (Qiagen) from the cytosolic fraction of BMDM as described above. The 8-OH-dG content of the mtDNA was then quantified using an 8-OHdG quantification kit (ab201734), per manufacturer's instructions.

POLγ Activity Assay

Macrophages were pre-treated with 0.5 mM metformin overnight, followed by LPS (200 ng/ml) priming for 4 hrs. Whole cell lysates were prepared in RIPA lysis buffer and POLg activity was measured using DNA Polymerase Gamma Assay Kit (ProFoldin, DPG100K) per manufacturer's instruction.

Quantification and Statistical Analysis

Data are shown as average ±SD or average ±SEM, as indicated. Statistical significance was determined using two-tailed Student's t-test, and p values lower than 0.05 were considered statistically significant. For mouse data analysis, Mann-Whitney test was used when comparing two groups and ANOVA Kruskal-Wallis test when all groups were compared to each other. GraphPad Prism 8 was used for statistical analysis and graphing.

Metformin and Inflammatory Cytokine mRNA Expression

Figure 1A:
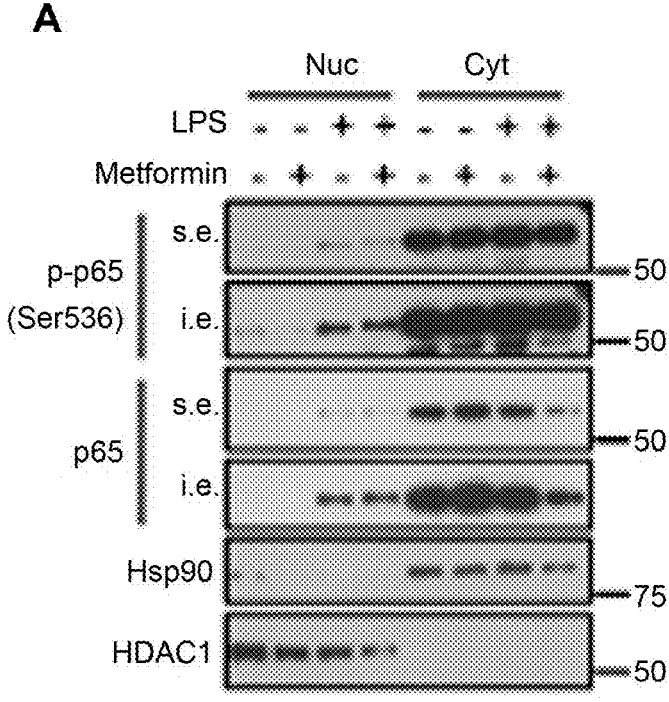
FIGS. 1A-1E: Metformin attenuates Il1b and Il6 mRNA induction but does not inhibit NF-kB activation (FIG. 1A) BMDM pretreated –/+ metformin (0.5 mM, 16 h) were harvested 30 min after LPS (100 ng/mL) addition. Nuclear (Nuc) and cytosolic (Cyt) fractions were analyzed for the indicated proteins. s.e., short exposure: l.e., long exposure. One representative immunoblot (IB) out of 2.
Figure 1B:
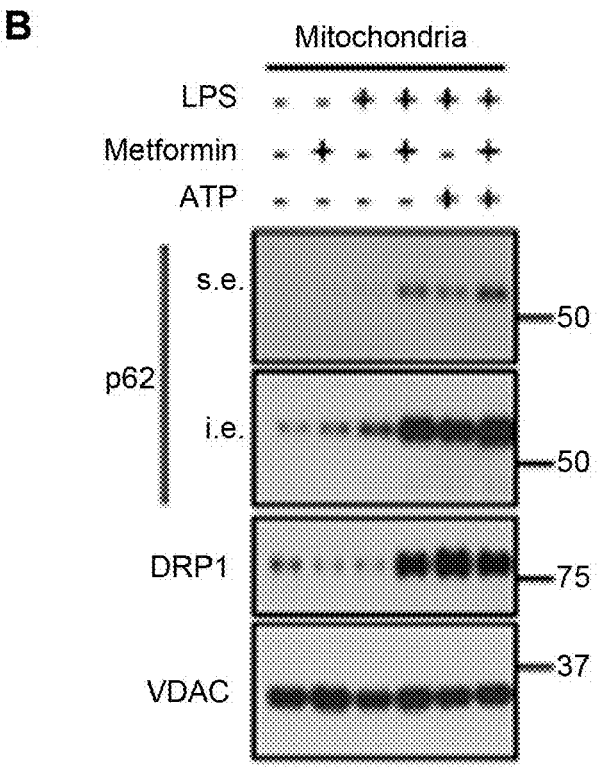
Figure 1C:
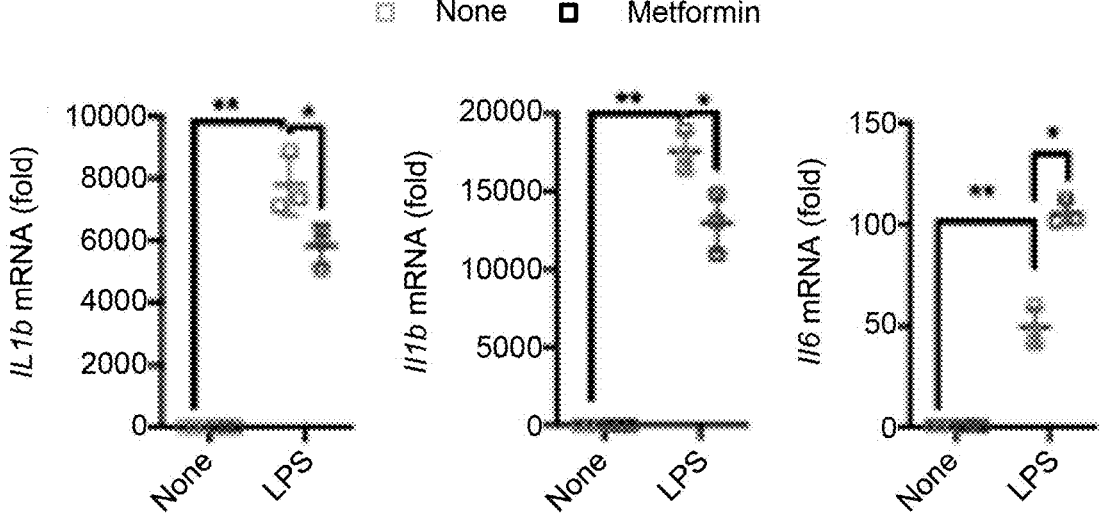
Figure 8A:
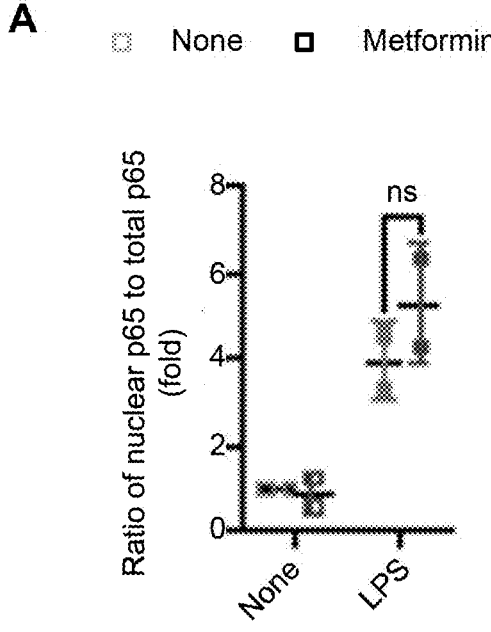
FIGS. 8A-8O: Effect of metformin on different cytokines and chemokines, related to FIG. 1.
Figure 8B:
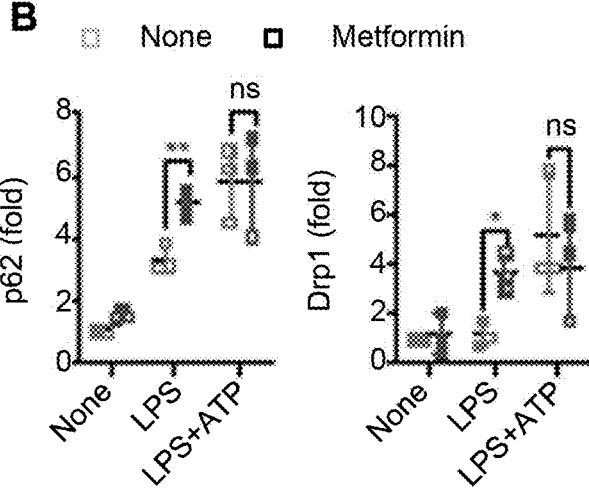
(FIG. 8B) Relative p62 and Drp1 amounts in mitochondria isolated from BMDM treated as in FIG. 1B (n=3).
Figure 8C:
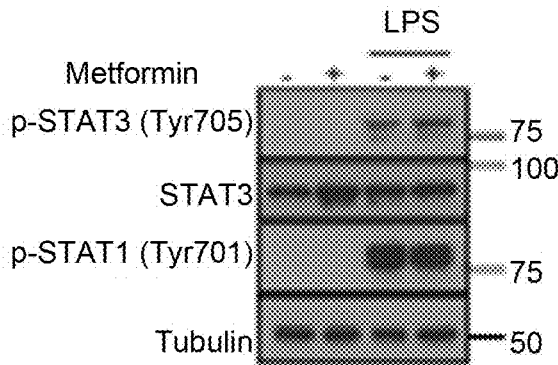
(FIG. 8C) IB analysis of phosphorylated STAT3 and STAT1 in lysates from BMDM pretreated –/+ metformin and stimulated with LPS. One representative IB out of 3 is shown.
Figure 8D:
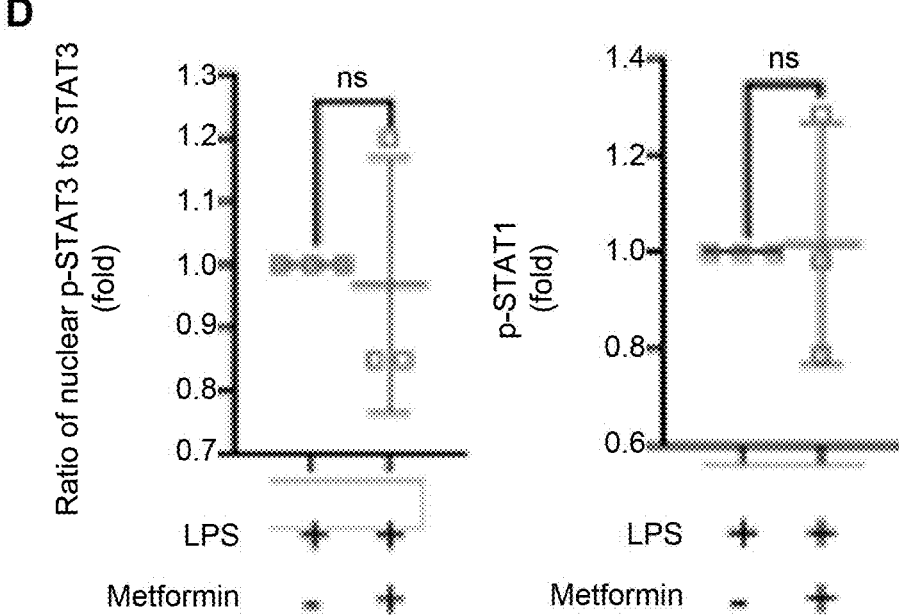
(FIG. 8D) Relative phosphorylated STAT3 and STAT1 amounts in BMDM stimulated as in (FIG. 8C) (n=3).
Figure 8E:
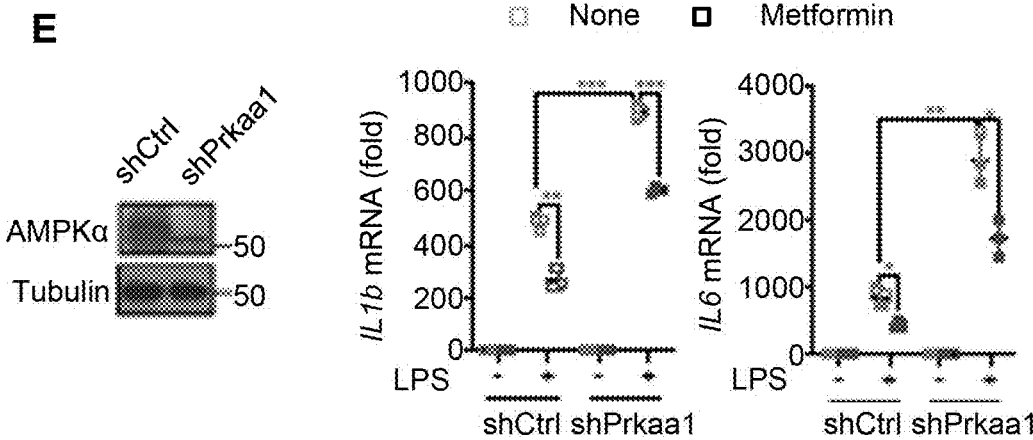
(FIG. 8E) Q-PCR quantitation of Il1b and Il6 mRNAs (right) in shCtrl and shPrkaa1 (AMPKα1) primary BMDM pretreated or not with metformin (0.5 mM, 16 hrs) and stimulated with LPS (100 ng/ml) for 4 hrs. The left panel shows a blot that demonstrates knockdown efficiency (n=3).
Figure 8F:
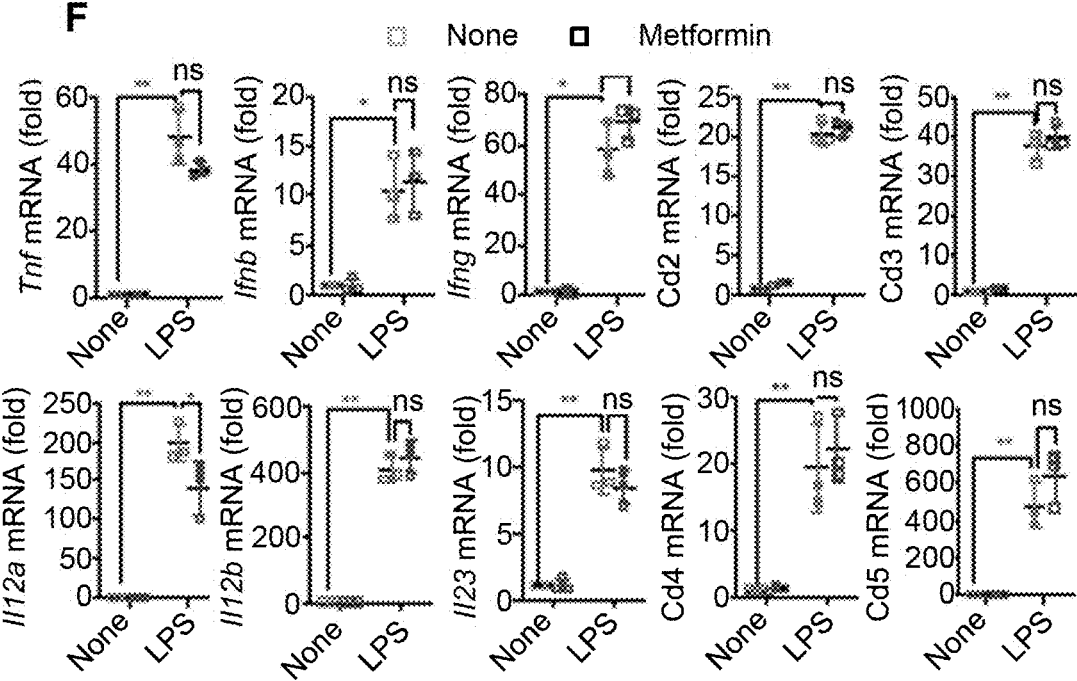
(FIG. 8F) Q-PCR quantitation of the indicated cytokine, chemokine and interferon mRNAs before or after LPS (100 ng/ml, 4 hrs) stimulation, –/+ metformin (0.5 mM, 16 hrs) pretreatment (n=3).
Figure 8G:
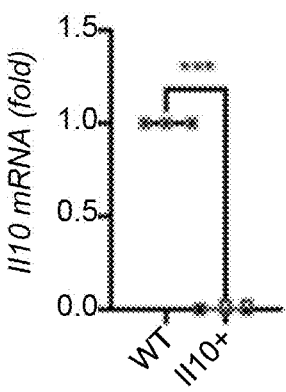
(FIG. 8G) Q-PCR quantitation of Il10, Il1b and Il6 mRNAs in WT and Il10–/–BMDMs treated as indicated (n=3).
Figure 8G:
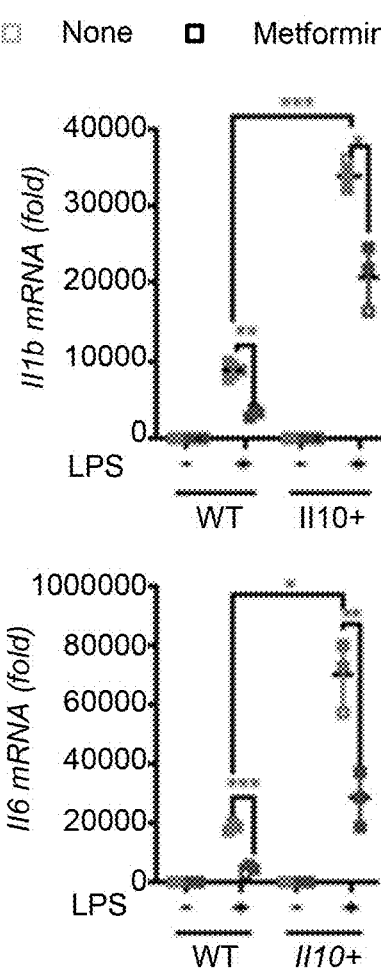

In an expansion of the work described in Experiment No. 1 and to understand the basis for metformin's anti-inflammatory activity Applicant examined its effect on macrophage NF-kB activation and cytokine gene induction in macrophages. Mouse bone marrow derived macrophages (BMDM) were incubated overnight with or without metformin (0.5 mM) and stimulated with LPS minus or plus ATP. In contrast to previous reports, metformin did not interfere with LPS-induced p65/RelA nuclear translocation or phosphorylation (FIG. 1A and FIG. 8A). Metformin also did not affect recruitment of the autophagy chaperon p62, encoded by the NF-kB-induced Sqstm1 gene, to mitochondria after LPS+ATP stimulation and enhanced it in LPS-primed cells that were not ATP exposed (FIG. 1B and FIG. 8B). Metformin had similar effects on recruitment of the mitochondrial fission dynamin GTPase DRP1, enhancing it in LPS primed cells and not affecting it in LPS+ATP challenged macrophages (FIG. 1B and FIG. 8B). Enhanced p62 and DRP1 recruitment may be the consequence of reduced ATP production and partial mitochondrial membrane depolarization in metformin treated cells (see below). Metformin did not inhibit STAT1 or STAT3 phosphorylation (FIG. 8C and FIG. 8D). Despite having no effect on NF-kB or STAT3, metformin led to a 30-50% decline in Il1b and Il6 mRNA induction by LPS (FIG. 1C). Curiously, AMPKα1 silencing enhanced Il1b and Il6 mRNA accumulation in LPS-treated macrophages but both transcripts still declined after metformin treatment (FIG. 8E). As reported (Kelly et al., 2015), metformin potentiated induction of Il10 mRNA (FIG. 1C), but had little effect on other cytokine and chemokine mRNAs, many of which are NF-kB responsive, including Tnf, Il12, Il23, Ccl2, Ccl3, Ccl4 and Ccl5 (FIG. 8F). Metformin did not inhibit induction of Ifnb and Ifng mRNAs, either (FIG. 8F). IL-10 induction was proposed to contribute to metformin's anti-inflammatory activity (Kelly et al., 2015; Park et al., 2019). However, despite enhanced Il1b and Il6 mRNA induction in LPS-stimulated Il10$^{-/-}$ BMDM, metformin still inhibited their expression (FIG. 8G). Metformin-enhanced Il10 mRNA expression was AMPK-dependent (FIG. 8H), but neither AMPK nor IL-10 were needed for the inhibitory effect on Il1b mRNA (FIG. 8E and FIG. 8G).

Metformin inhibited IL-6 secretion by LPS-stimulated BMDM, but TNF release was unaffected (FIG. 8I and FIG. 8J). A similar effect was seen in human peripheral blood mononuclear cells (PBMC) derived macrophages (FIG. 8K).

Figure 1D:
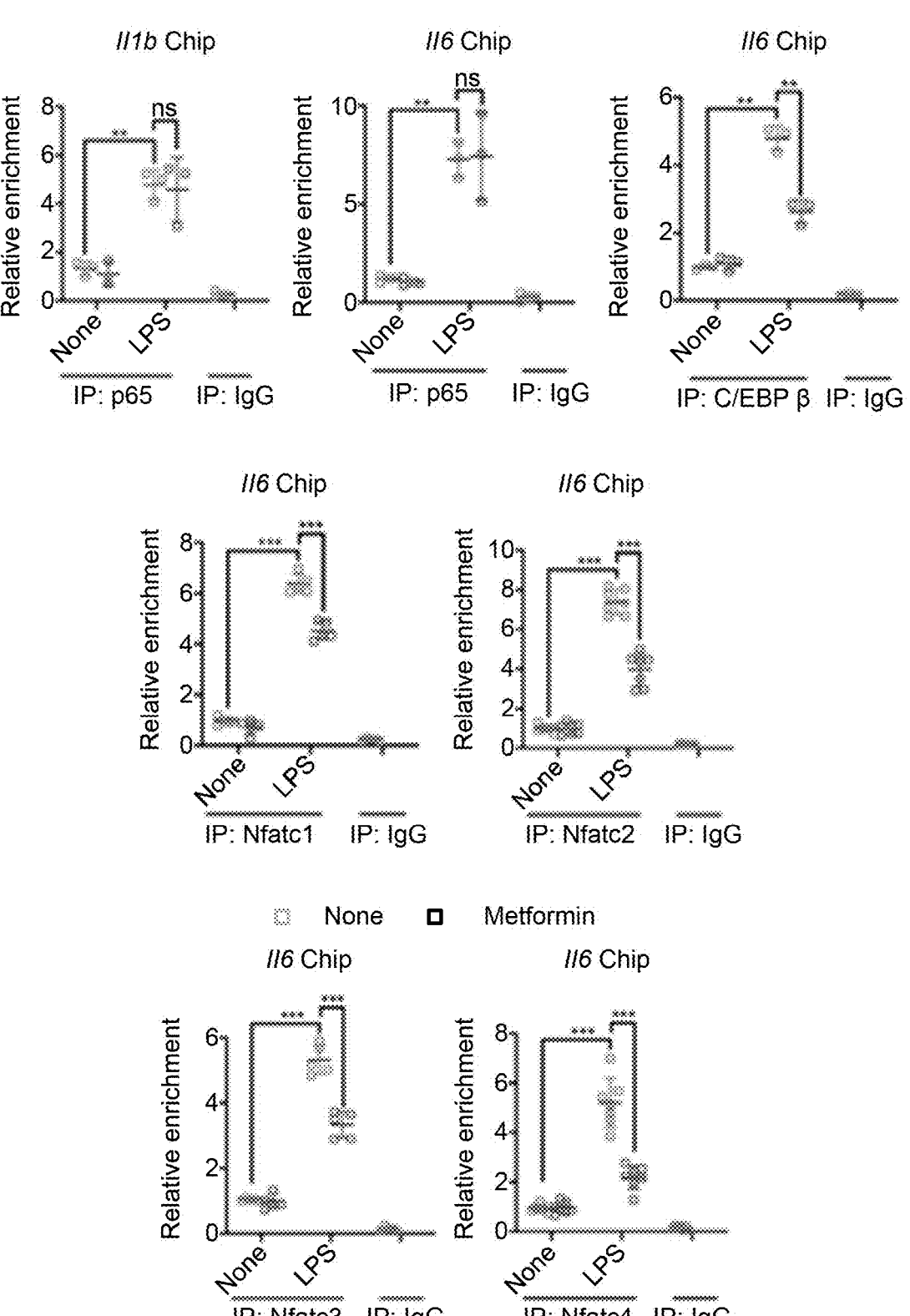
Figure 1E:
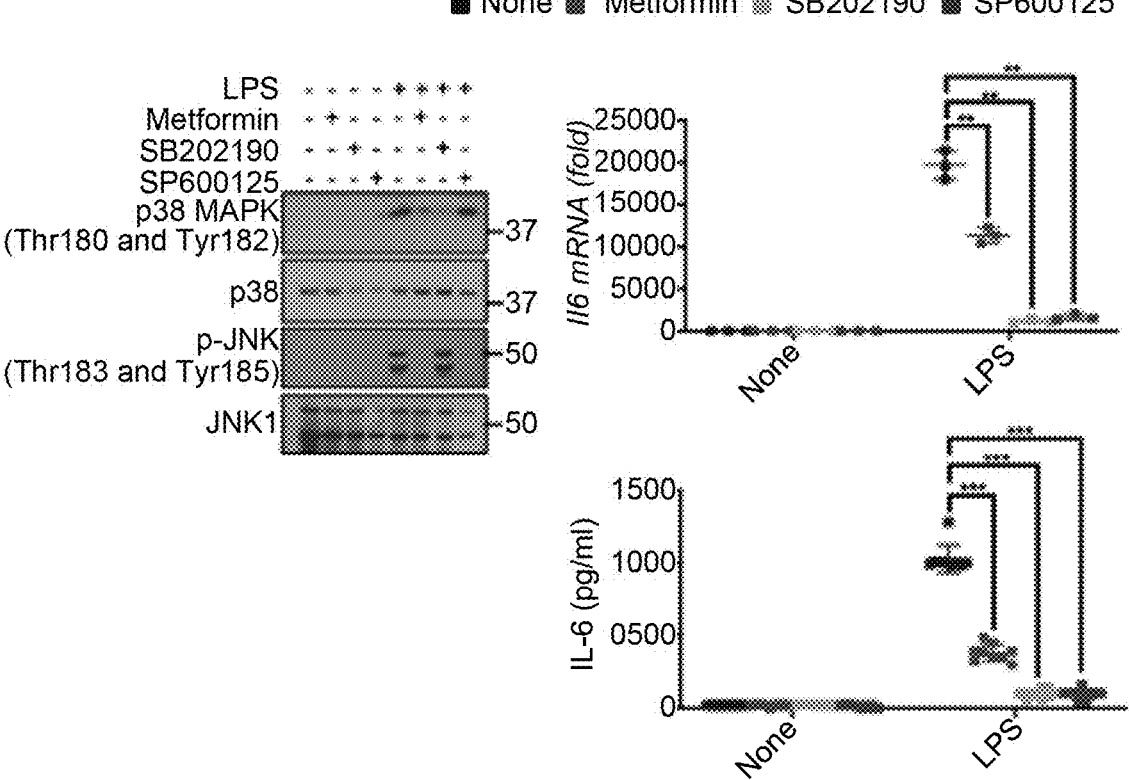
Figure 8L:
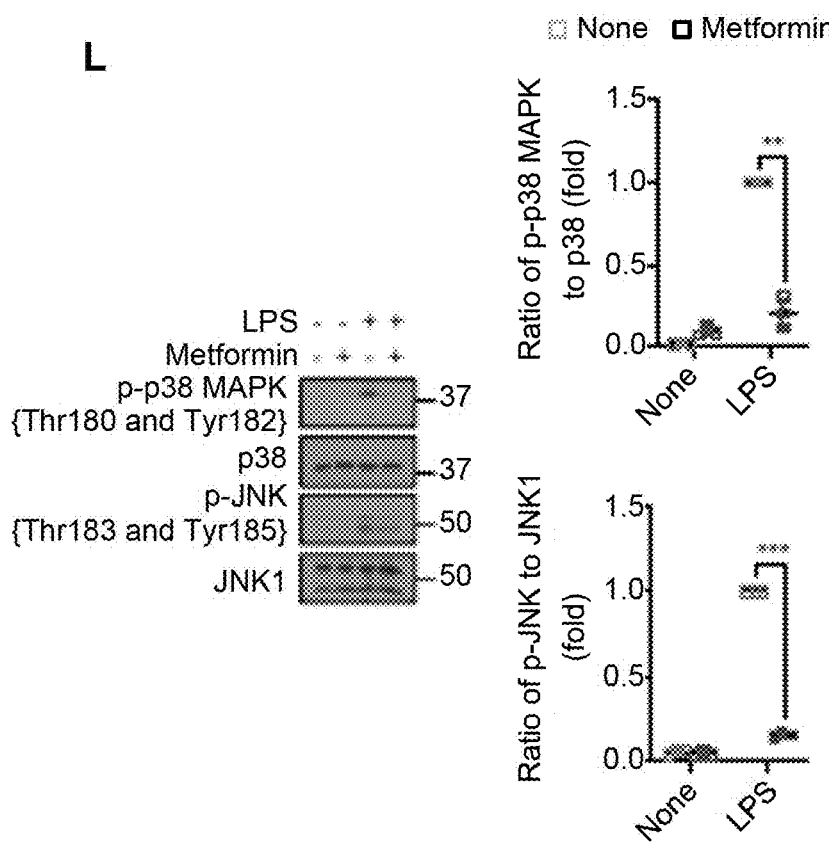
(FIG. 8L) IB analysis for p38 MAPK and JNK phosphorylation (left) and quantitation (right) in BMDM pretreated with metformin (0.5 mM, 16 hrs) stimulated with LPS (100 ng/ml) for 30 min. One representative IB out of 3 is shown.
Figure 8M:
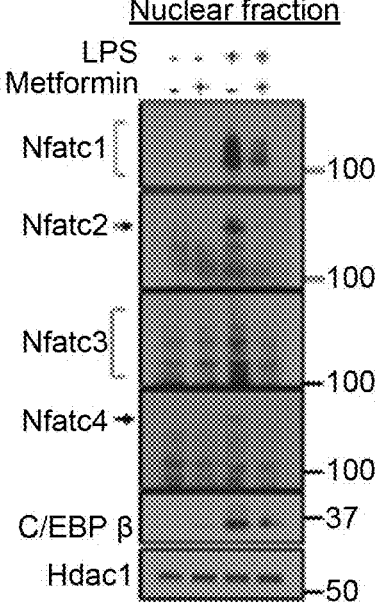
(FIG. 8M) IB analysis of indicated transcription factors in nuclear fractions from BMDM pretreated –/+ metformin (0.5 mM, 16 hrs) and stimulated with LPS (100 ng/ml, 4 hrs). HDAC1 was used as a loading control. One representative IB out of 3 is shown.
Figures 8N, 8O:
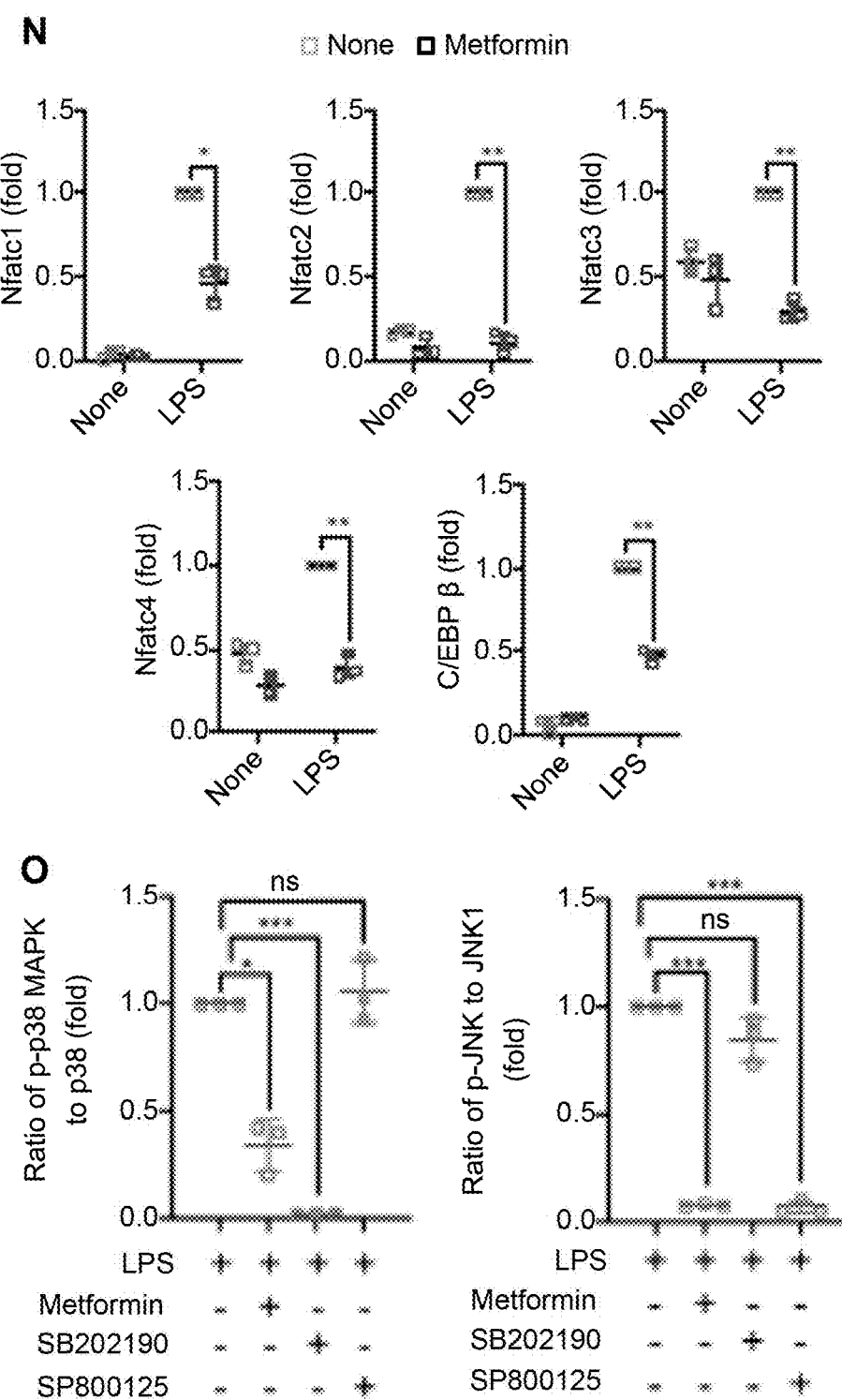
(FIG. 8N) Relative amounts of NFATc1, NFATc2, NFATc3, NFATc4 and c/EBPβ in BMDM treated as in (FIG. 8M) (n=3).

Inhibition of IL-6 production correlated with blunted p38 or JNK MAP kinase activation and decreased nuclear translocation of NFAT family members and c/EBPb (FIG. 8L-FIG. 8N), transcription factors that mediate Il6 gene induction (Akira et al., 1990; Luo and Zheng, 2016; Soberanes et al., 2019; Trautwein et al., 1993). Metformin also inhibited c/EBPβ and NFATc1-4 recruitment to the Il6 promoter but had no effect on p65/RelA recruitment to either the Il6 or Il1b promoter (FIG. 1D). In concordance with the above results, JNK (SP600125) and p38 (SB202190) inhibitors blocked Il6 mRNA induction and IL-6 secretion (FIG. 1E and FIG. 8O).

Metformin Inhibits NLRP3 Inflammasome Activation

Figure 2A:
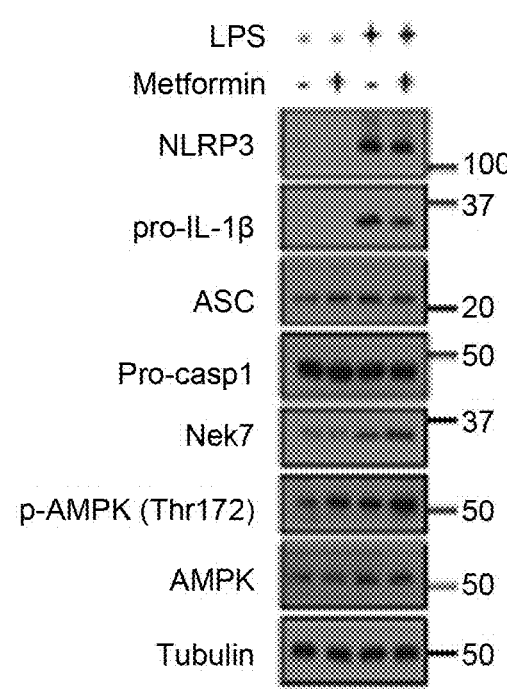
FIGS. 2A-2F: Metformin inhibits NLRP3 inflammasome activation (FIG. 2A) IB analysis of NLRP3, pro-IL-1b, ASC, procaspase-1, NEK7, phosphorylated AMPK, and total AMPK in BMDM pre-treated –/+ metformin (0.5 mM, 16 h) before or after 4 h of LPS (100 ng/mL) stimulation. Tubulin shows loading control.
Figure 2B:
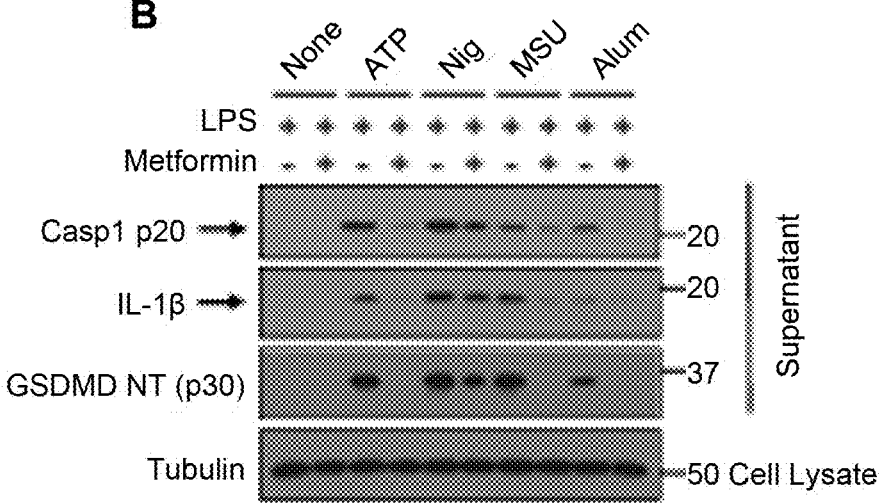
Figure 2C:
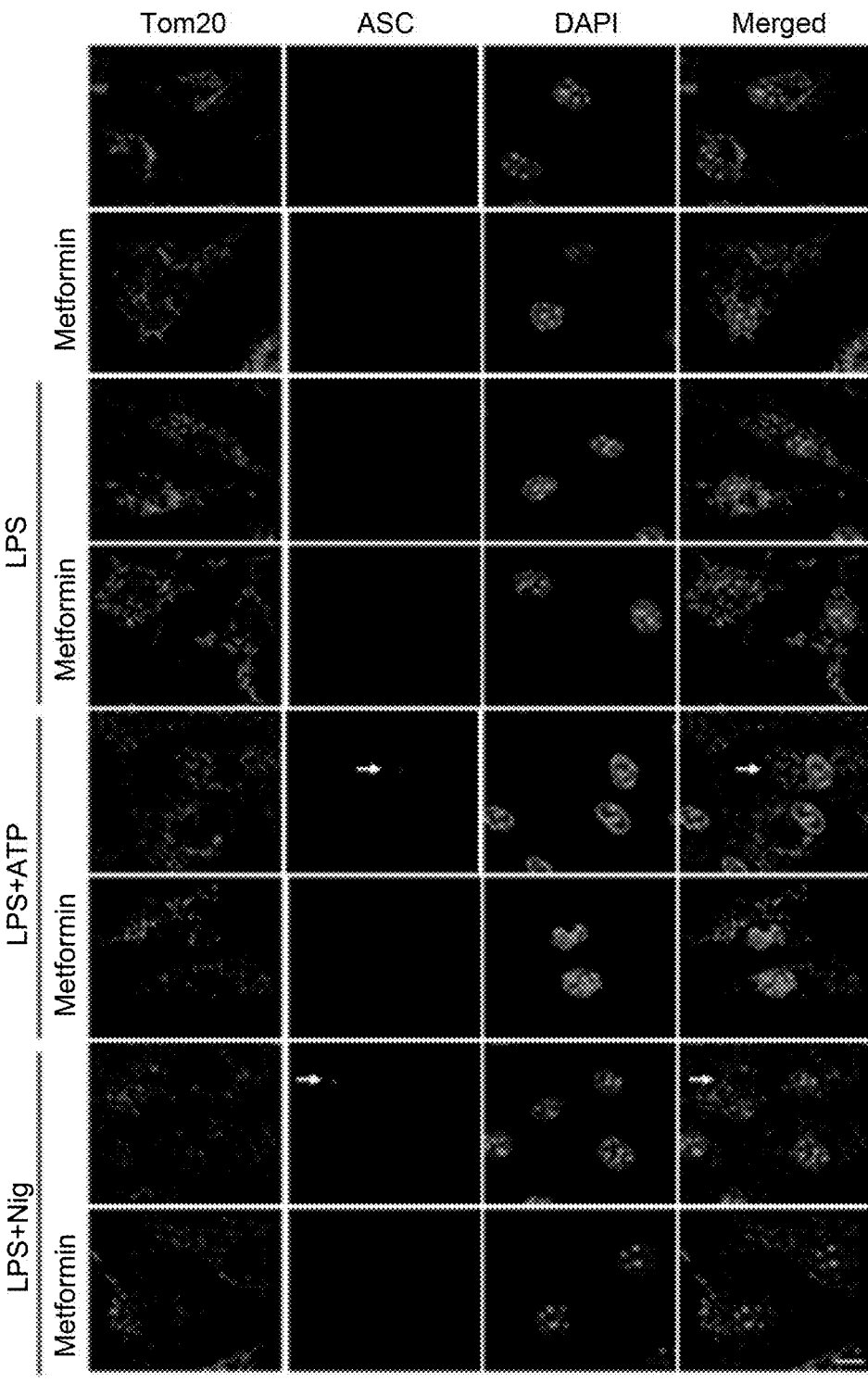
Figure 2D:
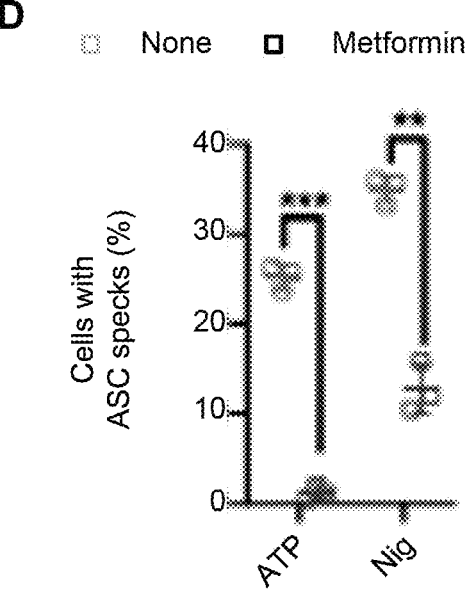
Figures 9A, 9B:
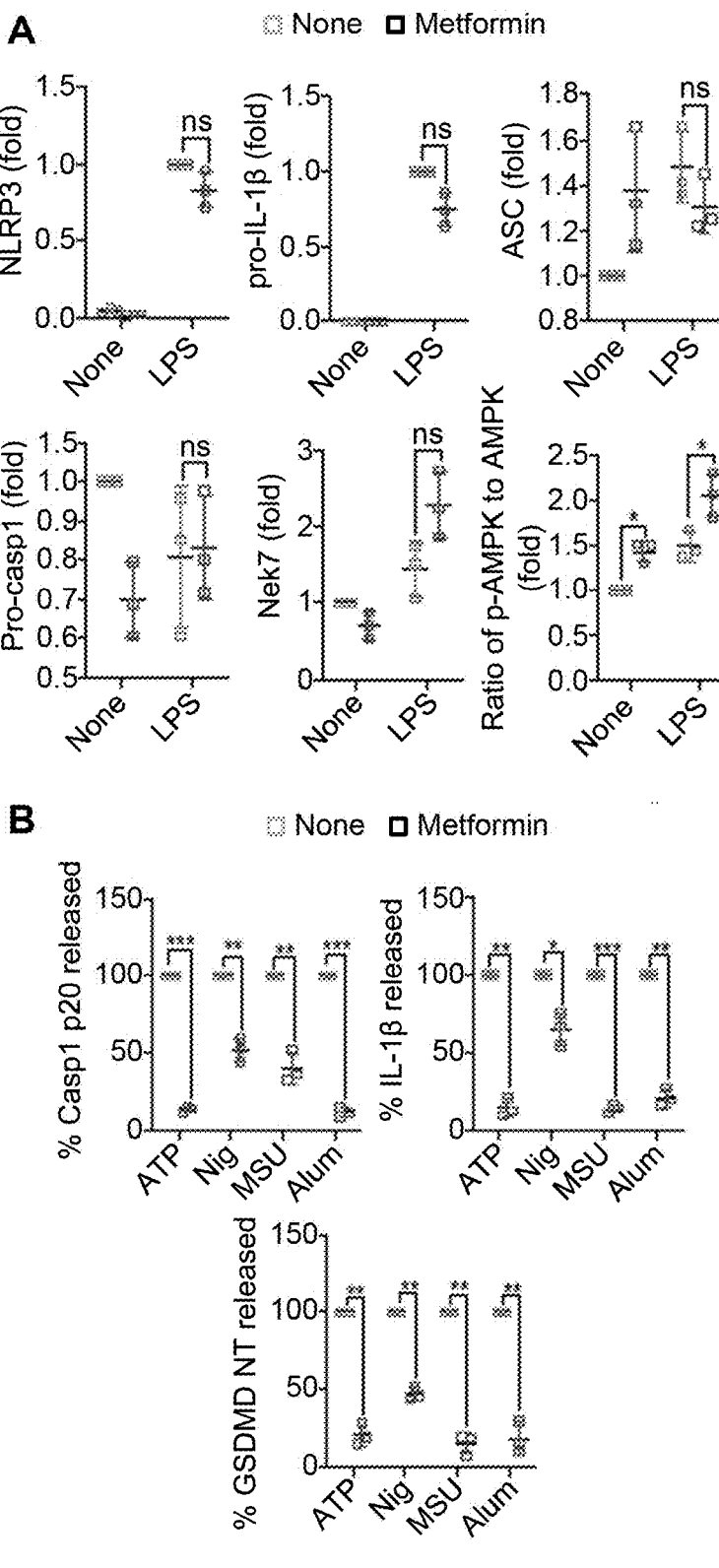
Figures 9G, 9H, 9I, 9J:
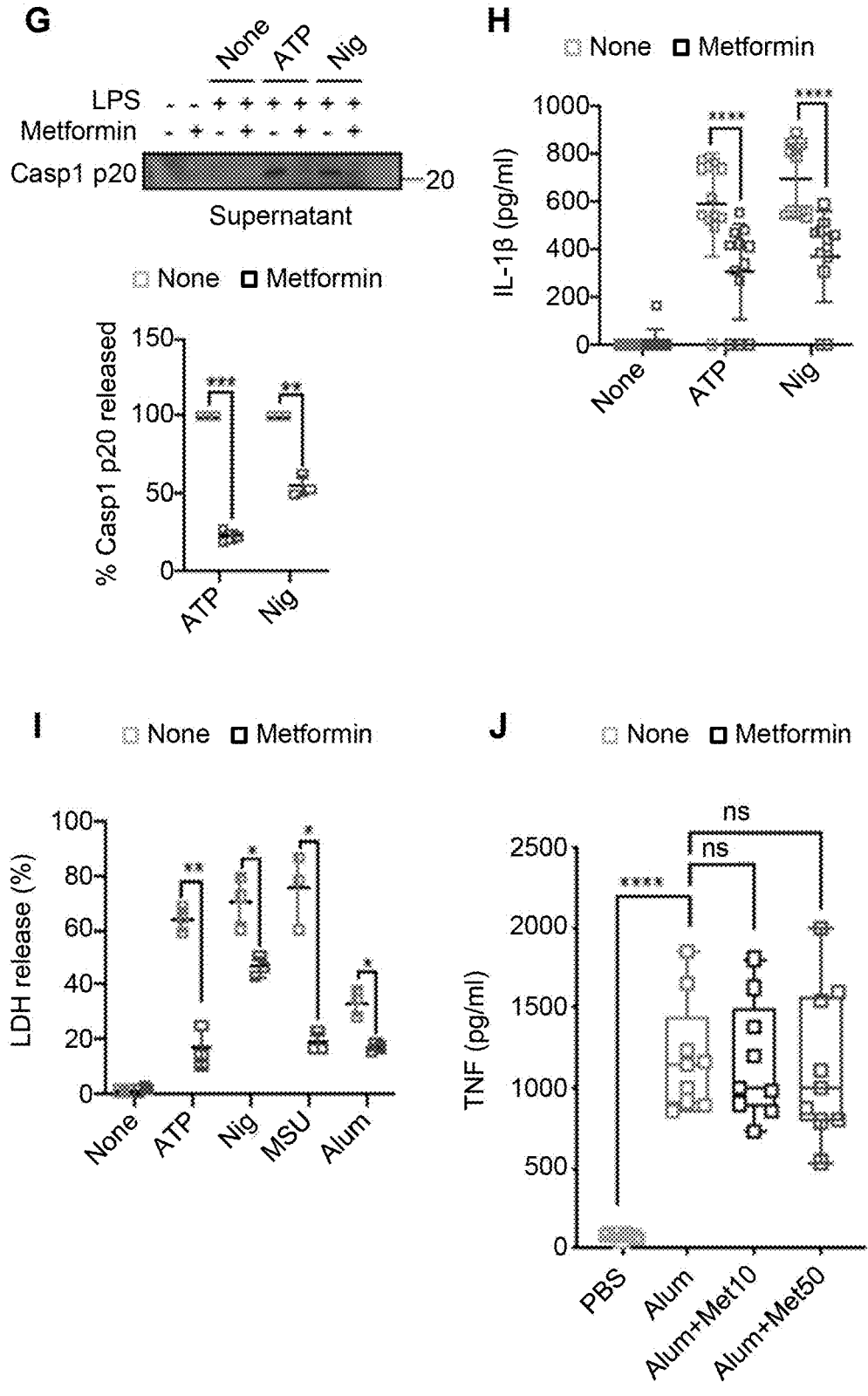

Metformin modestly decreased pro-IL 1β protein and had no effect on expression of the inflammasome components NLRP3, which was induced by LPS stimulation, ASC, pro-Casp1 and NEK7 (FIG. 2A and FIG. 9A). As expected, metformin increased AMPK phosphorylation. Importantly, metformin inhibited Casp1 activation and pro-IL-1β processing to mature IL-1β in LPS-primed macrophages incubated with either ATP, nigericin (Nig), alum or monosodium urate (MSU), although the effect on nigericin-challenged macrophages was relatively modest (FIG. 2B and FIG. 9B-FIG. 9D). Metformin also inhibited gasdermin D (GSDMD) cleavage (FIG. 2B and FIG. 9B), and abrogated Casp1 p20 and IL-1β secretion from human macrophages and LPS-primed mouse microglia stimulated with different NLRP3 inflammasome activators (FIG. 9E-FIG. 9H). To validate NLRP3 inflammasome inhibition Applicant assessed metformin's effect on ASC speck formation, an indicator of inflammasome assembly (Dick et al., 2016). Consistent with its effect on Casp1, metformin inhibited nigericin- and ATP-induced ASC speck formation, although inhibition of nigericin-induced specks was incomplete (FIG. 2C and FIG. 2D), correlating with residual inflammasome activation in nigericin stimulated cells. In concert with its ability to inhibit GSDMD processing and block production of its pore forming N-terminal fragment (Liu et al., 2016), metformin also reduced LDH release (FIG. 9I).

Figure 2E:
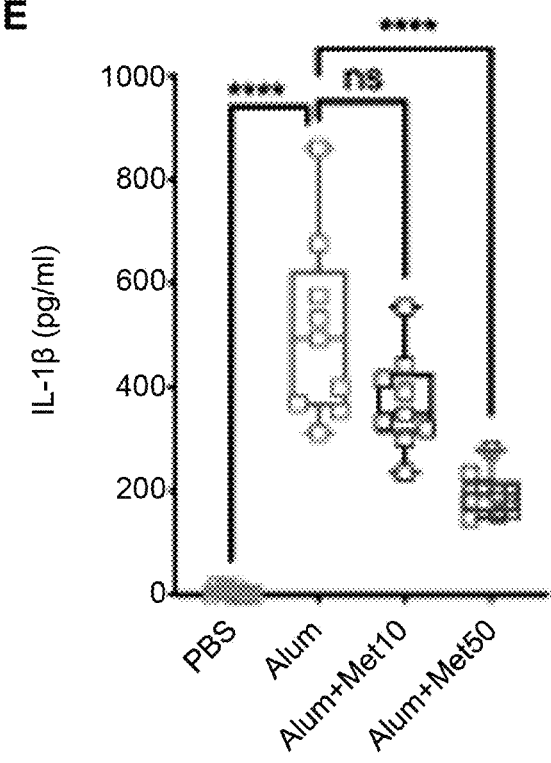
Figure 2F:
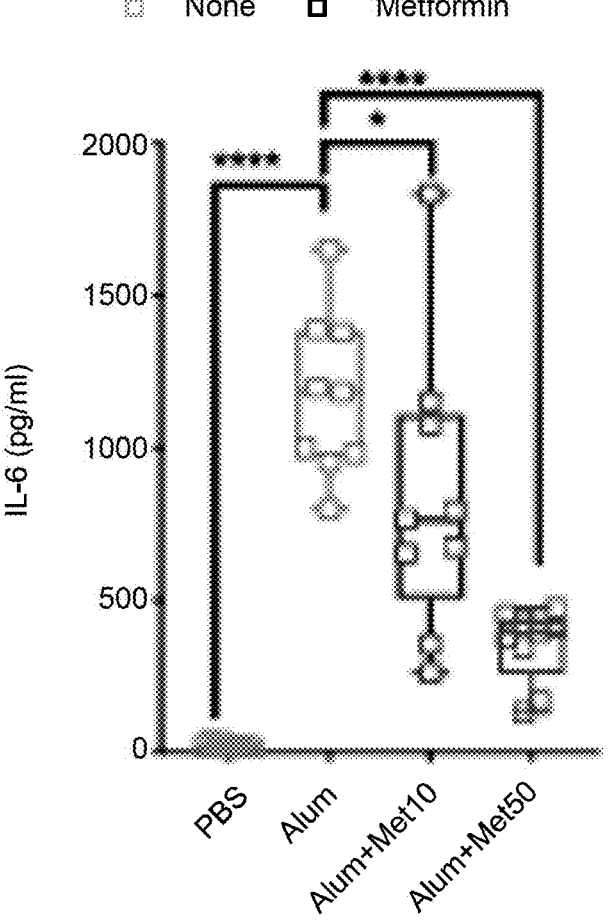

To determine whether short-term metformin treatment inhibits NLRP3-dependent inflammation in vivo Applicant used the alum induced peritonitis model (Guarda et al., 2011). Mice were given different doses of metformin 30 min prior to intraperitoneal (i.p.) alum challenge. Metformin treatment led to dose-dependent decline in IL-1β and IL-6 production (FIG. 2E and FIG. 2F), but as seen in vitro had no effect on TNF production (FIG. 9J).

Metformin Inhibits mtDNA Synthesis and Ox-mtDNA Generation

Figures 3A, 3B, 3C, 3D, 3E:
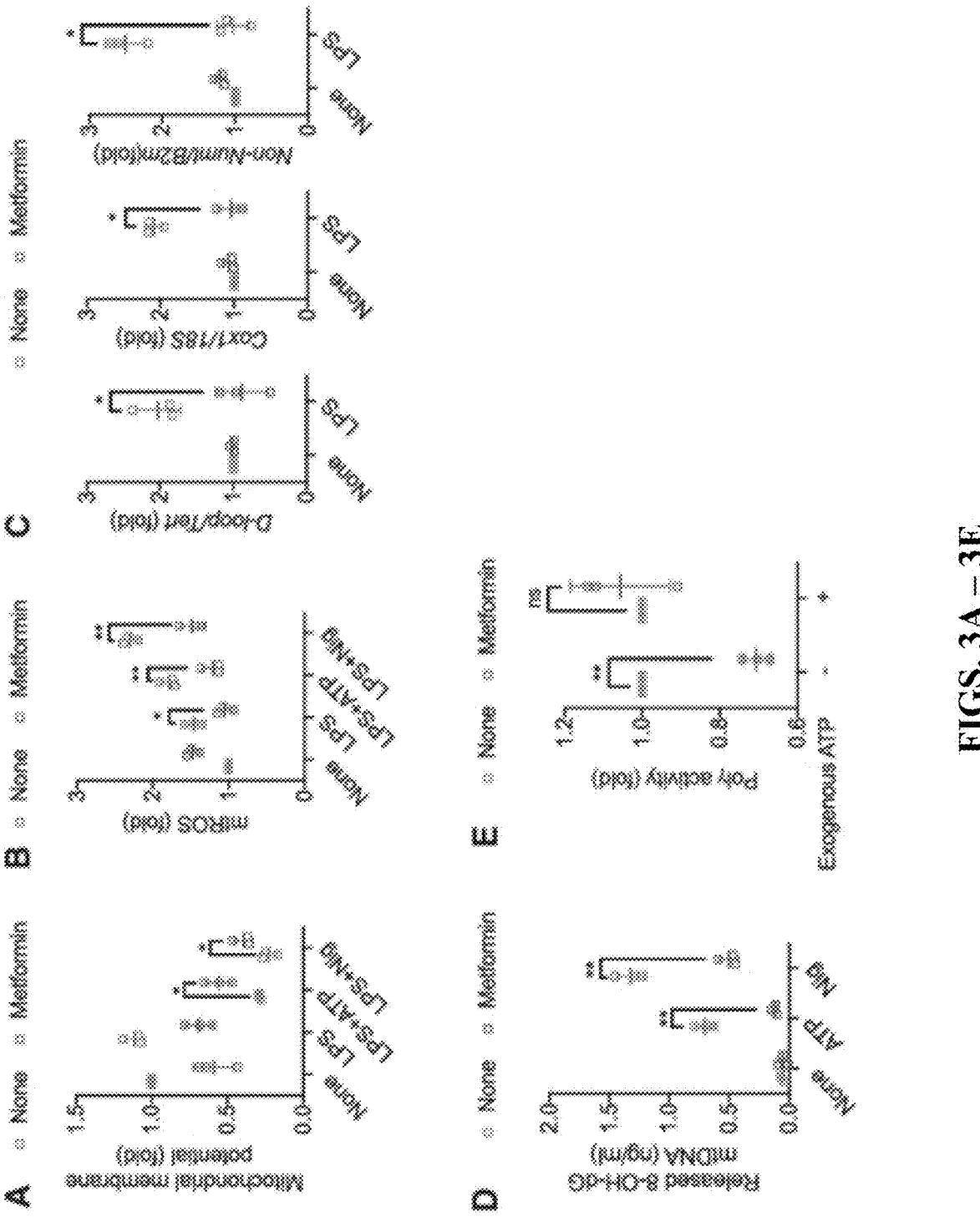
FIGS. 3A-3E: Metformin inhibits mtDNAsynthesis and cytosolic Ox-mtDNA release (FIG. 3A) Mitochondrial membrane potential of untreated and LPS (100 ng/mL, 4 h)-primed BMDM challenged with ATP (4 mM, 1 h) or nigericin (10 mM, 1 h), –/+ metformin (0.5 mM, 16 h) pretreatment, was measured by TMRM staining.
Figure 10J:
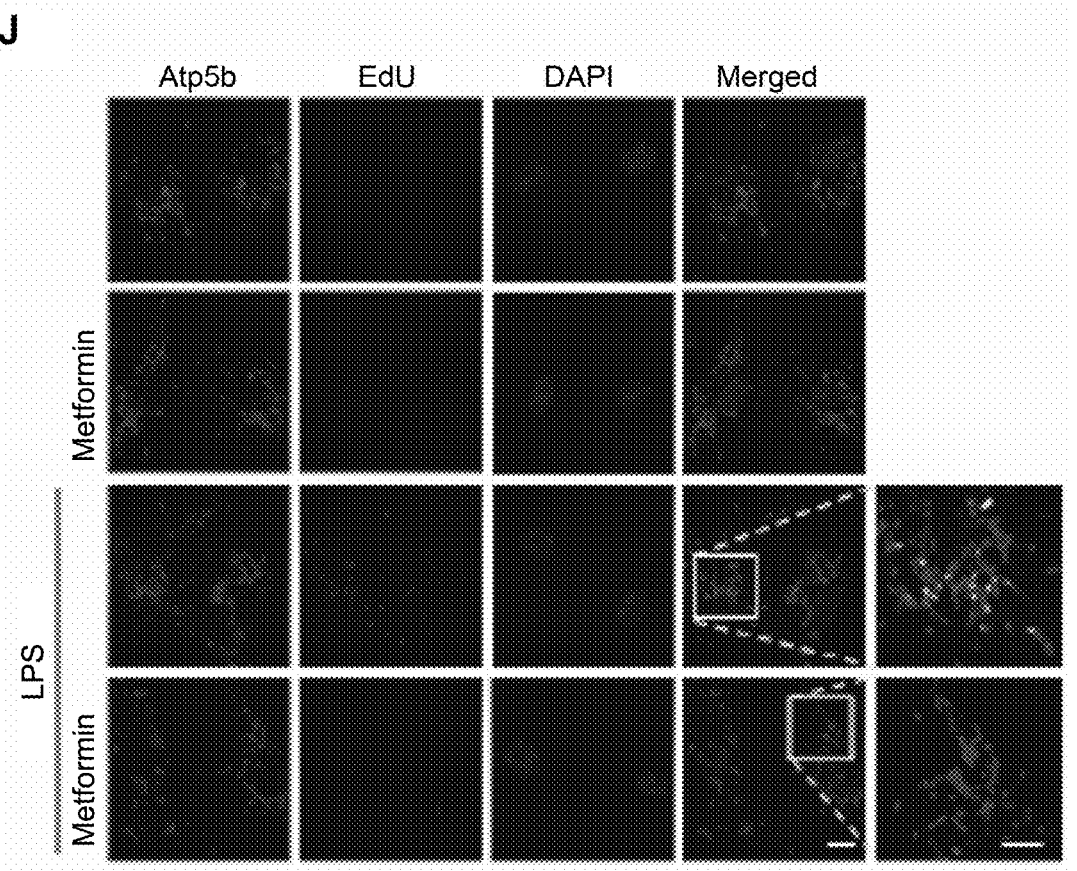

Metformin stimulates mitophagy by activating AMPK (Boyle et al., 2018), and mitophagy limits NLRP3 inflammasome activation (Sanchez-Lopez et al., 2019; Zhong et al., 2016). As expected, inhibition of mitophagy by p62 or ATG7 ablation enhanced Casp1 activation and IL-1β secretion (FIG. 10A-FIG. 10D). However, metformin still inhibited Casp1 activation and IL-1β secretion in p62- and ATG7-deficient macrophages (FIG. 10A-FIG. 10D), indicating that metformin's effect is mitophagy independent. Most NLRP3 inflammasome activators induce mitochondrial depolarization, measured by a drop in membrane potential, and stimulate mtROS production (Tschopp and Schroder, 2010; Zhong et al., 2016; Zhou et al., 2011). Accordingly, treatment of LPS-primed BMDM with ATP or nigericin decreased mitochondrial membrane potential and increased mtROS, and metformin treatment blunted both responses (FIG. 3A and FIG. 3B). Of note, metformin treatment decreased mitochondrial membrane potential on its own in non-stimulated macrophages, possibly due to defective ETCCI-mediated electron transfer from NADH to coenzyme Q. To determine whether inhibition of mtROS production by metformin contributes to inhibition of NLRP3 inflammasome activation Applicant used two compounds that stimulate ROS production, 2,3-dimethoxy-1,4-naphtoquinone (DMNQ) and mitoParaquat. Although both compounds increased mtROS in metformin treated and ATP-stimulated macrophages, neither one restored Casp1 activation and IL-1βsecretion (FIG. 10E-FIG. 10G). In addition to mtROS, metformin strongly inhibited LPS-stimulated mtDNA synthesis (FIG. 3C), and blocked generation of cytoplasmic Ox-mtDNA in LPS-primed macrophages challenged with either ATP or nigericin (FIG. 3D). Inhibition of cytoplasmic Ox-mtDNA or mtDNA synthesis were independent of mtROS, as neither parameter was restored by DMNQ or mitoParaquat treated macrophages (FIG. 10H and FIG. 10I). Inhibition of LPS-induced mtDNA synthesis by metformin was confirmed by ethynyl deoxyuridine (EdU)-labelling (FIG. 10J and FIG. 10K). Metformin had no effect on expression of CMPK2 (FIG. 10L-FIG. 10N), an LPS-inducible nucleotide kinase that converts dCMP to dCDP and is needed for stimulation of mtDNA synthesis (Zhong et al., 2018). Looking for another cause of blunted LPS-stimulated mtDNA synthesis, Applicant examined effects of metformin on POLg expression and activity. While having no effect on POLγ expression (FIG. 10O and FIG. 10P), metformin treatment decreased POLγ activity measured in lysates of LPS-stimulated macrophages with an assay mix containing all 4 dNTP precursors but lacking exogenous ATP (FIG. 3E). Addition of ATP at 10 mM fully restored POLT activity, suggesting that the apparent decline in enzyme activity was due to the low ATP content of metformin treated LPS-stimulated cells (FIG. 3E and FIG. 10Q). ATP is needed for initiation complex formation and POLγ movement along its DNA template (Burgers and Kornberg, 1982; Graziewicz et al., 2006).

Figures 4A, 4B, 4C, 4D:
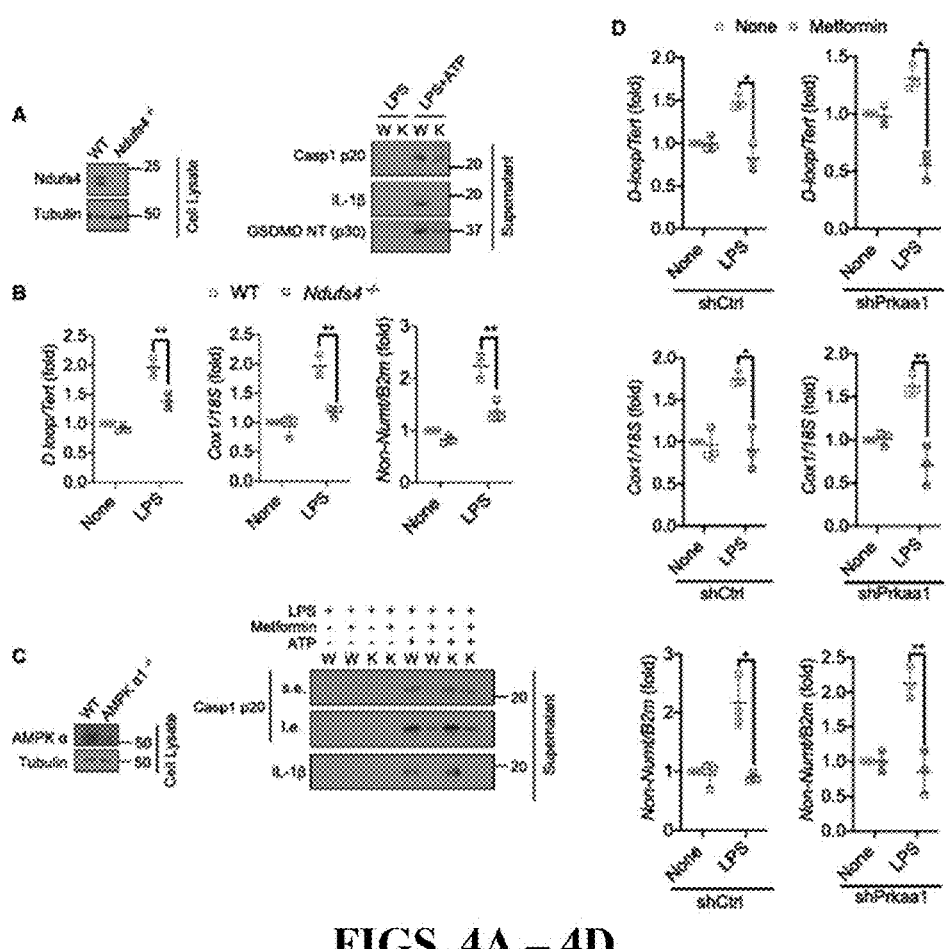
FIGS. 4A-4D: Metformin inhibits NLRP3 inflammasome activation via ETCCI, independently of AMPK (FIG. 4A) IB analysis of Ndufs4 (left), Casp1 p20, mature IL-1b, and cleaved GSDMD (right) in culture supernatants and cell lysates of LPS (100 ng/mL, 4 h)-primed wild type (W) or Ndufs4/(K) BMDM stimulated/+ ATP (4 mM, 1 h).
Figure 11B:
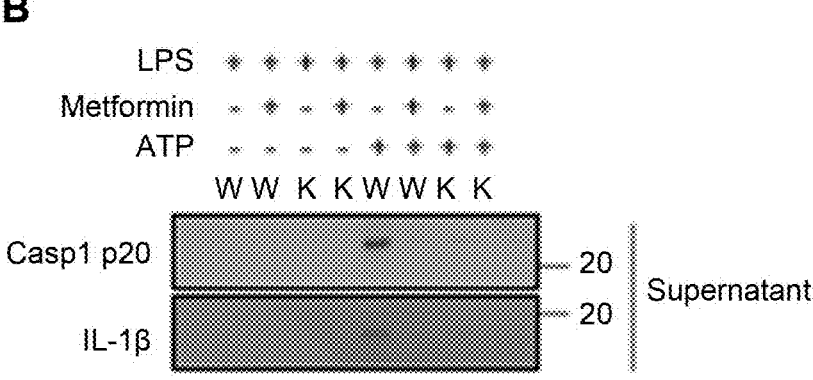
Figure 11C:
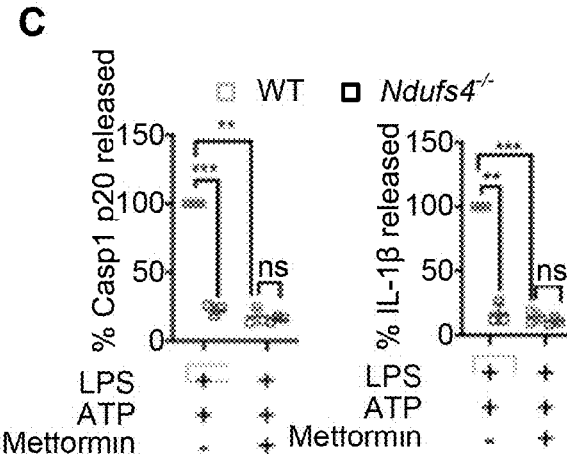
Figure 11D:
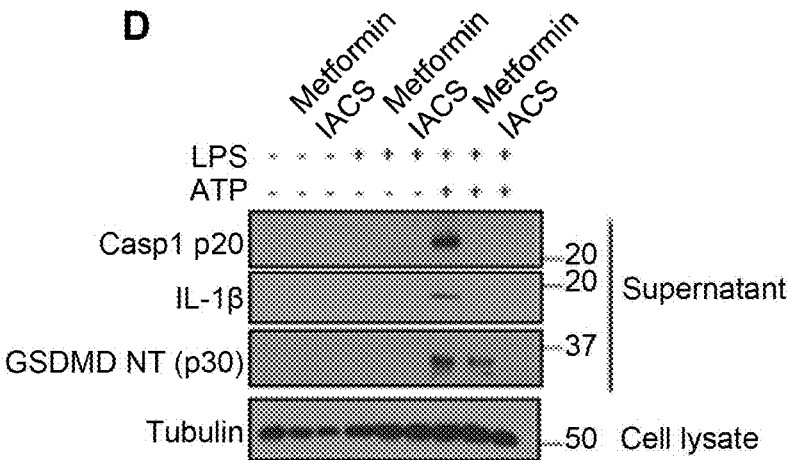

Metformin inhibits ATP production by targeting ETCCI (Wheaton et al., 2014). To validate the role of ETCCI in NLRP3 inflammasome activation Applicant used Ndufs4-deficient BMDM, missing a subunit needed for ETCCI assembly and function (McElroy et al., 2020; Yang et al., 2020b). Ndufs4-deficient BMDM exhibited defective NLRP3 inflammasome activation and GSDMD cleavage (FIG. 4A and FIG. 11A), and metformin did not further reduce IL-1β and Casp1 p20 release in these cells (FIG. 11B and FIG. 11C). The Ndufs4 deficiency also interfered with LPS-induced mtDNA synthesis (FIG. 4B). A recently developed ETCCI inhibitor, IACS-010759 (Molina et al., 2018) which is chemically unrelated and more potent than metformin, also inhibited IL-1β production and Casp1 and GSMDM cleavage in LPS-primed macrophages stimulated with NLRP3 inflammasome activators (FIG. 11D-FIG. 11F). As found with metformin, the response to nigericin was not as strongly inhibited as the response to the other activators. IACS-010759 treatment also led to modest inhibition of IL-6 secretion (FIG. 11G) but had no effect on TNF (FIG. 11H). IACS-010759 also inhibited mtDNA synthesis, but unlike metformin and similar to the potent ETCCI inhibitor rotenone (Wheaton et al., 2014), it enhanced ROS production (FIG. 11I and FIG. 11J). These results further confirm that inhibition of mtROS production is not required for metformin inhibition of NLRP3 inflammasome activation. Next, Applicant examined the role of AMPK activation in inhibition of NLRP3 inflammasome activation. AMPKα1 ablation had no effect on inhibition of Casp1 activation or IL-1β processing and secretion by metformin in LPS-primed BMDM stimulated with ATP (FIG. 4C and FIG. 11K). Importantly, AMPKα1 silencing had no effect on LPS-stimulated mtDNA synthesis and its inhibition by metformin (FIG. 4D). Congruently, AMPKα1 deficiency had no effect on POLγ expression or activity in lysates of metformin treated LPS stimulated BMDM (FIG. 11L-FIG. 11N).

Metformin Inhibits LPS-Induced ARDS

Figures 5C, 5D, 5E, 5F, 5G, 5H:
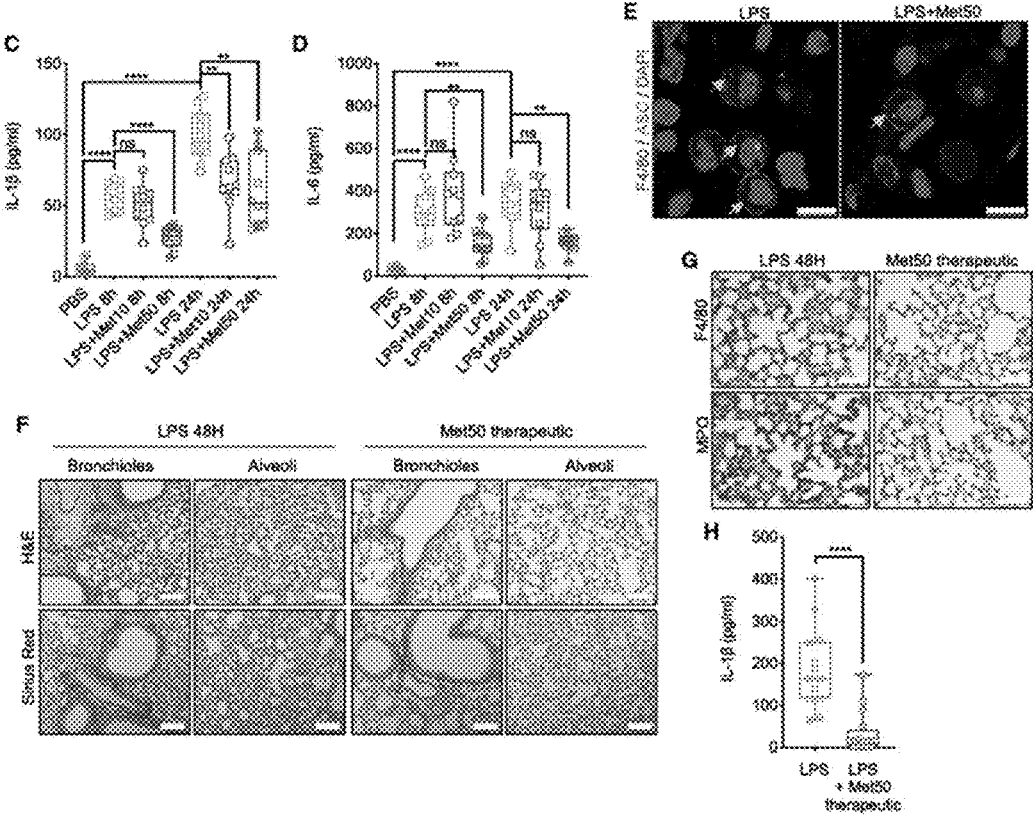

ARDS is a common cause of respiratory failure in critically ill patients with a mortality rate of 30-40% (Matthay et al., 2019). Applicant examined whether short-term metformin treatment can prevent or ameliorate ARDS in mice i.p. injected with a single bolus of 5 mg/kg LPS followed by collection of bronchioalveolar lavage fluid (BALF) and lung tissue after 8 and 24 hrs (FIG. 12A). As described (Menezes et al., 2005), LPS administration damaged the pulmonary vascular endothelium and led to interstitial edema accompanied by innate immune cell recruitment into the septa and alveolar space with evident alveolar walls thickening and secondary collagen deposition (FIG. 12B). In the first set of experiments, mice were given vehicle or two different doses of metformin for three consecutive days with the last dose administered 30 min prior to LPS challenge (FIG. 12A). Whereas at 10 mg/kg metformin had a modest protective effect, at 50 mg/kg it led to strong protection. Histological assessment of lung sections showed that at 50 mg/kg metformin prevented septa thickening and inhibited infiltration of inflammatory cells into the bronchioles, vascular bed, and lung parenchyma, and abrogated collagen buildup (FIG. 5A and FIG. 5C). At that dose metformin strongly inhibited macrophage and neutrophil infiltration (FIG. 5B, FIG. 12D and FIG. 12E), and this was accompanied by decreased IL-1β and IL-6 in BALF, with no effect on TNF (FIG. 5C, FIG. 5D and FIG. 12F). Consistently, metformin limited ASC speck formation (FIG. 5E and FIG. 12G), and c/EBPβ and NFAT activation (F FIG. 12H-FIG. 12J), and reduced mortality of mice challenged with a higher LPS dose (FIG. 12K).

Next, Applicant tested whether metformin administration after LPS challenge ameliorates LPS-induced ARDS. Metformin was given by i.p. injection at 50 mg/kg at 30 min after LPS administration with a second dose given after 24 hrs. Mice were evaluated 24 hrs after the last metformin dose (FIG. 12L). Therapeutic administration of metformin was as effective as the prophylactic treatment, reducing septa thickening, infiltration of inflammatory/monocytic cells into the bronchioles, vascular bed and lung parenchyma, and abrogating collagen buildup (FIG. 5F). Therapeutic metformin also inhibited macrophage and neutrophil infiltration (FIG. 5G), and decreased IL-1β in BALF (FIG. 5H). Applicant also examined the preventive efficacy of oral metformin dissolved in drinking water, starting 48 hrs prior to LPS challenge (FIG. 12M). Oral metformin was as protective as injected metformin (FIG. 12N-FIG. 12P). Applicant compared the plasma concentrations of metformin given via the two routes. Although oral metformin resulted in higher plasma concentrations than i.p. metformin at the time of LPS administration (942.57±658.76 ng/ml vs. 439.57±389.02 ng/ml), at 24 hrs after LPS challenge the circulating concentrations of metformin were equally low, regardless of its administration route (FIG. 20Q). Although the mice were left on oral metformin until the end of the experiment, soon after LPS injection their water intake decreased dramatically (FIG. 12R), thus explaining why at 24 hrs after LPS challenge metformin plasma concentrations were equally low in both treatment groups.

Myeloid Specific Cmpk2 Ablation Protects from LPS-Induced ARDS but Only Affects IL-1β.

Figures 6A, 6B, 6C, 6D:
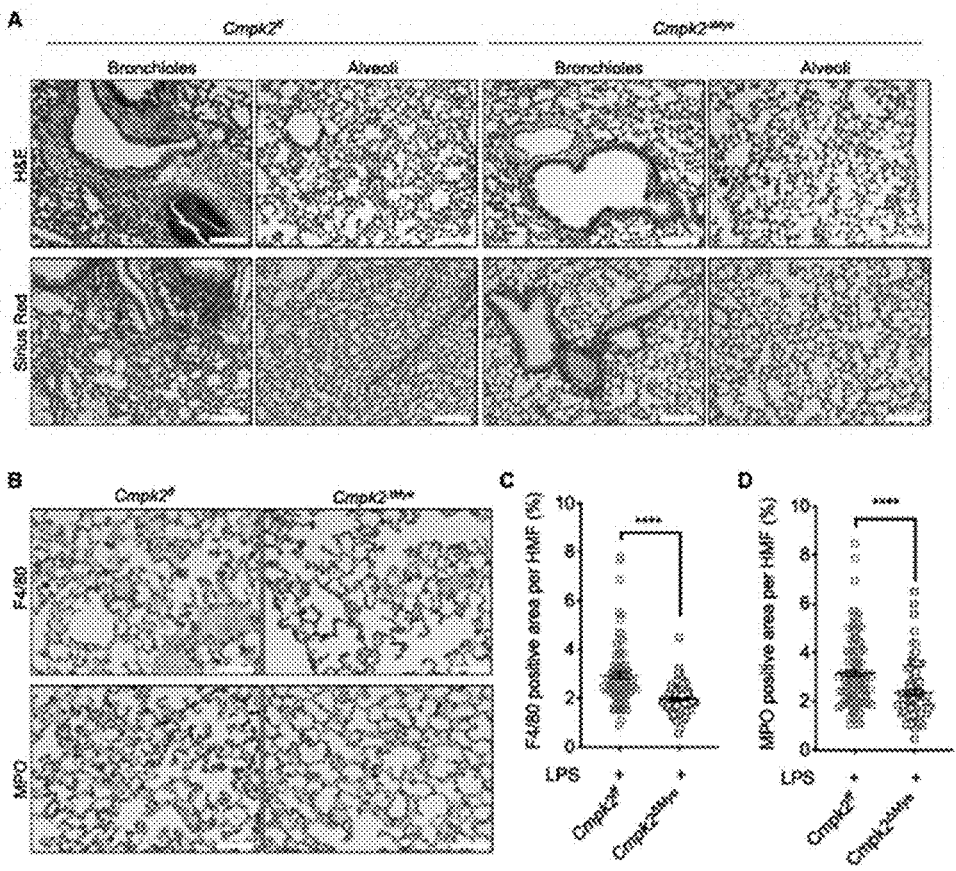
FIGS. 6A-6H: Myeloid-specific Cmpk2 ablation recapitulates metformin protective effects in LPS-induced ARDS (FIG. 6A) H&E and Sirius red staining of lung tissue from Cmpk2ff and Cmpk2DMye mice challenged with 5 mg/kg LPS for 24 h. Scalebar, 100 mm. n=7-9 mice per group. 10-12 images per mouse were evaluated.
Figures 6E, 6F, 6G, 6H:
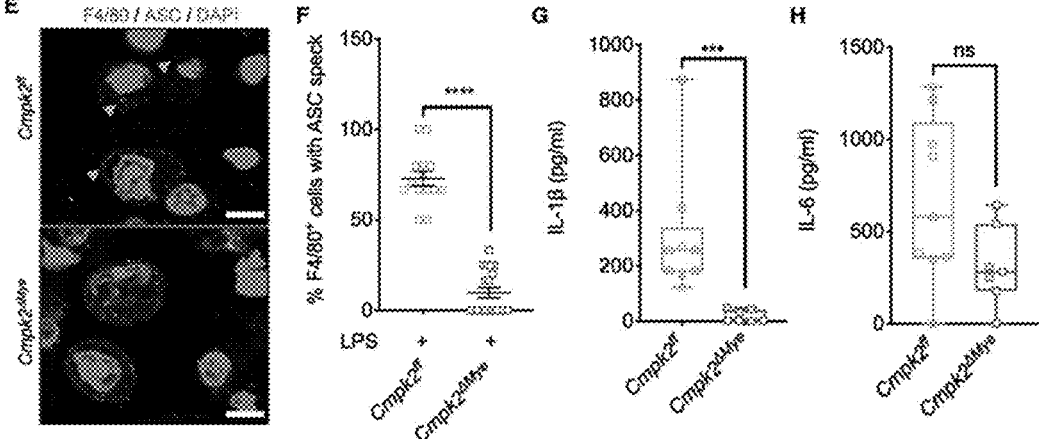

To confirm that inhibition of LPS-induced mtDNA synthesis can reduce pulmonary inflammation and IL-1β production in vivo, Applicant generated mice with myeloid-specific ablation of CMPK2 (Cmpk2$^{\Delta\Delta Mye}$ mice). As expected (Zhong et al., 2018), CMPK2-deficient BMDM (Cmpk2$^{\Delta/\Delta}$), exhibited defective LPS-stimulated mtDNA synthesis, Casp1 activation and IL-1b secretion (FIG. 13A-FIG. 13E). Consistently, mice lacking CMPK2 in the myeloid compartment were protected from LPS-induced ARDS similar to metformin treated animals (FIG. 6A), exhibiting reduced macrophage and neutrophil infiltration (FIG. 6B-FIG. 6D). Cmpk2$^{\Delta\Delta Mye}$ mice also had significantly fewer macrophages with ASC specks, indicating reduced NLRP3 inflammasome activation (FIG. 6E and FIG. 6F). CMPK2 ablation also led to near complete blockade of IL-1β release but had a small and insignificant effect on c/EBPβ activation and IL-6 secretion (IG. 6G, IG. 6H and FIG. 13F and FIG. 13G). Metformin treatment of Cmpk2$^{\Delta\Delta Mye}$ mice did not result in noticeable improvement of lung pathology or reduced IL-1β secretion, but it did inhibit c/EBPβ activation and IL-6 secretion to BALF (FIG. 13G-FIG. 13I). These results confirm that metformin affects IL-1β and IL-6 secretion through entirely different mechanisms, with only IL-1β being dependent on LPS-induced mtDNA synthesis, which is blocked by CMPK2 ablation. Moreover, these results demonstrate that myeloid-specific inhibition of TLR-induced mtDNA synthesis is sufficient for conferring protection from LPS-induced ARDS.

Metformin Attenuates SARS-CoV-2 Induced Pulmonary Inflammation

Figures 7A, 7B, 7C, 7D, 7E, 7F, 7G:
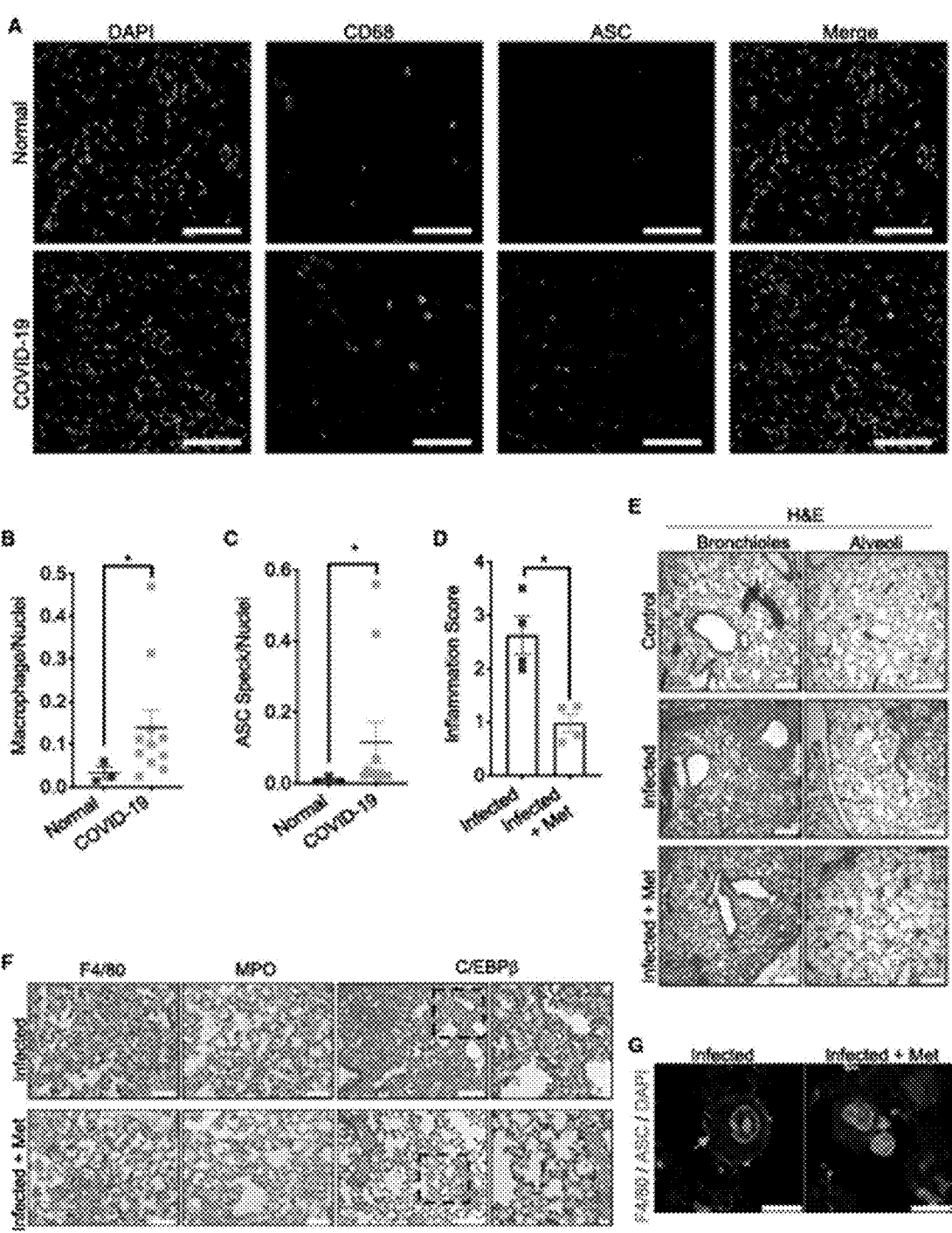
FIGS. 7A-7G: Metformin attenuates ARDS caused by SARS-CoV-2 infection (FIG. 7A) Representative images from healthy (n=3) and COVID-19 post-mortem (n=11) tissue stained for CD68 (yellow) and ASC (red) taken at 20×.
Figures 14A, 14B, 14C, 14D, 14E:
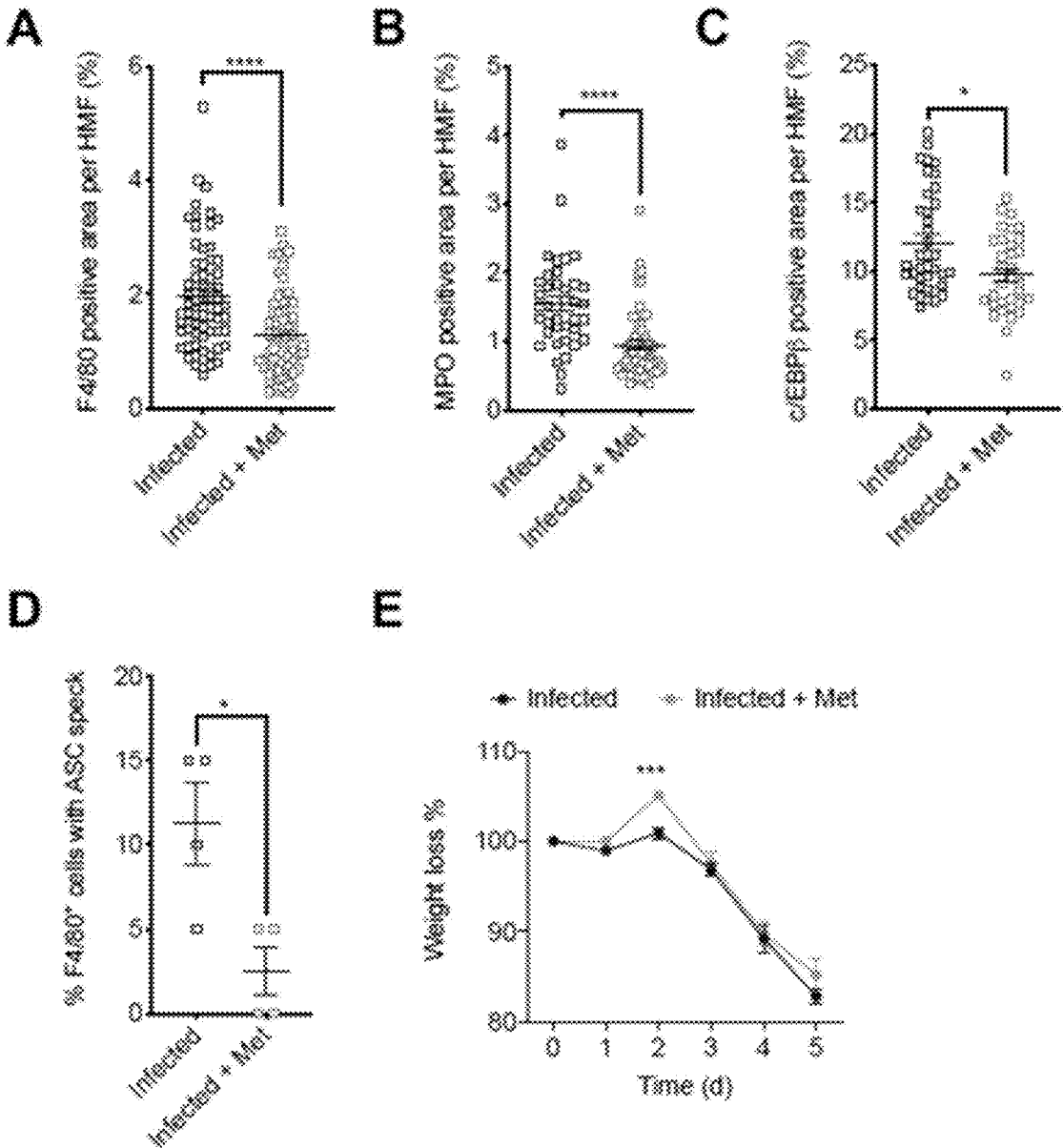

Consistent with a recent report of NLRP3 inflammasome activation in COVID-19 PBMCs (Rodrigues et al., 2021), Applicant observed enhanced macrophage recruitment and ASC speck formation in COVID-19 post-mortem lungs (FIG. 7A-FIG. 7C). To determine whether metformin treatment reduces SARS-CoV-2 elicited pulmonary inflammation, Applicant used SARS-CoV-2 infectable hACE2 Tg mice (Bao et al., 2020; Winkler et al., 2020). The mice were i.p. injected with 50 mg/kg metformin or vehicle, starting 2 days before intranasal inoculation with $10^4$ PFU of SARS-CoV-2 USA-WA1/2020 strain, and lung tissue was collected for analysis 6 days post-infection. Similar to LPS-induced ARDS, metformin reduced immune cell infiltration and alveolar wall thickening and c/EBPβ activation caused by SARS-CoV-2 infection (FIG. 7D-FIG. 7F and FIG. 14A-FIG. 14C). Although at day 6 post-infection only few macrophages with ASC specks were observed in SARS-CoV-2 infected lungs, almost none were found in metformin treated lungs (FIG. 7G and FIG. 14D). Metformin treatment also slowed down the infection-associated loss of body weight at day 2 post-inoculation (FIG. 14E), however, the mechanism underlying this effect is currently unknown.

Discussion

ARDS is associated with high mortality rates and is a serious and often fatal complication of COVID-19, although its manifestation in the latter differs from "typical" ARDS (Fan et al., 2020; Han and Mallampalli, 2015; Li and Ma, 2020; Wu et al., 2020). Mortality and ARDS risk in SARS-CoV-2 infected individuals are increased by old age and comorbidities such as T2D, obesity and hypertension (Gao et al., 2020; Guan et al., 2020; Richardson et al., 2020; Singh and Khan, 2020; Verma et al., 2020), but are substantially reduced by long-term metformin usage (Bramante et al., 2020; Crouse et al., 2020; Li et al., 2020; Luo et al., 2020). This protective effect is independent of glycemic control and is related to metformin's anti-inflammatory properties (Barzilai et al., 2016; Pollak, 2017; Valencia et al., 2017). Nonetheless, whether short-term metformin treatment of non-diabetic subjects can prevent acute inflammatory responses, including ARDS, was heretofore unknown. Applicant now shows that abrupt metformin-based intervention prevents and ameliorates LPS-induced ARDS in mice, accompanied with abrogated in situ NLRP3 inflammasome activation and IL-1β and IL-6 secretion. The mechanisms by which metformin inhibits IL-6 and IL-1β secretion are distinct. IL-6 production is mainly reduced at the transcriptional level, whereas inhibition of IL-1β secretion is primarily due to post-translational inhibition of NLRP3 inflammasome activation and defective pro-IL-1b processing. Consistent with previous studies (Soberanes et al., 2019), inhibition of IL-6 expression correlates with blunted NFAT and c/EBPβ/NF-IL6 nuclear translocation and recruitment to the Il6 promoter region, demonstrated by the ChIP experiments. This is most likely due to defective JNK and p38 activation, as inhibitors of these kinases blocked IL-6 mRNA induction and protein secretion. Nonetheless, inhibition of both IL-6 and IL-1β is mediated by metformin's well established inhibitory effect on ETCCI (Wheaton et al., 2014). Of note, metformin did not inhibit NF-κB activation and did not block induction of numerous cytokine mRNAs, including IFNβ and IFNγ.

While confirming metformin's ability to diminish ETCCI-dependent and c/EBPβ and NFAT-mediated IL-6 production in alveolar macrophages (Soberanes et al., 2019), Applicant shows that metformin is an effective inhibitor of NLRP3 inflammasome activation in vitro and in vivo and have identified its mode of action. The principle molecular target for metformin is ETCCI, whose inhibition reduces ATP production (Bridges et al., 2014; Wheaton et al., 2014). Consistent with previous publications showing that LPS induces a glycolytic switch and increases mitochondrial membrane potential (Ip et al., 2017; Mills et al., 2016), metformin elicited a larger drop in ATP concentration in LPS-primed than in non-stimulated macrophages. Genetic ablation of ETCCI subunit Ndufs4 also inhibited NLRP3 inflammasome activation and LPS-induced mtDNA synthesis, and in Ndusf4$^{-/-}$ macrophages metformin did not lead to further inhibition of Casp1 activation and IL-1β secretion. Newly replicated single stranded mtDNA is highly susceptible to oxidative damage leading to Ox-mtDNA generation (Zhong et al., 2018). Fragments of Ox-mtDNA entering the cytoplasm bind NLRP3 and trigger inflammasome assembly and activation (Shimada et al., 2012; Zhong et al., 2018). Although metformin attenuates mtROS accumulation in macrophages treated with the NLRP3 activators ATP and nigericin, this effect is not important for inhibition of NLRP3 inflammasome activation which is not reversed by treatment of metformin-incubated macrophages with the mtROS generators mitoParaquat and DMNQ. Moreover, another ETCCI inhibitor IACS-010759 also blocked NLRP3 inflammasome activation and IL-1β secretion, but like the ETCCI inhibitor rotenone (Wheaton et al., 2014), it enhanced mtROS production. Applicants therefore concludes that the main mechanism by which metformin prevents NLRP3 inflammasome activation is inhibition of TLR-induced mtDNA synthesis, which blocks NLRP3 inflammasome activation in vitro and in vivo and protects mice from LPS-induced ARDS. Importantly, treatment of Cmpk2$^{ΔΔMye}$ mice with metformin did not result in any further decrease in IL-1β secretion although it inhibited IL-6, whose production was unaffected by CMPK2 ablation. Disruption of cytoplasmic accumulation of fragmented mtDNA and inhibition of GSDMD cleavage may prevent the circulatory release of mtDNA, thus attenuating distant organ damage (Grazioli and Pugin, 2018), and making further contribution to the protective effects of metformin and myeloid-specific CMPK2 ablation. In contrast to previous studies showing metformin-induced NF-κB inhibition in vascular endothelial cells and cardiomyocytes (Hattori et al., 2006; Vaez et al., 2016), no inhibition of NF-κB or NF-κB-dependent cytokine mRNA induction took place in mouse or human macrophages. Although Applicant doesn't rule out that metformin may manifest its ARDS protective effects in endothelial cells, it should be pointed out that NF-κB inhibition in such cells enhances TNF-induced apoptosis (Liu et al., 1996), resulting in vascular leakage. Applicant also found no role for metformin-induced AMPK activation in inhibition of IL-1β and IL-6 production. AMPK-induced autophagy was speculated to be responsible for inhibition of NLRP3 inflammasome by metformin in non-myeloid cell types (Lee et al., 2013; Li et al., 2016; Yang et al., 2019). However, AMPKα1 ablation or autophagy blockade by p62 or ATG7 ablation did not diminish metformin's ability to inhibit NLRP3 inflammasome activation and IL-1β secretion.

Inhibition of IL-6 and IL-1β production by lung macrophages is likely to account for the ARDS blocking activity of metformin. The NLRP3 inflammasome and its products IL-1β and IL-18 play critical roles in ARDS pathogenesis (Dolinay et al., 2012; Ganter et al., 2008; Kolb et al., 2001), and recent studies implicate them along with IL-6 in acute airway inflammation triggered by SARS-CoV-2 and its relatives SARS-CoV-1 and MERS-CoV (Freeman and Swartz, 2020). Congruently, NLRP3 inflammasome activation was detected in COVID-19 PBMC (Rodrigues et al., 2021) and post-mortem lungs and the results demonstrate a protective effect of metformin in SARS-CoV-2 infected hACE2 Tg mice. A study of IL-1 receptor antagonist (IL-IRA, anakinra) in a small COVID-19 cohort revealed rapid decline in inflammation and fever, followed by clinical improvement (Cauchois et al., 2020). Similar results, including reduced mortality or need for mechanical ventilation, were found in another COVID-19 anakinra study (Huet et al., 2020), and a recent clinical trial has established the COVID-19 ameliorating effect of IL-6 receptor blockade (Gupta et al., 2021). Although metformin is not a specific NLRP3 inflammasome inhibitor, no specific NLRP3 antagonist had advanced to the clinic. Recently, however, FDA-approved BTK inhibitors were found to inhibit NLRP3 inflammasome activation (Ito et al., 2015) and reduce inflammation in COVID-19 (Roschewski et al., 2020). Another FDA-approved drug that may reduce IL-1β secretion is disulfiram, which is used to fight alcohol addiction. Disulfiram does not inhibit GSDMD cleavage but it blocks formation of the pore formed by its N-terminal fragment (Hu et al., 2020).

Inhibition of LPS-induced ARDS by metformin is extensive, reducing macrophage infiltration and collagen deposition. The dose of metformin required for these effects, 50 mg/kg per bolus, is equivalent to its maximal human daily dosage, 3 g/day orally in a 60 kg person (Wilcock and Bailey, 1994). Although oral metformin is just as effective as metformin injection, it should be noted that macrophages barely express the metformin and organic cation transporter OCT1, which mediates metformin uptake into hepatocyte, where it inhibits gluconeogenesis (Nies et al., 2009). Thus, the efficacy of acute metformin-based intervention in different ARDS etiologies may be improved by directed delivery into lung macrophages using nanoparticles or liposomes.

Given the important role of IL-1β and IL-6 in tumor development and progression (Greten and Grivennikov, 2019; Grivennikov et al., 2010), it is likely that inhibition of cytokine production by tumor associated macrophages contributes to metformin's anti-cancer activity (Pollak, 2012). Supporting this hypothesis, a large clinical study of the IL-1β blocking antibody canakinumab in cardiovascular disease revealed a significant reduction in lung cancer incidence and mortality (Ridker et al., 2017). Given the widespread involvement of IL-1 in multiple inflammatory pathologies (Dinarello, 2011), Applicant proposes that metformin should be evaluated for therapeutic efficacy in such diseases. Given its low cost and high safety profile, metformin represents a viable alternative to expensive biological IL-1 blockers, such as anakinra and canakinumab.

Equivalents

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scoped of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

Akira, S., Isshiki, H., Sugita, T., Tanabe, O., Kinoshita, S., Nishio, Y., Nakajima, T., Hirano, T., and Kishimoto, T. (1990). A nuclear factor for IL-6 expression (NF-IL6) is a member of a C/EBP family. EMBO J 9, 1897-1906.

Bankhead, P., Loughrey, M. B., Fernandez, J. A., Dombrowski, Y., McArt, D. G., Dunne, P. D., McQuaid, S., Gray, R. T., Murray, L. J., Coleman, H. G., et al. (2017). QuPath: Open source software for digital pathology image analysis. Sci Rep 7, 16878.

Bao, L., Deng, W., Huang, B., Gao, H., Liu, J., Ren, L., Wei, Q., Yu, P., Xu, Y., Qi, F., et al. (2020). The pathogenicity of SARS-CoV-2 in hACE2 transgenic mice. Nature 583, 830-833.

Barzilai, N., Crandall, J. P., Kritchevsky, S. B., and Espeland, M. A. (2016). Metformin as a Tool to Target Aging. Cell Metab 23, 1060-1065.

Boyle, K. A., Van Wickle, J., Hill, R. B., Marchese, A., Kalyanaraman, B., and Dwinell, M. B. (2018). Mitochondria-targeted drugs stimulate mitophagy and abrogate colon cancer cell proliferation. J Biol Chem 293, 14891-14904.

Bramante, C., Ingraham, N., Murray, T., Marmor, S., Hoversten, S., Gronski, J., McNeil, C., Feng, R., Guzman, G., Abdelwahab, N., et al. (2020). Observational Study of Metformin and Risk of Mortality in Patients Hospitalized with Covid-19. medRxiv.

Bridges, H. R., Jones, A. J., Pollak, M. N., and Hirst, J. (2014). Effects of metformin and other biguanides on oxidative phosphorylation in mitochondria. Biochem J 462, 475-487.

Burgers, P. M., and Kornberg, A. (1982). ATP activation of DNA polymerase III holoenzyme of *Escherichia coli*. I. ATP-dependent formation of an initiation complex with a primed template. J Biol Chem 257, 11468-11473.

Campbell, J. M., Stephenson, M. D., de Courten, B., Chapman, I., Bellman, S. M., and Aromataris, E. (2018). Metformin Use Associated with Reduced Risk of Dementia in Patients with Diabetes: A Systematic Review and Meta-Analysis. J Alzheimers Dis 65, 1225-1236.

Cauchois, R., Koubi, M., Delarbre, D., Manet, C., Carvelli, J., Blasco, V. B., Jean, R., Fouche, L., Bornet, C., Pauly, V., et al. (2020). Early IL-1 receptor blockade in severe inflammatory respiratory failure complicating COVID-19. Proc Natl Acad Sci USA 117, 18951-18953.

Chen, I. Y., Moriyama, M., Chang, M. F., and Ichinohe, T. (2019). Severe Acute Respiratory Syndrome Coronavirus Viroporin 3a Activates the NLRP3 Inflammasome. Front Microbiol 10, 50.

Cheng, X., Liu, Y. M., Li, H., Zhang, X., Lei, F., Qin, J. J., Chen, Z., Deng, K. Q., Lin, L., Chen, M. M., et al. (2020). Metformin Is Associated with Higher Incidence of Acidosis, but Not Mortality, in Individuals with COVID-19 and Pre-existing Type 2 Diabetes. Cell Metab.

Cohen, P. (2014). The TLR and IL-1 signalling network at a glance. J Cell Sci 127, 2383-2390.

Crouse, A., Grimes, T., Li, P., Might, M., Ovalle, F., and Shalev, A. (2020). Metformin Use Is Associated with Reduced Mortality in a Diverse Population with Covid-19 and Diabetes. medRxiv.

Day, C. W., Baric, R., Cai, S. X., Frieman, M., Kumaki, Y., Morrey, J. D., Smee, D. F., and Barnard, D. L.

US 12,642,780 B2

57

(2009). A new mouse-adapted strain of SARS-CoV as a lethal model for evaluating antiviral agents in vitro and in vivo. Virology 395, 210-222.

Dick, I. E., Joshi-Mukherjee, R., Yang, W., and Yue, D. T. (2016). Arrhythmogenesis in Timothy Syndrome is associated with defects in Ca(2+)-dependent inactivation. Nat Commun 7, 10370.

Dinarello, C. A. (2011). Interleukin-1 in the pathogenesis and treatment of inflammatory diseases. Blood 117, 3720-3732.

Dolinay, T., Kim, Y. S., Howrylak, J., Hunninghake, G. M., An, C. H., Fredenburgh, L., Massaro, A. F., Rogers, A., Gazourian, L., Nakahira, K., et al. (2012). Inflammasome-regulated cytokines are critical mediators of acute lung injury. Am J Respir Crit Care Med 185, 1225-1234.

Dosch, S. F., Mahajan, S. D., and Collins, A. R. (2009). SARS coronavirus spike protein-induced innate immune response occurs via activation of the NF-kappaB pathway in human monocyte macrophages in vitro. Virus Res 142, 19-27.

Duca, F. A., Cote, C. D., Rasmussen, B. A., Zadeh-Tahmasebi, M., Rutter, G. A., Filippi, B. M., and Lam, T. K. (2015). Metformin activates a duodenal Ampk-dependent pathway to lower hepatic glucose production in rats. Nat Med 21, 506-511.

Fan, E., Beitler, J. R., Brochard, L., Calfee, C. S., Ferguson, N. D., Slutsky, A. S., and Brodie, D. (2020). COVID-19-associated acute respiratory distress syndrome: is a different approach to management warranted?Lancet Respir Med 8, 816-821.

Freeman, T. L., and Swartz, T. H. (2020). Targeting the NLRP3 Inflammasome in Severe COVID-19. Front Immunol 11, 1518.

Ganter, M. T., Roux, J., Miyazawa, B., Howard, M., Frank, J. A., Su, G., Sheppard, D., Violette, S. M., Weinreb, P. H., Horan, G. S., et al. (2008). Interleukin-Ibeta causes acute lung injury via alphavbeta5 and alphavbeta6 integrin-dependent mechanisms. Circ Res 102, 804-812.

Gao, F., Zheng, K. I., Wang, X. B., Yan, H. D., Sun, Q. F., Pan, K. H., Wang, T. Y., Chen, Y. P., George, J., and Zheng, M. H. (2020). Metabolic associated fatty liver disease increases coronavirus disease 2019 disease severity in nondiabetic patients. J Gastroenterol Hepatol.

Graziewicz, M. A., Longley, M. J., and Copeland, W. C. (2006). DNA polymerase gamma in mitochondrial DNA replication and repair. Chem Rev 106, 383-405.

Grazioli, S., and Pugin, J. (2018). Mitochondrial Damage-Associated Molecular Patterns: From Inflammatory Signaling to Human Diseases. Front Immunol 9, 832.

Greten, F. R., and Grivennikov, S. I. (2019). Inflammation and Cancer: Triggers, Mechanisms, and Consequences. Immunity 51, 27-41.

Grivennikov, S. I., Greten, F. R., and Karin, M. (2010). Immunity, inflammation, and cancer. Cell 140, 883-899.

Group, R. C., Horby, P., Lim, W. S., Emberson, J. R., Mafham, M., Bell, J. L., Linsell, L., Staplin, N., Brightling, C., Ustianowski, A., et al. (2021). Dexamethasone in Hospitalized Patients with Covid-19. N Engl J Med 384, 693-704.

Guan, W. J., Liang, W. H., Zhao, Y., Liang, H. R., Chen, Z. S., Li, Y. M., Liu, X. Q., Chen, R. C., Tang, C. L.,

58

Wang, T., et al. (2020). Comorbidity and its impact on 1590 patients with COVID-19 in China: a nationwide analysis. Eur Respir J 55.

Guarda, G., Braun, M., Staehli, F., Tardivel, A., Mattmann, C., Forster, I., Farlik, M., Decker, T., Du Pasquier, R. A., Romero, P., and Tschopp, J. (2011). Type I interferon inhibits interleukin-1 production and inflammasome activation. Immunity 34, 213-223.

Gupta, S., Wang, W., Hayek, S. S., Chan, L., Mathews, K. S., Melamed, M. L., Brenner, S. K., Leonberg-Yoo, A., Schenck, E. J., Radbel, J., et al. (2021). Association Between Early Treatment With Tocilizumab and Mortality Among Critically Ill Patients With COVID-19. JAMA Intern Med 18, 41-51.

Han, S., and Mallampalli, R. K. (2015). The acute respiratory distress syndrome: from mechanism to translation. J Immunol 194, 855-860.

Hattori, K., Inoue, M., Inoue, T., Arai, H., and Tamura, H. O. (2006). A novel sulfotransferase abundantly expressed in the dauer larvae of Caenorhabditis elegans. J Biochem 139, 355-362.

Hornung, V., Bauernfeind, F., Halle, A., Samstad, E. O., Kono, H., Rock, K. L., Fitzgerald, K. A., and Latz, E. (2008). Silica crystals and aluminum salts activate the NALP3 inflammasome through phagosomal destabilization. Nat Immunol 9, 847-856.

Hu, J. J., Liu, X., Xia, S., Zhang, Z., Zhang, Y., Zhao, J., Ruan, J., Luo, X., Lou, X., Bai, Y., et al. (2020). FDA-approved disulfiram inhibits pyroptosis by blocking gasdermin D pore formation. Nat Immunol 21, 736-745.

Huet, T., Beaussier, H., Voisin, O., Jouveshomme, S., Dauriat, G., Lazareth, I., Sacco, E., Naccache, J. M., Bezie, Y., Laplanche, S., et al. (2020). Anakinra for severe forms of COVID-19: a cohort study. Lancet Rheumatol 2, e393-e400.

Ip, W. K. E., Hoshi, N., Shouval, D. S., Snapper, S., and Medzhitov, R. (2017). Anti-inflammatory effect of IL-1β mediated by metabolic reprogramming of macrophages. Science 356, 513-519.

Ito, M., Shichita, T., Okada, M., Komine, R., Noguchi, Y., Yoshimura, A., and Morita, R. (2015). Bruton's tyrosine kinase is essential for NLRP3 inflammasome activation and contributes to ischaemic brain injury. Nat Commun 6, 7360.

Jupelli, M., Shimada, K., Chiba, N., Slepenkin, A., Alsabeh, R., Jones, H. D., Peterson, E., Chen, S., Arditi, M., and Crother, T. R. (2013). Chlamydia pneumoniae infection in mice induces chronic lung inflammation, iBALT formation, and fibrosis. PLoS One 8, e77447.

Kelly, B., Tannahill, G. M., Murphy, M. P., and O'Neill, L. A. (2015). Metformin Inhibits the Production of Reactive Oxygen Species from NADH:Ubiquinone Oxidoreductase to Limit Induction of Interleukin-Ibeta (IL-1beta) and Boosts Interleukin-10 (IL-10) in Lipopolysaccharide (LPS)-activated Macrophages. J Biol Chem 290, 20348-20359.

Kolb, M., Margetts, P. J., Anthony, D. C., Pitossi, F., and Gauldie, J. (2001). Transient expression of IL-1beta induces acute lung injury and chronic repair leading to pulmonary fibrosis. J Clin Invest 107, 1529-1536.

Labuzek, K., Liber, S., Gabryel, B., Adamczyk, J., and Okopien, B. (2010). Metformin increases phagocytosis and acidifies lysosomal/endosomal compartments in AMPK-dependent manner in rat primary microglia. Naunyn Schmiedebergs Arch Pharmacol 381, 171-186.

Lee, H. M., Kim, J. J., Kim, H. J., Shong, M., Ku, B. J., and Jo, E. K. (2013). Upregulated NLRP3 inflammasome activation in patients with type 2 diabetes. Diabetes 62, 194-204.

Li, A., Zhang, S., Li, J., Liu, K., Huang, F., and Liu, B. (2016). Metformin and resveratrol inhibit Drp1-mediated mitochondrial fission and prevent ER stress-associated NLRP3 inflammasome activation in the adipose tissue of diabetic mice. Mol Cell Endocrinol 434, 36-47.

Li, J., Wei, Q., Li, W. L., McCowen, K. C., Xiong, W., Liu, J., Jiang, W., Marin, T., Thomas, R.l., He, M., et al. (2020). Metformin use in diabetes prior to hospitalization: Effects on mortality in COVID-19 ENDOCRINE PRACTICE 26.

Li, X., and Ma, X. (2020). Acute respiratory failure in COVID-19: is it "typical" ARDS?Crit Care 24, 198.

Liu, X., Zhang, Z., Ruan, J., Pan, Y., Magupalli, V. G., Wu, H., and Lieberman, J. (2016). Inflammasome-activated gasdermin D causes pyroptosis by forming membrane pores. Nature 535, 153-158.

Liu, Z. G., Hsu, H., Goeddel, D. V., and Karin, M. (1996). Dissection of TNF receptor 1 effector functions: JNK activation is not linked to apoptosis while NF-kappaB activation prevents cell death. Cell 87, 565-576.

Luo, P., Qiu, L., Liu, Y., Liu, X. L., Zheng, J. L., Xue, H. Y., Liu, W. H., Liu, D., and Li, J. (2020). Metformin Treatment Was Associated with Decreased Mortality in COVID-19 Patients with Diabetes in a Retrospective Analysis. Am J Trop Med Hyg 103, 69-72.

Luo, Y., and Zheng, S. G. (2016). Hall of Fame among Pro-inflammatory Cytokines: Interleukin-6 Gene and Its Transcriptional Regulation Mechanisms. Front Immunol 7, 604.

Marcucci, F., Romeo, E., Caserta, C. A., Rumio, C., and Lefoulon, F. (2020). Context-Dependent Pharmacological Effects of Metformin on the Immune System. Trends Pharmacol Sci 41, 162-171.

Markowicz-Piasecka, M., Sikora, J., Szydlowska, A., Skupien, A., Mikiciuk-Olasik, E., and Huttunen, K. M. (2017). Metformin—a Future Therapy for Neurodegenerative Diseases: Theme: Drug Discovery, Development and Delivery in Alzheimer's Disease Guest Editor: Davide Brambilla. Pharm Res 34, 2614-2627.

Matthay, M. A., Zemans, R. L., Zimmerman, G. A., Arabi, Y. M., Beitler, J. R., Mercat, A., Herridge, M., Randolph, A. G., and Calfee, C. S. (2019). Acute respiratory distress syndrome. Nat Rev Dis Primers 5, 18.

McElroy, G. S., Reczek, C. R., Reyfman, P. A., Mithal, D. S., Horbinski, C. M., and Chandel, N. S. (2020). NAD+ Regeneration Rescues Lifespan, but Not Ataxia, in a Mouse Model of Brain Mitochondrial Complex I Dysfunction. Cell Metab 32, 301-308 e306.

Menezes, S. L., Bozza, P. T., Neto, H. C., Laranjeira, A. P., Negri, E. M., Capelozzi, V. L., Zin, W. A., and Rocco, P. R. (2005). Pulmonary and extrapulmonary acute lung injury: inflammatory and ultrastructural analyses. J Appl Physiol (1985) 98, 1777-1783.

Mills, E. L., Kelly, B., Logan, A., Costa, A. S. H., Varma, M., Bryant, C. E., Tourlomousis, P., Dabritz, J. H. M., Gottlieb, E., Latorre, I., et al. (2016). Succinate Dehydrogenase Supports Metabolic Repurposing of Mitochondria to Drive Inflammatory Macrophages. Cell 167, 457-470 e413.

Molina, J. R., Sun, Y., Protopopova, M., Gera, S., Bandi, M., Bristow, C., McAfoos, T., Morlacchi, P., Ackroyd, J., Agip, A. A., et al. (2018). An inhibitor of oxidative phosphorylation exploits cancer vulnerability. Nat Med 24, 1036-1046.

Nakahira, K., Haspel, J. A., Rathinam, V. A., Lee, S. J., Dolinay, T., Lam, H. C., Englert, J. A., Rabinovitch, M., Cernadas, M., Kim, H. P., et al. (2011). Autophagy proteins regulate innate immune responses by inhibiting the release of mitochondrial DNA mediated by the NALP3 inflammasome. Nat Immunol 12, 222-230.

Nies, A. T., Koepsell, H., Winter, S., Burk, O., Klein, K., Kerb, R., Zanger, U. M., Keppler, D., Schwab, M., and Schaeffeler, E. (2009). Expression of organic cation transporters OCT1 (SLC22A1) and OCT3 (SLC22A3) is affected by genetic factors and cholestasis in human liver. Hepatology 50, 1227-1240.

Park, M. J., Moon, S. J., Baek, J. A., Lee, E. J., Jung, K. A., Kim, E. K., Kim, D. S., Lee, J. H., Kwok, S. K., Min, J. K., et al. (2019). Metformin Augments Anti-Inflammatory and Chondroprotective Properties of Mesenchymal Stem Cells in Experimental Osteoarthritis. J Immunol 203, 127-136.

Pollak, M. (2017). The effects of metformin on gut microbiota and the immune system as research frontiers. Diabetologia 60, 1662-1667.

Pollak, M. N. (2012). Investigating metformin for cancer prevention and treatment: the end of the beginning. Cancer Discov 2, 778-790.

Richardson, S., Hirsch, J. S., Narasimhan, M., Crawford, J. M., McGinn, T., Davidson, K. W., and the Northwell, C.-R. C., Barnaby, D. P., Becker, L. B., Chelico, J. D., et al. (2020). Presenting Characteristics, Comorbidities, and Outcomes Among 5700 Patients Hospitalized With COVID-19 in the New York City Area. JAMA.

Ridker, P. M., MacFadyen, J. G., Thuren, T., Everett, B. M., Libby, P., Glynn, R. J., and Group, C. T. (2017). Effect of interleukin-Ibeta inhibition with canakinumab on incident lung cancer in patients with atherosclerosis: exploratory results from a randomised, double-blind, placebo-controlled trial. Lancet 390, 1833-1842.

Rodrigues, T. S., de Sa, K. S. G., Ishimoto, A. Y., Becerra, A., Oliveira, S., Almeida, L., Goncalves, A. V., Perucello, D. B., Andrade, W. A., Castro, R., et al. (2021). Inflammasomes are activated in response to SARS-CoV-2 infection and are associated with COVID-19 severity in patients. J Exp Med 218.

Roschewski, M., Lionakis, M. S., Sharman, J. P., Roswarski, J., Goy, A., Monticelli, M. A., Roshon, M., Wrzesinski, S. H., Desai, J. V., Zarakas, M. A., et al. (2020). Inhibition of Bruton tyrosine kinase in patients with severe COVID-19. Sci Immunol 5.

Salminen, A., and Kaarniranta, K. (2012). AMP-activated protein kinase (AMPK) controls the aging process via an integrated signaling network. Ageing Res Rev 11, 230-241.

Sanchez-Lopez, E., Zhong, Z., Stubelius, A., Sweeney, S. R., Booshehri, L. M., Antonucci, L., Liu-Bryan, R., Lodi, A., Terkeltaub, R., Lacal, J. C., et al. (2019). Choline Uptake and Metabolism Modulate Macrophage IL-1beta and IL-18 Production. Cell Metab 29, 1350-1362 e1357.

Saura, J., Tusell, J. M., and Serratosa, J. (2003). High-yield isolation of murine microglia by mild trypsinization. Glia 44, 183-189.

Scozzi, D., Cano, M., Ma, L., Zhou, D., Zhu, J. H., O'Halloran, J. A., Goss, C., Rauseo, A. M., Liu, Z., Peritore, V., et al. (2020). Circulating Mitochondrial

US 12,642,780 B2

61

62

DNA is an Early Indicator of Severe Illness and Mortality from COVID-19. bioRxiv.

Sharif, H., Wang, L., Wang, W. L., Magupalli, V. G., Andreeva, L., Qiao, Q., Hauenstein, A. V., Wu, Z., Nunez, G., Mao, Y., and Wu, H. (2019). Structural mechanism for NEK7-licensed activation of NLRP3 inflammasome. Nature 570, 338-343.

Shi, Q., Liu, S., Fonseca, V. A., Thethi, T. K., and Shi, L. (2019). Effect of metformin on neurodegenerative disease among elderly adult US veterans with type 2 diabetes mellitus. BMJ Open 9, e024954.

Shimada, K., Crother, T. R., Karlin, J., Dagvadorj, J., Chiba, N., Chen, S., Ramanujan, V. K., Wolf, A. J., Vergnes, L., Ojcius, D. M., et al. (2012). Oxidized mitochondrial DNA activates the NLRP3 inflammasome during apoptosis. Immunity 36, 401-414.

Singh, S., and Khan, A. (2020). Clinical Characteristics and Outcomes of Coronavirus Disease 2019 Among Patients With Preexisting Liver Disease in the United States: A Multicenter Research Network Study. Gastroenterology 159, 768-771 e763.

Soberanes, S., Misharin, A. V., Jairaman, A., Morales-Nebreda, L., McQuattie-Pimentel, A. C., Cho, T., Hamanaka, R. B., Meliton, A. Y., Reyfman, P. A., Walter, J. M., et al. (2019). Metformin Targets Mitochondrial Electron Transport to Reduce Air-Pollution-Induced Thrombosis. Cell Metab 29, 335-347 e335.

Tay, M. Z., Poh, C. M., Renia, L., MacAry, P. A., and Ng, L. F. P. (2020). The trinity of COVID-19: immunity, inflammation and intervention. Nat Rev Immunol 20, 363-374.

Trautwein, C., Caelles, C., van der Geer, P., Hunter, T., Karin, M., and Chojkier, M. (1993). Transactivation by NF-IL6/LAP is enhanced by phosphorylation of its activation domain. Nature 364, 544-547.

Tschopp, J., and Schroder, K. (2010). NLRP3 inflammasome activation: The convergence of multiple signalling pathways on ROS production?Nat Rev Immunol 10, 210-215.

Vaez, H., Najafi, M., Rameshrad, M., Toutounchi, N. S., Garjani, M., Barar, J., and Garjani, A. (2016). AMPK activation by metformin inhibits local innate immune responses in the isolated rat heart by suppression of TLR 4-related pathway. Int Immunopharmacol 40, 501-507.

Valencia, W. M., Palacio, A., Tamariz, L., and Florez, H. (2017). Metformin and ageing: improving ageing outcomes beyond glycaemic control. Diabetologia 60, 1630-1638.

Verma, N., Duseja, A., and Singh, V. (2020). Impact of Pre-existing Chronic Liver Disease on the Outcome of Patients with COVID-19 Disease. Gastroenterology.

Wheaton, W. W., Weinberg, S. E., Hamanaka, R. B., Soberanes, S., Sullivan, L. B., Anso, E., Glasauer, A., Dufour, E., Mutlu, G. M., Budigner, G. S., and Chandel, N. S. (2014). Metformin inhibits mitochondrial complex I of cancer cells to reduce tumorigenesis. Elife 3, e02242.

Wilcock, C., and Bailey, C. J. (1994). Accumulation of metformin by tissues of the normal and diabetic mouse. Xenobiotica 24, 49-57.

Winkler, E. S., Bailey, A. L., Kafai, N. M., Nair, S., McCune, B. T., Yu, J., Fox, J. M., Chen, R. E., Earnest, J. T., Keeler, S. P., et al. (2020). SARS-CoV-2 infection of human ACE2-transgenic mice causes severe lung inflammation and impaired function. Nat Immunol 21, 1327-1335.

Wu, C., Chen, X., Cai, Y., Xia, J., Zhou, X., Xu, S., Huang, H., Zhang, L., Zhou, X., Du, C., et al. (2020). Risk Factors Associated With Acute Respiratory Distress Syndrome and Death in Patients With Coronavirus Disease 2019 Pneumonia in Wuhan, China. JAMA Intern Med.

Yang, F., Qin, Y., Wang, Y., Meng, S., Xian, H., Che, H., Lv, J., Li, Y., Yu, Y., Bai, Y., and Wang, L. (2019). Metformin Inhibits the NLRP3 Inflammasome via AMPK/mTOR-dependent Effects in Diabetic Cardiomyopathy. Int J Biol Sci 15, 1010-1019.

Yang, J., Zheng, Y., Gou, X., Pu, K., Chen, Z., Guo, Q., Ji, R., Wang, H., Wang, Y., and Zhou, Y. (2020a). Prevalence of comorbidities and its effects in patients infected with SARS-CoV-2: a systematic review and meta-analysis. Int J Infect Dis 94, 91-95.

Yang, L., Garcia Canaveras, J. C., Chen, Z., Wang, L., Liang, L., Jang, C., Mayr, J. A., Zhang, Z., Ghergurovich, J. M., Zhan, L., et al. (2020b). Serine Catabolism Feeds NADH when Respiration Is Impaired. Cell Metab 31, 809-821 e806.

Yu, L. L., Zhu, M., Huang, Y., Zhao, Y. M., Wen, J. J., Yang, X. J., and Wu, P. (2018). Metformin relieves acute respiratory distress syndrome by reducing miR-138 expression. Eur Rev Med Pharmacol Sci 22, 5355-5363.

Zhang, X. J., Qin, J. J., Cheng, X., Shen, L., Zhao, Y. C., Yuan, Y., Lei, F., Chen, M. M., Yang, H., Bai, L., et al. (2020). In-Hospital Use of Statins Is Associated with a Reduced Risk of Mortality among Individuals with COVID-19. Cell Metab 32, 176-187 e174.

Zhong, Z., Liang, S., Sanchez-Lopez, E., He, F., Shalapour, S., Lin, X. J., Wong, J., Ding, S., Seki, E., Schnabl, B., et al. (2018). New mitochondrial DNA synthesis enables NLRP3 inflammasome activation. Nature 560, 198-203.

Zhong, Z., Umemura, A., Sanchez-Lopez, E., Liang, S., Shalapour, S., Wong, J., He, F., Boassa, D., Perkins, G., Ali, S. R., et al. (2016). NF-kappaB Restricts Inflammasome Activation via Elimination of Damaged Mitochondria. Cell 164, 896-910.

Zhou, R., Yazdi, A. S., Menu, P., and Tschopp, J. (2011). A role for mitochondria in NLRP3.

What is claimed is:

1. A method for one or more of preventing, treating, reducing the severity of acute respiratory distress syndrome (ARDS) in a subject at risk for contracting ARDS and infected with a coronavirus, comprising administering to the subject an effective amount of metformin, thereby preventing, treating, or reducing the severity of ARDS in the subject.

2. The method of claim 1, wherein the subject is suffering from a comorbidity.

3. The method of claim 2, wherein the comorbidity comprises pre-diabetes, type-II diabetes, obesity, or hypertension.

4. The method of claim 1, further comprising administering to the subject a second therapy or therapeutic to treat the subject.

5. The method of claim 1, wherein the subject is a mammal.

6. The method of claim 5, wherein the mammal is a canine, feline, equine, bovine, murine, rat or a human.

7. The method of claim 1, wherein the subject is a pediatric or an adult subject.

8. The method of claim 1, wherein the subject has been selected for the method by assaying for infection with the coronavirus.

9. The method of claim 1, wherein the effective amount of metformin is administered by method comprising inhalation, orally or intraveneously.

10. The method of claim 1, wherein the effective amount of metformin is administered in one or more doses.

11. The method of claim 1, wherein the administration is systemic or local to the infection.

12. The method of claim 1, wherein the treatment of acute respiratory distress syndrome (ARDS) in the subject at risk for contracting ARDS and infected with a coronavirus comprises one or more of: abrogates POLγ-dependent mtDNA synthesis, Ox-mtDNA production, or inhibits NLRP3 inflammasome activation.

13. The method of claim 1, wherein the coronavirus is Sars-CoV-2.

*     *     *     *     *